US010350270B2

(12) United States Patent
McCauley

(10) Patent No.: US 10,350,270 B2
(45) Date of Patent: Jul. 16, 2019

(54) INTERLEUKIN-15 COMPOSITIONS AND USES THEREOF

(71) Applicant: ARMO BioSciences, Inc., Redwood City, CA (US)

(72) Inventor: Scott McCauley, San Francisco, CA (US)

(73) Assignee: Armo Biosciences, Inc., Redwood City, CA (US)

( * ) Notice: Subject to any disclaimer, the term of this patent is extended or adjusted under 35 U.S.C. 154(b) by 0 days.

(21) Appl. No.: 15/513,820

(22) PCT Filed: Oct. 12, 2015

(86) PCT No.: PCT/US2015/055156
§ 371 (c)(1),
(2) Date: Mar. 23, 2017

(87) PCT Pub. No.: WO2016/060996
PCT Pub. Date: Apr. 21, 2016

(65) Prior Publication Data
US 2017/0246253 A1    Aug. 31, 2017

Related U.S. Application Data

(60) Provisional application No. 62/063,784, filed on Oct. 14, 2014.

(51) Int. Cl.
| | | |
|---|---|---|
| *A61K 38/20* | (2006.01) | |
| *C07K 14/54* | (2006.01) | |
| *A61K 9/00* | (2006.01) | |
| *A61K 9/08* | (2006.01) | |
| *A61K 39/395* | (2006.01) | |
| *A61K 45/06* | (2006.01) | |
| *C08G 65/334* | (2006.01) | |
| *G01N 33/50* | (2006.01) | |
| *A61K 47/60* | (2017.01) | |
| *C07K 16/24* | (2006.01) | |

(52) U.S. Cl.
CPC ........ *A61K 38/2086* (2013.01); *A61K 9/0019* (2013.01); *A61K 9/08* (2013.01); *A61K 39/3955* (2013.01); *A61K 45/06* (2013.01); *A61K 47/60* (2017.08); *C07K 14/5443* (2013.01); *C08G 65/3348* (2013.01); *G01N 33/5011* (2013.01); *C07K 16/244* (2013.01); *C07K 2317/56* (2013.01); *C07K 2317/622* (2013.01); *C07K 2317/92* (2013.01); *C07K 2319/30* (2013.01); *C07K 2319/31* (2013.01); *C08G 2650/02* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 5,231,012 A | 7/1993 | Mossmann et al. | |
| 5,252,714 A | 10/1993 | Harris et al. | |
| 5,328,989 A | 7/1994 | Vellekamp et al. | |
| 5,552,303 A * | 9/1996 | Grabstein | C07K 14/5443 435/320.1 |
| 5,624,823 A | 4/1997 | Sachs et al. | |
| 5,643,575 A | 7/1997 | Martinez et al. | |
| 5,665,345 A | 9/1997 | Yarchoan et al. | |
| 5,710,251 A | 1/1998 | Vellekamp et al. | |
| 5,824,784 A | 10/1998 | Kinstler et al. | |
| 5,866,134 A | 2/1999 | Fine et al. | |
| 5,876,969 A | 3/1999 | Fleer et al. | |
| 5,908,621 A | 6/1999 | Glue et al. | |
| 5,919,455 A | 7/1999 | Greenwald et al. | |
| 5,932,462 A | 8/1999 | Harris et al. | |
| 5,945,097 A | 8/1999 | Cutler et al. | |
| 5,951,974 A | 9/1999 | Gilbert et al. | |
| 5,985,263 A | 11/1999 | Lee et al. | |
| 5,985,265 A | 11/1999 | Kinstler et al. | |
| 5,985,857 A | 11/1999 | Kinstler et al. | |
| 5,989,867 A | 11/1999 | Knappe et al. | |
| 6,217,857 B1 | 4/2001 | Mosmann et al. | |
| 6,387,364 B1 | 5/2002 | Ferguson | |
| 6,428,985 B1 | 8/2002 | Bromberg et al. | |
| 6,660,258 B1 | 12/2003 | Tovey | |
| 6,770,272 B2 | 8/2004 | Strom et al. | |
| 6,989,377 B2 | 1/2006 | Hayes et al. | |
| 7,052,684 B2 | 5/2006 | Ferguson | |

(Continued)

FOREIGN PATENT DOCUMENTS

| | | |
|---|---|---|
| CN | 1760209 | 10/2004 |
| CN | 102145178 | 8/2011 |

(Continued)

OTHER PUBLICATIONS

Bernard et al; The Journal of Biological Chemistry; 2004; vol. 279, No. 23, pp. 24313-24322.*
Zhu et al, The Journal of Immunology, 2009; vol. 183, pp. 3598-3607.*
Xu et al, Cancer Research; May 2013; vol. 73, No. 10, pp. 3075-3078.*
Zheng et al, Transplantation; 2006; vol. 81; No. 1, pp. 109-116.*
Caliceti et al, Advanced Drug Delivery Reviews; 2003; vol. 55 pp. 1261-1277.*
Jones et al, Journal of the American Chemical Society, 2012, vol. 134, pp. 7406-7413.*
Accession NP 036986.2; 81148747382; Aug. 10, 2014.
Accession NP 776513.1; GI 41386772; Jan. 4, 2015.

(Continued)

*Primary Examiner* — Bridget E Bunner
(74) *Attorney, Agent, or Firm* — Robert Brian Johnson

(57) ABSTRACT

Interleukin-15 muteins and other interleukin-15-related molecules are described, as well as methods of identifying interleukin-15 muteins and other interleukin-15-related molecules. Also described herein are modifications of the foregoing, which modifications may enhance a property (e.g., half-life) of the muteins or other molecules compared to human interleukin-15. Pharmaceutical compositions and methods of use are also described herein.

25 Claims, 8 Drawing Sheets

Specification includes a Sequence Listing.

(56) References Cited

U.S. PATENT DOCUMENTS

| | | | |
|---|---|---|---|
| 7,052,686 B2 | 5/2006 | Lee et al. | |
| 7,056,701 B2 | 6/2006 | Fleer et al. | |
| 7,261,882 B2 | 8/2007 | Watkins | |
| 7,611,700 B2 | 12/2009 | Gantier et al. | |
| 7,650,243 B2 | 1/2010 | Gantier et al. | |
| 7,666,400 B2 | 2/2010 | Chang et al. | |
| 7,749,490 B2 | 7/2010 | Sommer et al. | |
| 7,939,056 B2 | 5/2011 | Horwitz et al. | |
| 8,044,175 B2 | 10/2011 | Dransfield et al. | |
| 8,067,532 B2 | 11/2011 | MacLean | |
| 8,618,256 B2 | 12/2013 | Cox | |
| 2002/0044921 A1 | 4/2002 | Lee et al. | |
| 2003/0012775 A1 | 1/2003 | Brandt et al. | |
| 2003/0186386 A1 | 10/2003 | Hansen et al. | |
| 2004/0213795 A1 | 10/2004 | Collins et al. | |
| 2004/0253587 A1* | 12/2004 | Grabstein | C07K 14/5443 435/6.13 |
| 2005/0008615 A1 | 1/2005 | Bam et al. | |
| 2005/0260767 A1 | 11/2005 | Clerici et al. | |
| 2006/0046961 A1 | 3/2006 | McKay et al. | |
| 2006/0210534 A1 | 9/2006 | Lee et al. | |
| 2006/0258607 A1 | 11/2006 | Jarosch et al. | |
| 2007/0134197 A1 | 6/2007 | Eichner et al. | |
| 2008/0058246 A1 | 3/2008 | Bhaskaran et al. | |
| 2008/0069797 A1 | 3/2008 | Roncarolo et al. | |
| 2008/0081031 A1 | 4/2008 | Oft et al. | |
| 2008/0096252 A1 | 4/2008 | Zamost et al. | |
| 2009/0035256 A1 | 2/2009 | Sommer et al. | |
| 2009/0214463 A1 | 8/2009 | Slobedman et al. | |
| 2009/0214471 A1 | 8/2009 | Oft et al. | |
| 2009/0311187 A1 | 12/2009 | Berman et al. | |
| 2010/0068147 A1 | 3/2010 | Hibberd et al. | |
| 2010/0111898 A1 | 5/2010 | Pelura | |
| 2010/0129386 A1 | 5/2010 | Elson et al. | |
| 2010/0255496 A1 | 10/2010 | Schrader et al. | |
| 2010/0266532 A1 | 10/2010 | Ferguson | |
| 2010/0297070 A1 | 11/2010 | Dungan et al. | |
| 2011/0158938 A1 | 6/2011 | Bernard et al. | |
| 2011/0312010 A1 | 12/2011 | Manuilov | |
| 2013/0259827 A1* | 10/2013 | Yeghiazarians | A61K 35/28 424/85.2 |
| 2015/0038678 A1 | 2/2015 | Eaton et al. | |

FOREIGN PATENT DOCUMENTS

| | | |
|---|---|---|
| EP | 0251304 | 1/1998 |
| EP | 2066336 | 9/2012 |
| EP | 2537933 | 12/2012 |
| WO | WO1992012725 | 8/1992 |
| WO | WO1992012726 | 8/1992 |
| WO | 199417773 | 8/1994 |
| WO | WO199503411 | 2/1995 |
| WO | WO1995006058 | 3/1995 |
| WO | WO1995019780 | 7/1995 |
| WO | WO1996011953 | 4/1996 |
| WO | WO1997003690 | 2/1997 |
| WO | WO1999032134 | 7/1999 |
| WO | WO2001005821 | 1/2001 |
| WO | WO2001058950 | 8/2001 |
| WO | WO2002026265 | 4/2002 |
| WO | WO2004044006 | 5/2004 |
| WO | WO2004056850 | 7/2004 |
| WO | 2004106486 | 12/2004 |
| WO | WO2006075138 | 7/2006 |
| WO | WO2006119170 | 11/2006 |
| WO | WO2008054585 | 5/2008 |
| WO | WO2009016043 | 2/2009 |
| WO | WO2009036568 | 3/2009 |
| WO | 2010022227 | 2/2010 |
| WO | WO2010077853 | 7/2010 |
| WO | WO2011051489 | 5/2011 |
| WO | WO2012004384 | 1/2012 |
| WO | WO2012050923 | 4/2012 |
| WO | WO2012050930 | 4/2012 |
| WO | WO2013113008 | 8/2013 |
| WO | WO2014172392 | 10/2014 |
| WO | WO2015070060 | 5/2015 |
| WO | WO2015153753 | 10/2015 |

OTHER PUBLICATIONS

Accession NP_001009327.1; 8157164347; Feb. 13, 2011

Accession ABY86619.1; GI 166244598 ; Feb. 4, 2008.

Accession AAC23839.1; GI 3242896; Jun. 8, 2000.

Agata et al. (1996) "Expression of the PD-1 antigen on the surface of stimulated mouse T and B lymphocytes," tnt Immunol; 8(5):765-772.

Aggen (2010) "Engineering Human Single-Chain T Cell Receptors," Dissertation; http://hdl.handle.neU2142/18585, 181 pages.

Alvarez et al. (2012) "Effects of PEGylation and Immune Complex Formation on the Pharmacokinetics and Biodistribution of Recombinant Interleukin1 0 in Mice," Drug Metab DiSJJOS 40(2):360-373.

Ansari and Raghava (2010) "Identification of conformational B-cell Epitopes in an antigen from its primary sequence," Immunome Res; 6:9pgs.

Ansell et al. (2002) "Phase 1 study of interleukin-12 in combination with rituximab in patients with B-cell non-Hodgkin lymphoma," Blood; 99:67-74.

Arakawa and Tsumoto (2003) "The effects of arginine on refolding of aggregated proteins: not facilitate refolding, but suppress aggregation," Biochemical and Biophysical Research Communications. 304: 148-152.

Armstrong et al. (1996) "Interleukin 10 (IL-10) regulation of tumour necrosis factor ex (TNF-cx) from human alveolar macrophages and peripheral blood monocytes," Thorax- 51:143-149.

Asadullah et al. (1999) "Interleukin 10 Treatment of Psoriasis," Arch Dermatol.; 135-187-192.

Asadullah et al. (2003) "Interleukin 10 Therapy—Review of a New Approach," Pharmacal. Rev.; 55-241-269.

Bajetta et al. (1998) "Pilot Study of Subcutaneous Recombinant Human Interleukin 12 in Metastatic Melanoma," Clinical Cancer Research; 4:75-85.

Banerjee et al. (2012) "Poly(ethylene glycoi)—Prodrug Conjugates: Concept, Design, and Applications," Journal of Drug Delivery; Article ID 103973:17 pages.

Bea at al. (2011) "Performance Evaluation of a Multiplex Assay for Future Use in Biomarker Discovery Efforts to Predict Body Composition," Clin Chern Lab Med.; 49(5):817-824.

Berger et al. (2009) "Safety and immunologic effects of IL-15 administration in nonhuman primates," Blood; 114:2417-2426. Berger et al. (2009) "Safety and immunologic effects of IL-15 administration in nonhuman primates," Blood; 114:2417-2426.

Berman et al. (1996) "Systemic administration of cellular IL-1 0 induces an effective specific, and long-lived immune response against established tumors in mice," J Immuno/ 157:231-238.

Bilzer et al. (2006) "Role of Kupffer cells in host defense and liver disease," Liver International; 26:1175-1186.

Biswas et al. (2007) "Pathogen_specific CD8 T Cell Responses Are Directly Inhibited by IL-10," J Immunol.; 179:4520-4528.

Brady et al. (1994) "Reflections on a peptide," Nature; 368:692-693.

Brooks et al. (2008) "IL-10 and PD-L 1 operate through distinct pathways to suppress T-cell activity during persistent viral infection," PNAS; 1 05(51):20428-20433.

Burgess (2009) "Refolding Solubilized Inclusion Body Proteins," Methods in Enzymology; 463:259-282.

Cai et al. (1999) "IL-10 enhances NK cell proliferation, cytotoxicity and production of IFNq when combined with IL-18," Eur. J. Immunol.; 29:2658-2665.

Caliceti et al. (2012) "Effect of Plasma Membrane Cholesterol Depletion on Glucose Transport Regulation in Leukemia Cells," PLoS One; 7:e41246.

Cannistra & Niloff (1996) "Cancer of the uterine cervix," New Eng I J Med 334:1030-1038.

(56) References Cited

OTHER PUBLICATIONS

Cao et al. (2011) "Janus kinase activation by cytokine oncostatin M decreases PCSK9 expression in liver cells," *J Lipid Res.*; 52(3):513-530.

Capitini et al. (2009) "Modulating T cell Homeostasis with IL-7: Preclinical and Clinical Studies," *J Intern Med*; 266(2):141-153.

Cebon et al. (2003) "Two phase I studies of low dose recombinant human IL-12 with Melan-A and influenza peptides in subjects with advanced malignant melanoma," *Cancer Immunity*; 3:7 (18 pages).

Chamow et al. (1994) "Modification of CD4 Immunoadhesin with Monomethoxypoly(ethylene glycol) Aldehyde via Reductive Alkylation," *Bioconjugate Chern.*• 5:133-140.

Chang, et al., (2017) "CARs: Synthetic immunoreceptors for cancer therapy and beyond", Trends Mol. Med., 23:430-450.

Chan et al. (2015) "The Potentiation of IFN-y and Induction of Cytotoxic Proteins by Pegylated IL-1 0 in Human CD8 T Cells," *J Interferon Cytokine Res*; 35(12):948-955.

Chen & Zlotnik (1991) "IL-10: a novel cytotoxic T cell differentiation factor," *J Immunol*; 147:528-534.

Chen et al. (2007) "Prediction of linear B-cell epitopes using amino acid pair antigenicity scale," *Amino Acids*; 33:423-428.

Choi et al. (2006) "Serum adiponectin, interleukin-1 0 levels and inflammatory markers in the metabolic 1-18 syndrome," *Diabetes Research and Clinical Practice*; 75:235-240.

Chmielewski, et al, (2015) "TRUCKs: the fourth generation of CARs", Exp_ Opin_ Bioi. Ther., 15:1145-1154.

Collins et al. (2012) "Trastuzumab induces antibody-dependent cellmediated cytotoxicity (ADCC) in HER-2-non-amplified breast cancer cell lines," *Annals of Oncoloav*: 23:1788-1795.

Cindric, et al., (2007) "Structural characterization of PEGylated rHuG-CSF and location of PEG attachment sites". Journal of Pharmaceutical and Biomedical Analysis. New York. NY. US 44(2):388-395.

Compton et al. (2004) "Pathogenesis of Enterotropic Mouse Hepatitis Virus in Immunocompetent and Immunodeficient Mice," *Comparative Medicine*; 54(6):681-689.

Conlon et al. (2014) "Redistribution, Hyperproliferation, Activation of Natural Killer Cells and CDS T Cells, and Cytokine Production During First-in-Human Clinical Trial of Recombinant Human Interleukin-15 in Patients With Cancer," *Journal of Clinical Oncology*; 33(1):74-82.

Couder et al. (1993) "Synthesis and biological activities of 4J(CH2NH) pseudopeptide analogues of the C-terminal hexapeptide of neurotensin," *Int. J. Peptide Protein Res.*; 41:1 81-184.

D'Andrea et al. (1993) "Interleukin 10 (IL-10) Inhibits Human Lymphocyte Interferon 3,-Production by Suppressing Natural Killer Cell Stimulatory Factor/IL-12 Synthesis in Accessory Cells" *J. ExJJ. Med*• 178:1041-1048.

Das et al. (2012) "IL-1 0-Producing Regulatory B Cells in the Pathogenesis of Chronic Hepatitis B Virus Infection," *J. Immunol.*; 189(8):3925-3935.

Davidson & Diamond (2001) "Autoimmune diseases," *New Eng/ J Med*; 345:340-350.

De Waal Malefyt et al. (1991) "Interleukin 10 (IL-10) and viraiiL-10 strongly reduce antigen-specific human T cell proliferation by diminishing the antigen-presenting capacity of monocytes via downregulation of class II major histocompatibility complex expression," *J Exp Med*; 174(4):915-924.

De Waal Malefyt et al. (1991) "Interleukin 10(1L-10) Inhibits Cytokine Synthesis by Human Monocytes: an Autoregulatory Role of IL-10 Produced by Monocytes," *J. Exp. Med* • 174:1209-1220.

Devay et al. (2013) "Characterization of Proprotein Convertase Subtilisin/Kexin Type 9 (PCSK9) Trafficking Reveals a Novel Lysosomal Targeting Mechanism via Amyloid Precursor-like Protein 2 (APLP2)" *J. Bioi. Chem.*• 288:10805-10818.

Dolgin (2011) "Trial puts niacin- and cholesterol dogma-in the line of fire," *Natue Medicine*; 17(7):356.

Dorner et al. (2011) "A genetically humanized mouse model for hepatitis C virus infection," *Nature*; 474:208-211.

Easy Surf. Blood Volume Calculator [online], Oct. 1, 2012 [retrieved Aug. 18, 2014]. Available on the internet: <URL: https://web.archive.org/web/20121001142649/http://www.easysurf.cc/cnver22.htm >.

Ehrlich et al. (2013) "Preparation and Characterization of Albumin Conjugates of a Truncated Peptide YY Analogue for Half-Life Extension," *Bioconjug. Chern.*; 24(12):2015-2024.

El-Manzalawy et al. (2008) "Predicting linear B-cell epitopes using string kernels," *J Mol Recognit*; 21:243-255.

Emmerich et al. (2012) "IL-10 directly activates and expands tumor-resident CD8(+) T cells without de novo infiltration from secondary lymphoid organs," *Cancer Res*; 72(14):3570-3581.

Engel et al. (2006) "Using Endoproteinases Asp-N And Glu-e to Improve Protein Characterization," *Promega Corporation*; 10$^{th}$ edition.

Enzinger & Mayer (2003) "Esophageal cancer," *New Eng I J Med*; 349:2241-2252.

Fahnert et al. (2012) "Using Folding Promoting Agents in Recombinant Protein Production: A Review," *Methods inn Molecular Biology*; 824:3-36.

Fang et al. (2015) "Programmed Death 1 (PD-1) is involved in the development of proliferative diabetic retinopathy by mediating activation-induced apoptosis," *Mol Vis*; 21 :901-910.

Farrar et al. (1999) "Cancer dormancy. VII. A regulatory role for COB+ T cells and IFN-gamma in establishing and maintaining the tumor-dormant state," *J Imunol* 162:2842-2849.

Fehniger and Caligiuri (2001) "Interleukin 15: biology and relevance to human disease," *Blood*; 97:14-32.

Feingold et al. (1996) "Endotoxin, TNF, and IL-I decrease cholesterol ?a-hydroxylase mRNA levels and activity," *Journ of Lipid Res*; 37:223-228.

Fiorentino et al. (1989) "Two types of mouse T helper cell. IV. Th2 clones secrete a factor that inhibits cytokine production by Th1 clones," *J Exp Med*; 170:2081-2095.

Forastiere et al. (2001) "Head and neck cancer," *New Eng/ J Med* 345:1890-1900.

Fridman et al. (2012) "The immune contexture in human tumours: impact on clinical outcome," *Nature*; 12:298-306.

Fry and Mackall (2002) "Interleukin-7: from bench to clinic," *Blood*; 99:3892-3904.

Fujiwara et al. (2010) "Extraction and purification of human interleukin-1 0 from transgenic rice seeds," *Protein Expression and Purification*; 72:125-130.

Gargett et al. "Different cytokine and stimulation conditions influence the expansion and immune phenotype of third-general ion chimeric antigen receptor T cells specific for tumor antigen GD2", Cytotherapy, vol. 17, No. 4, Apr. 2015 (Apr. 2015) , pp. 487-495.

Galon et al. (2013) "The Continuum of Cancer Immunosurveillance: Prognostic, Predictive, and Mechanistic Signatures," *Immunity*; 39:11-26.

Gameren et al. (1994) "Effects of Recombinant human interleukin-6 in cancer patients: a phase 1-11 study," *Blood*; 84:1434-1441.

Gao et al. (2012) "BEST: Improved Prediction of B-Cell Epitopes from Antigen Sequences," *PLoS One*; 7(6): e401 04.

GenBank Accession No. M37897 "Mouse interleukin 10 mRNA, complete cds," dated Apr. 27, 1993.

GenBank Accession No. NP 000563 "interleukin-1 0 precursor [Homo sapiens]," dated Mar. 3, 1995.

Georgescu et al. (1997) "Interleukin-1 0 Promotes Activation-induced Cell Death of SLE Lymphocytes Mediated by Fas Ligand," *J. Clin. Invest.*; 100:2622-2633.

Gerstein et al. (2008) "Effects of Intensive Glucose Lowering in Type 2 Diabetes," *New England J of Medicine*; 358(24):2545-2559.

Gesser et al. (1997) "Identification of functional domains on human interleukin 1 0," *Proc. Nat/. Acad. Sci.*; 94:14620-14625.

Gierens et al. (2000) "Interleukin-6 Stimulates LDL Receptor Gene Expression via Activation of Sterol-Responsive and Sp1 Binding Elements," *Arteriosc/er Thromb Vase Biof* •: 20:1777-1783.

Gill et al., (2015) "Going viral: Chimeric antigen receptor T-cell therapy for hematological malignancies", Immunological Reviews 28150181 Blackwell Publishing Ltd GBR vol . 263 No. 1, pp. 68-89.

(56) References Cited

OTHER PUBLICATIONS

Gregoriadis et al., (2005) "Improving the therapeutic efficacy of peptides and proteins: A role for polysialic acids," *Int. J. Pharmaceutics*; 300(1-2):125-130.
Groux et al. (1998) "A transgenic model to analyze the immunoregulatory role of IL-10 secreted by antigen-presenting cells," *J Immunol*; 162:1723-1729.
Groux et al. (1998) "Inhibitory and stimulatory effects of IL-1 0 on human COB+ T cells," *J lmmunol*; 160:3188-3193.
Hagen Baugh et al. (1997) "Altered immune responses in interleukin 1 0 transgenic mice," *J Exp Med*; 185:2101-2110.
Hamada et al. (2009) "Effect of Additives on Protein Aggregation," *Current Pharm Biotech*; 10:400-407.
Hashizume et al. (201 0) "Overproduced interleukin 6 decreases blood lipid levels via upregulation of very-low-density lipoprotein receptor," *Ann Rheum Dis*; 69:7 41-7 46.
Heeschen et al. (2003) "Serum Level of the Antiinflammatory Cytokine Interleukin-10 Is an Important Prognostic Determinant in Patients With Acute Coronary Syndromes," *Circulation•* 1 07:2109-2114.
Hermanson, et al., (2015) "Utilizing chimeric antigen receptors to direct natural killer cell activity", Frontiers in immunology, 6:195.
Hombach et al. (2013) "Arming Cytokine-induced Killer Cells With Chimeric Antigen Receptors: CD28 Outperforms Combined CD28-0X40 'Super-stimulation'," *Molecular Therapy*; 12:2268-2277.
Hombach, et al., (2012) "OX40 costimulation by a chimeric antigen receptor abrogates CD28 and IL-2 induced IL-10 secretion by redirected CD4+ T cells", OncoImmunol., 1 :458-466.
Howard et al. (1993) "Interleukin 1 0 Protects Mice from Lethal Endotoxemia," *J. Exp. Med.*; 177:1205-1208.
Huang et al. (1996) "Interleukin 10 Suppresses Tumor Growth and Metastasis of Human Melanoma Cells: Potential Inhibition of Angiogenesis," Clinical Cancer Research *The American ASSN for Cancer Research* 2(12):1969-1979.
Huang et al. (2010) "Depletion of Liver Kupffer Cells Prevents the Development of Diet-Induced Hepatic Steatosis and Insulin Resistance," 59:347-357.
Huntington et al. (2008) "IL-15 trans-presentation promotes human NK cell development and differentiation in vivo," *J. Exp. Med.*; 206:25-34.
Hustoft et al. (2012) "A Critical Review of Trypsin Digestion for LC-MS Based Proteomics," *In Tech*; Chapter 4.
Infante et al. (2015) "A first-in-human dose escalation study of PEGylated recombinant human IL-1 0 (AM001 0) in advanced solid tumors," ASCO Meeting Abstracts; 33(15 suppl):3017.
International Search Report; PCT/US01/42431, dtd. Aug. 20, 2002, 4 pages.
Ishikawa et al. (2005) "Interleukin-10 plasmid DNA inhibits liver and lung metastasis of Colon 26 adenocarcinoma in mice," *Proceedings of the Annual Meeting, American Association for Cancer Research* vol. 46 Abstract# 3364.
Izbicki et al. (1997) "Prognostic value of immunohistochemically identifiable tumor cells in lymph nodes of patients with completely resected esophageal cancer," *New Eng/ J Med•*337:1188-1194.
Jameson et al. (1994) "A rationally designed CD4 analogue inhibits experimental allergic encephalomyelitis," *Nature*; 368:744-746.
Jaspers, et al., (2017) "Development of CART cells designed to improve antitumor efficacy and safety", Pharmac. & Therap., http://dx.doi.org,/1 0.1 016/j.pharmthera.2017.03.012.
Jensen, et al., (2015) "Designing chimeric antigen receptors to effectively and safely target tumors", Curr. Opin. mmunol., 33:9-15.
Jevsevar et al. (2010) "PEGylation of therapeutic proteins," *Biotechnol. J.*; 5:113-128.
Jiang et al. (2015) "T-cell exhaustion in the tumor microenvironment," *Cell Death Dis*; 6:e1792.
Josephson et al. (2001) "Crystal Structure of the IL-1 0/1L-1 OR1 Complex Reveals A Shared Receptor Binding Site," *Immunity*; 14:35-46.
Jungbauer et al. (2007) "Current status of Technical protein refolding," *Journal of Biotechnology*; 128:587-596.
Katre (1993) "The Conjugation of Proteins with Polyethylene Glycol and Other Polymers Altering Properties of Proteins to Enhance their Therapeutic Potential," *Advanced Druq Delivery Reviews•*1 0(1):91-114.
Khow and Suntrarachun (2012) "Strategies for production of active eukaryotic proteins in bacterial expression system," *Asian Pac. J. Biomed.*; 2(2):159-162.
Kimball et al (2002) "Clinical and Immunologic Assessment of Patients With Psoriasis in a Randomized, Double-blind, Placebo-Controlled Trial Using Recombinant Human Interleukin 10 *Arch Dermato/*" 138:1341-1346.
Kinstler et al. (1996) "Characterization and Stability of N-terminally PEGylated rhGCSF", *Pharm. Res.*; 13:996-1002.
Klompus et al. (2008) "A simple novel method for the preparation of noncovalent homodimeric, biologically active human interleukin 10 in *Escherichia coli*-Enhancing protein expression by degenerate PCR of 59 DNA in the open reading frame," *Protein Expression and Purification*; 62:199-205.
Kokura et al. (2003) "The blocking of NFkB activation by systemicinterleukin-1 0 gene therapy inhibits liver and lung metastasis of colon 26 adenocarcinoma in mice" *Gastroenteroloav:* 124(4): Abstract No. W965.
Kokura et al. (2005) "Interleukin-1 0 plasmid DNA inhibits subcutaneous tumor growth of Colon adenocarcinoma in mice," *Cancer Letters*; 218:171-179.
Kong et al. (2005) "In vivo activities of cytokine oncostatin Min the regulation of plasma lipid levels," *Journal of Lipid Research*; 46:1163-1171.
Korholz et al. (1997) "The Role of Interleukin-1 0 (IL-1 0) in IL-15-Mediated T-Cell Responses," *Blood*; 90(11):4513-4521.
Kundu et al. (1996) "Anti metastatic and antitumor activities of interleukin 10 in a murine model of breast cancer," *J Nail Cancer /nsf*; 88:536-541.
Kundu et al. (1997) "Interleukin-1 0 inhibits tumor metastasis, down regulates MHC class I, enhances NK lysis," *Cellular Immunology, Academic Press*; 180(1):55-61.
Kute et al. (2012) "Understanding key assay parameters that affect measurements of trastuzumab-mediated ADCC against Her2 positive breast cancer cells," *OncoImmunology*; 1 (6):81 0-821.
Langowski et al. (2006) "IL-23 promotes tumour incidence and growth," *Nature*;442:461-465.
Lasek et al. (2014) "Interleukin 12: still a promising candidate for tumor immunotherapy?" Cancer ImmunolImmunother; 63:419-435.
Le et al. (2001) "Pre-existing tumor-sensitized T cells are essential for eradication of established tumors by IL-12 and cyclophosphamide plus IL-12," *J Immunol*; 167:6765-6772.
Lehmann et al. (2014) "IL-12 Directs Further Maturation of Ex Vivo Differentiated NK Cells with Improved Therapeutic Potential," *PLoS One*; 9(1):e87131 (12 pages).
Lewington and Clark (2005) "Combined Effects of Systolic Blood Pressure and Total Cholesterol on Cardiovascular Disease Risk," *Circulation*; 112:3373-3374.
Lindhout et al. (2011) "Site-specific enzymatic polysialylation of therapeutic proteins using bacterial enzymes," *PNAS*; 1 08(18)7397-7402.
Liu et al. (2003) "IL-10 Mediates Suppression of the CD8 T CeiiiFN-y Response to a Novel Viral Epitope in a Primed Host," *J Immunol*; 171 :4 765-4 772.
Loebbermann et al. (2012) "IL-1 0 Regulates Viral Lung Immunopathology during Acute Respiratory Syncytial Virus Infection in Mice," *PLoS ONE*; 7(2):e32371.
Lopez et al. (2005) "IL-12 and IL-1 0 Expression Synergize to Induce the Immune-Mediated Eradication of Established Colon and Mammary Tumors and Lung Metastasis," *J Immuno/* 175:5885-5894.
Lowe et al. (1998) "Impact of Major Cardiovascular Disease Risk Factors, Particularly in Combination, on 22-Year Mortality in Women and Men," *Arch Intern Med*; 158:2007-2014.
Lu et al. (2004) "Prognostic factors in resected stage I non-small-cell lung cancer: a multivariate analysis of six molecular markers," *J Clin Oneal*; 22:4575-4583.

(56) References Cited

OTHER PUBLICATIONS

Lugli et al. (2010) "Transient and persistent effects of IL-15 on lymphocyte homeostasis in nonhuman primates," *Blood*; 116:3238-3248.

Lynch and Chapelle (2003) "Hereditary colorectal cancer," *New Eng I J Med*; 348:919-932.

Martin et al. (2001) "B-Cell Deficiency Suppresses Vaccine-Induced Protection against Murine Filariasis but Does Not Increase the Recovery Rate for Primary Infection," *Infect. Immun.* • 69(11):7067-7073.

Mattos et al. (2012) "PEGylation of interleukin-1 0 improves the pharmacokinetic profile and enhances the antifibrotic effectivity in CCI.-induced fibrogenesis in mice," *J Control Release*• 162(1):84-91.

Maus et al. (2014) "Antibody-modified T cells: CARs take the front seat for hematologic malignancies," *Blood*; 123(17):2625-2635.

Miki Toyokazu et al. (2000) "Anti-metastatic effect of IL-10 gene modification in human lung cancer cells is differentially regulated by organ microenvironments," *Proceedings of the Annual Meeting American Association for Cancer Research*• 41:3.

Monk (2011) "A Strategy for the Quantification of Protein Polyethylene Glycol (PEG) Derivatized Sites using iTRAQ," *University of California*, San Diego; 1-51.

Moore et al. (1990) "Homology of cytokine synthesis inhibitory factor (IL-1 0) to the Epstein-Barr virus gene BCRFI," *Science*; 248:1230-1234.

Moran et al. (1994) "Human leukemia inhibitory factor inhibits development of experimental atherosclerosis," *Arterioscler Thromb Vase Biol.*; 14(8):1356-1363.

Motzer et al. (2001) "Randomized Multicenter Phase II Trial of subcutaneous recombinant Human Interleukin-12 Versus Interferon-a2a for Patients with Advanced Renal Cell Carcinoma" *Journal of Interferon and Cytokine Research*• 21:257-263.

Muecke, et al., (2000) "Suppression of the Tumorigenic Growth of Burkitt'S Lymphoma Cells in Immunodeficient Mice by Cytokine Gene Transfer Using EBV-Derived Episomal Expression Vectors", Int. J. Cancer, 86:301-306.

Mumm et al. (2011) "IL-10 elicits IFNy-dependent tumor immune surveillance," *Cancer Cell*; 20(6):781-796.

Mumm et al., (2012) "Killing from within" *OncoImmunology*, 1(9):1598-1600.

Naicker et al. (2009) "Interleukin-1 0 Promoter Polymorph isms Influence HIV-1 Susceptibility and Primary HIV-1 Pathogenesis," *J. Infect. Dis.*; 200(3):448-452.

Natsume et al. (2009) "Improving effector functions of antibodies for cancer treatment: Enhancing ADCC and CDC," Drug Design, Development and Therapy; 3:7-16.

Nenseter et al. (1992) "Role of liver endothelial and Kupffer cells in clearing low density lipoprotein from blood in hypercholesterolemic rabbits," *J of Lipid Res*; 33:867-877.

Neven et al. (2013) "A Mendelian predisposition to B cell lymphoma caused by IL-1 or deficiency," *Blood*; 122(23):3712-3722.

Newick, et al., (2016) "CART cell therapy for solid tumors", Annual Rev. Med., 68:139-152.

Neyrinck et al. (2009) "Critical role of Kupffer cells in the management of diet-induced diabetes and obesity," *Biochemical and Biophysical Research Communications*; 385:351-356.

Nicholls et al. (2012) "Is niacin ineffective? Or did AIM-HIGH miss its target?," *Cleveland Clinic Journ of Med*; 79(1):38-43.

Noguchi et al. (2003) "PDX-1 Protein Containing Its Own Antennapedia-Like Protein Transduction Domain Can Transduce Pancreatic Duct and Islet Cells," Diabetes: 52(7):1732-1737.

Osaki et al. (1999) "Potent antitumor effects mediated by local expression of the mature form of the interferon-y inducing factor, interleukin-18 (IL-18)," *Gene Therapy*; 6:808-815.

Osborne (1998) "Tamoxifen in the treatment of breast cancer," *New Eng/ J Med*; 339:1609-1618.

Overdijk et al. (2011) Epidermal Growth Factor Receptor (EGFR) Antibody-Induced Antibody-Dependent Cellular Cytotoxicity Plays a Prominent Role in Inhibiting Tumoriqenesis Even of Tumor Cells Insensitive to EGFR Siqnaling Inhibition , *J Immunol.* Sep. 15, 2011;187(6):3383-90.

Pardoll (2012) "The blockade of immune checkpoints in cancer immunotherapy," *Cancer*; 12:252-264.

Park et al. (2011) "IL-15-Induced IL-1 0 Increases the Cytolytic Activity of Human Natural Killer Cells," *Mol. Cells*; 32:265-272.

Pasut and Veronese (2012) "State of the art in PEGylation: The great versatility achieved after forty years of research," *Journal of Controlled Release*; 161 :461-472.

Payne et al. (201 0) "Product development issues for PEGylated proteins," *Pharmaceutical Development and Technology*; 16:423-440.

Pegram et al. (2012) "Interleukin 12: Stumbling Blocks and Stepping Stones to Effective Anti-Tumor Therapy," *Advancements in Tumor Immunotherapy and Cancer Vaccines*• Chapter 10:197-218.

Pellegrini et al. (2011) "IL-7 Engages Multiple Mechanisms to Overcome Chronic Viral Infection and Limit Organ Pathology," *Cell*; 144:1-13.

Pettit et al. (1997) "Structure-Function Studies of Interleukin 15 using Site-specific Mutagenesis, Polyethylene Glycol Conjugation, and Homology Modeling," *J. Bioi. Chern.* 272:2312-2318.

Rachmawati et al. (2004) "Pharmacokinetic and Biodistribution Profile of Recombinant Human Interleukin-1 0 Following Intravenous Administration in Rats with Extensive Liver Fibrosis" *Pharm. Res.*• 21 (11):2072-2078.

Rachmawati et al. (2007) "Chemical Modification of Interleukin-1 0 with Man nose 6-Phosphate Groups Yields a Liver-Selective Cytokine," *Drug Metabolism and Disposition*; 35(5):814-821.

Radwanski et al. (1998) "Pharmacokinetics and Leukocyte Responses of Recombinant Human Interleukin-10," *Pharm. Res.*; 15(12):1895-1901.

Ramirez-Montagut et al. (2003) "Immunity to melanoma: unraveling the relation of tumor immunity and autoimmunity," *Oncogene*; 22:3180-3187.

Re et al. (2002) "Preclinical evaluation of the anti proliferative potential of STI571 in Hodgkin's disease," *British Journal of Cancer*; 86:1333-1335.

Reynolds, et al. (2002) "Proteolytic 180 Labeling for Comparative Proteomics: Evaluation of Endoprotease Glu-e as the Catalytic Agent," *Journal of Proteome Research*1 (1):27-33.

Roberts et al. (2012) "Chemistry for peptide and protein PEGylation," *Advanced Drug Delivery Reviews*; 64:116-127.

Rolfe et al. (2003) "Leukaemia inhibitory factor retards the progression of atherosclerosis," *Cardiovascular Research*; 58:222-230.

Russo et al. (2006) "Randomized trial of pegylated interferon a-2b monotherapy in haemodialysis patients with chronic hepatitis C," *Nephrol Dial Transplant*; 21:437-443.

Saha and Raghava (2006) "Prediction of continuous B-cell epitopes in an antigen using recurrent neural network," *Proteins*; 65:40-48.

Sakamoto et al. (2003) "Interleukin-1 0 gene therapy enhances antitumor effect of CPT-11 for lung metastasis of colon26 adenocarcinoma in mice," *Gastroenterology*; 124( 4) :A456-A45 7.

Sawaya et al. (2003) "Risk of cervical cancer associated with extending the interval between cervical-cancer screenings," *New Engl J Med*; 349:1501-1509.

Schaffner et al. (2001) "Cosecretion of Chaperones and Low-Molecular-Size Medium Additives Increases the Yield of Recombinant Disulfide-Bridged Proteins," *Applied and Environmental Microbioloav*; 67(9):3994-4000.

Schneiderheinze, J., et al., (2009) "Rapid online proteolytic mapping of PEGylated rhGH for identity confirmation. quantitation of methionine oxidation and quantitation of UnPEGylated N-terminus using HPLC with UV detection", Journal of Chromatography B: Biomedical Sciences & Applications. Elsevier. Amsterdam. NL., 877(31):4065-4070.

Shen et al. (2013) "Proprotein convertase subtilisin/kexin type 9 potentially influences cholesterol uptake in macrophages and reverse cholesterol transport," *FEBS Letters*; 587:1271-1274.

Smith et al. (1996) "Administration of interleukin-1 0 at the time of priming protects Corynesmitbacterium parvum-primed mice against LPS- and TNF-alpha-induced lethality." *Cellular Immunoloav* 173(2):207-214.

(56) References Cited

OTHER PUBLICATIONS

Sneller et al. (2011) "IL-15 administered by continuous infusion to rhesus macaques induces massive expansion of CD8 T effector memory population in peripheral blood," *Blood*• 118(26):6845-6848.
Soman et al. (2009) "MTS dye based colorimetric CTLL-2 cell proliferation assay for product release and stability monitoring of Interleukin-15: Assay qualification, standardization and statistical analysis"*J Immunol Methods*• 348(1-2):83-94.
Song et al. (2012) "CD27 costimulation augments the survival and antitumor activity of redirected human T cells in vivo," *Blood*; 119(3):696-706.
Srivastava et al. (2013) "Effects of interleukin-18 on natural killer cells: costimulation of activation through Fe receptors for immunoglobulin," *Cancer ImmunolImmunother*; 62(6):1 073-1082.
Steel, JC et al., (2012) "Interluekin-15 Biology and its Therapeutic Implications in Cancer", Trends in Pharmacological Sciences, 33(1):35-41.
Storici and Resnick (2006) "The delitto perfetto approach to in vivo site-directed mutagenesis and chromosome rearrangements with synthetic oligonucleotides in yeast," *Methods in Enzymology*; 409:329-345.
Sweredoski and Baldi (2009) "COBEpro: a novel system for predicting continuous B-cell epitopes," *Protein Eng Des Sel*; 22:113-120.
Syto et al. (1998) "Structural and biological stability of the human interleukin 10 homodimer," *Biochemistry*; 37(48):16943-16951.
Teng et al. (2015) "IL-12 and IL-23 cytokines: from discovery to targeted therapies for immune-mediated inflammatory diseases," *Nature Medicine*; 21 :719-729.
Teng et al. "Stable IL-10: A new therapeutic that promotes tumor immunity" Cancer Cell 2011 Cell Press USA, vol. 20, No. 6 , Dec. 13, 2011 (Dec. 13, 2011) , pp. 691-693.
Tilg et al. (2002) "Treatment of Crohn's disease with recombinant human interleukin 10 induces the proinflammatory cytokine interferon y," *Gut*; 50:191-195.
Trandem et al. (2011) "Virally Expressed Interleukin-1 0 Ameliorates Acute Encephalomyelitis and Chronic Demyelination in Coronavirus-Infected Mice," *J. Viral.*; 85(14):6822-6831.
Trehin et al. (2004) "Cellular uptake but low permeation of human calcitonin-derived cell penetrating peptides and Tat(47-57) through well-differentiated epithelial models," *Pharm. Research* 21:1248-1256.
Tsumoto et al. (2003) "Practical considerations in refolding proteins from inclusion bodies," *Protein Expression and Purification*; 28:1-8.
Tsumoto et al. (2004) "Role of Arginine in Protein Refolding, Solubilization, and Purification," *Biotechnol. Prog.*; 20:1301-1308.
Valabrega et al. (2007) "Trastuzumab: mechanism of action, resistance and future perspectives in HER2-overexpressing breast cancer," *Annals of Oncology*; 18:977-984.
Van Deventer et al. (1997) "Multiple Doses of Intravenous Interleukin 10 in Steroid-Refractory Crohn's Disease," *Gastroenterology*, 113:383-389.
Vicari and Trinchieri (2004) "Interleukin-1 0 in viral diseases and cancer: exiting the labyrinth?," *Immunological Reviews*; 202:223-236.
Vigneron et al. (2013) "Database of T cell-defined human tumor antigens: the 2013 update," *Cancer Immunity*; 13:15-20.
Virgin, et al. (2009) "Redefining Chronic Viral Infection," *Cell*; 138:30-50.
Von Andrian and Mackay (2000) "T-cell function and migration. Two sides of the same coin," *New Engl J Med*; 343:1020-1034.
Waldmann et al. (2011) "Safety (toxicity), pharmacokinetics, immunogenicity, and impact on elements of the normal immune system of recombinant human IL-15 in rhesus macaaues" *Blood*• 117:4787-4795.
Walter and Nagabhushan (1995) "Crystal structure of interleukin 1 0 reveals an interferon gamma-like fold," *Biochemistry*; (38):12118-12125.

Wee et al. (2010) "SVM-based prediction of linear B-cell epitopes using Bayes Feature Extraction," *BMC Genomics*; 11 (Supp 4):S21.
Wender et al. (2000) "The design, synthesis, and evaluation of molecules that enable or enhance cellular uptake: peptoid molecular transporters," *Proc. Nat/. Acad. Sci. USA*; 97:13003-13008.
Wilson et al. (2011) "The role of IL-1 0 in regulating immunity to persistent viral infections," *Curr Top MicrobiolImmunol.*; 350: 39-65.
Witsch et al. (2010) "Roles for Growth Facotes in Cancer Progression," *Physiology*; 25(2):85-1 01.
Wu et al. (2012) "Immunotherapies: The Blockade of Inhibitory Signals," *Int. J. Bioi. Sci.*; 8:1420-1430.
Xu et al. (2010) "Regulation of Antitumor Immune Responses by the IL-12 Family Cytokines, IL-12, IL-23, and IL-27," *Clinical and Developmental Immunology*; Article ID:832454 (9 pages).
Yamaguchi and Miyazaki (2014) "Refolding Techniques for Recovering Biologically Active Recombinant Proteins from Inclusion Bodies," *Biomolecu/es*; 4:235-251.
Yoshioka et al. (2011) "Development of a novel DDS for site-specific PEGylated proteins," *Chern. Central J.*; 5:25.
Younes et al. (2004) "Phase II Clinical Trial of Interleukin-12 in Patients with Relapsed and Refractory Non-Hodgkin's Lymphoma and Hodgkin's Disease," *Clinical Cancer Research*10:5432-5438.
Zauner et al. (1996) "Glycerol Enhancement of Ligand-Polylysine/ DNA Transfection," *Bio Techniques*; 20:905-913.
Zdanov et al. (1995) "Crystal structure of interleukin-1 0 reveals the functional dimer with an unexpected topological similarity to interferon y ," *Structure*; 3:591-601.
Zdanov et al. (1996) "Crystal structure of human interleukin-1 0 at 1.6 A resolution and a model of a complex with its soluble receptor," *Protein Sci.*; (1 0):1955-1962.
Zender et al. (2002) "VP22-mediated intercellular transport of p53 in hepatoma cells in vitro and in vivo," *Cancer Gene Ther.*; 9(6):489-496.
Zheng et al. (1996) "Interleukin-10 inhibits tumor metastasis through an NK celldependent mechanism," *J Exp Med*; 184:579-584.
Aukrust et al., (2005) "Potential role for immunomodulatory therapy in atherosclerotic plaque stabilization", Expert Opinion Pharmacother, 6:2169-2180.
Bork, Peer, (2000) "Powers and Pitfalls in Sequence Analysis: The 70% Hurdle", Genome Research, 10:398-400.
Bowie, James, U., et al. (1990) "Deciphering the Message in Protein Sequences: Tolerance to Amino Acid Substitutions", Science, 247:1306-1310.
Burgess, Wilson, H., et al. (1990) "Possible Dissociation of the Heparin-binding and Mitogenic Activities of Heparin-Sinding (Acidic Fibroblast) Growth Factor-1 from Its Receptor-binding Activities by Site-directed Mutagenesis of a Single Lysine Residue", J. Cell Bioi., 111:2129-2138.
Cheon, H.G. (2013) "Latest research and development trends in non insulin anti-diabetics", Arch. Pharm. Res., 36:145-153.
Fichtlscherer et al., (2004) "Interleukin-10 serum levels and systemic endothelial vasoreactivity in patients with coronary artery desease", J. Am. Coll. Cardiol., 44:44-49.
Gabriel, A., (2007) "Changes in plasma cholesterol in mood disorder patients: Does treatment make a difference?", Journal of Affective Disorders, 99:273-278.
Lazar, Eliane, et al. (1988) "Transforming Growth Factor alpha: Mutation of Aspartic Acid 47 and Leucine 48 Results in Different Biological Activities", Mol. Cell. Bioi., 8:1247-1252.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Dec. 11, 2013, 3 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Jan. 31, 2014, 3 pages.
NCT02009449, "A Phase 1, OpenLabel Dose Escalation FirstinHuman Study to Evaluate the Tolerability, Safety, Maximum Tolerated

(56) References Cited

OTHER PUBLICATIONS

Dose, Preliminary Clinical Activity and Pharmacokinetics of AM0010 in Patients With Advanced Solid Tumors", ClinicalTrials.gov, Jul. 17, 2014, 6 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Mar. 24, 2015, 7 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Jan. 12, 2016, 7 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Oct. 2, 2016, 7 pages.

NCT02923921, "Randomized Study of AM0010 in Combination With FOLFOX Compared to FOLFOX Alone as Secondline Tx in Pts With Meta Pancreatic Cancer That Has Progressed During or Following a FirstLine Gemcitabine containing Regimen", ClinicalTrials.gov, Oct. 4, 2016, 3 pages.

Papadopoulou, Athanassia, et al., (2013) "Plasma total cholesterol in psychiatric patients after a suicide attempt and in follow-up", Journal of Affective Disorders, 148:440-443.

Pjrek, Edda, et al., (2007) "Serum lipid levels in seasonal affective disorder", Eur Arch Psychiatry Clin Neurosci, 257:197-202.

Soderquist, et al. (2010) "PEGylation of interleukin-10 for the mitigation of enhanced pain states", J Biomed Mater Res A, 3(93):1169-1179.

UniProt reference P79338 (1L 1 O_MACFA) (downloaded from http://www.uniprot.org/uniprot/P79338, last sequence Update May 1, 1997).

UniProt reference A2T6Z6 (1L 1 O_PANTR) (downloaded from http://www.uniprot.org/uniprot!A2T6Z6, last sequence update Mar. 6, 2007).

Virkkunen, M., (1979) "Serum Cholesterol in Antisocial Personality", Neuropsychobiology, 5:27-30.

Extended European search report for European Patent Application No. 15850904.2, dated May 30, 2010.

\* cited by examiner

FIGS. 1A-1C

1A. IL-15 Long Signal Peptide (LSP) Protein (accession no. BC018149.2) (SEQ ID NO:1)

MRISKPHLRSISIQCYLCLLLNSHFLTEAGIHVFILGCFSAGLPKTEANWVNVISDLKKIEDLIQSM
HIDATLYTESDVHPSCKVTAMKCFLLELQVISLESGDASIHDTVENLIILANNSLSSNGNVTESGC
KECEELEEKNIKEFLQSFVHIVQMFINTS

1B. IL-15 Short Signal peptide (SSP) Protein (accession no. BC100962.1) (SEQ ID NO:2)

MVLGTIDLCSCFSAGLPKTEANWVNVISDLKKIEDLIQSMHIDATLYTESDVHPSCKVTAMKCFL
LELQVISLESGDASIHDTVENLIILANNSLSSNGNVTESGCKECEELEEKNIKEFLQSFVHIVQMFI
NTS

1C. Mature human IL-15 Protein (SEQ ID NO:3)

NWVNVISDLKKIEDLIQSMHIDATLYTESDVHPSCKVTAMKCFLLELQVISLESGDASIHDTVEN
LIILANNSLSSNGNVTESGCKECEELEEKNIKEFLQSFVHIVQMFINTS

FIGS. 2A-C

2A. Long Signal Peptide (LSP) cDNA Open Reading Frame (ORF) (accession no. BC018149.2) (SEQ ID NO:4)

atgagaatttcgaaaccacatttgagaagtatttccatccagtgctacttgtgttacttctaaacagtcatttctaactgaagctggcattcatgtcttcatttg
ggctgtttcagtgcagggcttcctaaaacagaagccaactgggtgaatgtaataagtgatttgaaaaaaattgaagatcttattcaatctatgcatattgatg
ctactttatatacggaaagtgatgttcaccccagttgcaaagtaacagcaatgaagtgctttctcttggagttacaagttatttcacttgagtccggagatgca
agtattcatgatacagtagaaaatctgatcatcctagcaaacaacagtttgtcttctaatgggaatgtaacagaatctggatgcaaagaatgtgaggaactg
gaggaaaaaaatattaaagaattttttgcagagttttgtacatattgtccaaatgttcatcaacacttcttga

2B. Short Signal peptide (SSP) cDNA Open Reading Frame (ORF) (accession no. BC100962.1) (SEQ ID NO:5)

atggtattgggaaccatagatttgtgcagctgtttcagtgcagggcttcctaaaacagaagccaactgggtgaatgtaataagtgatttgaaa
aaaattgaagatcttattcaatctatgcatattgatgctactttatatacggaaagtgatgttcaccccagttgcaaagtaacagcaatgaagtg
ctttctcttggagttacaagttatttcacttgagtccggagatgcaagtattcatgatacagtagaaaatctgatcatcctagcaaacaacagttt
gtcttctaatgggaatgtaacagaatctggatgcaaagaatgtgaggaactggaggaaaaaaatattaaagaattttttgcagagttttgtacat
attgtccaaatgttcatcaacacttcttga

2C. Nucleic acid sequence encoding Mature Human IL-15 Protein (SEQ ID NO:6)

aactgggtgaatgtaataagtgatttgaaaaaaattgaagatcttattcaatctatgcatattgatgctactttatatacggaaagtgatgttcaccccagttgc
aaagtaacagcaatgaagtgctttctcttggagttacaagttatttcacttgagtccggagatgcaagtattcatgatacagtagaaaatctgatcatcctagc
aaacaacagtttgtcttctaatgggaatgtaacagaatctggatgcaaagaatgtgaggaactggaggaaaaaaatattaaagaattttttgcagagttttgt
acatattgtccaaatgttcatcaacacttcttga

FIG. 3

| Structural Motif | Helix A | | | | | | | | | | | | | | | A/B Loop | | | | | | | | | | | | | | |
|---|---|---|---|---|---|---|---|---|---|---|---|---|---|---|---|---|---|---|---|---|---|---|---|---|---|---|---|---|---|---|
| Amino Acid | N | W | V | N | V | I | S | D | L | K | K | I | E | D | L | Q | S | M | H | I | D | A | T | L | Y | T | E | S | D |
| Residue # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |

| Structural Motif | Helix B | | | | | | | | | | | | | | | | | B/C Turn | | | Helix C | | | | | | | | | |
|---|---|---|---|---|---|---|---|---|---|---|---|---|---|---|---|---|---|---|---|---|---|---|---|---|---|---|---|---|---|---|
| Amino Acid | V | H | P | S | C | K | V | T | A | M | K | C | F | L | L | E | L | Q | V | I | S | L | E | S | G | D | A | S | I | H |
| Potential PEG site | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 |

| Structural Motif | Helix C | | | | | | | | | | | | | | | | | | | | C/D Loop | | | | | | | | | |
|---|---|---|---|---|---|---|---|---|---|---|---|---|---|---|---|---|---|---|---|---|---|---|---|---|---|---|---|---|---|---|
| Amino Acid | D | T | V | E | N | L | I | I | L | A | N | N | S | S | L | S | N | G | N | V | T | E | S | G | C | K | E | C | E | E |
| Potential PEG site | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 |

| Structural Motif | C/D Loop | | | | | | | | | Helix D | | | | | | | | | | | | | | |
|---|---|---|---|---|---|---|---|---|---|---|---|---|---|---|---|---|---|---|---|---|---|---|---|---|
| Amino Acid | L | E | E | K | N | I | K | E | F | L | Q | S | F | V | H | I | V | Q | M | F | I | N | T | S |
| Potential PEG site | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 |

SEQUENCE LISTING

<160> NUMBER OF SEQ ID NOS: 41

<210> SEQ ID NO 1
<211> LENGTH: 162
<212> TYPE: PRT
<213> ORGANISM: Homo sapiens

<400> SEQUENCE: 1

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
        50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu

```
            100                 105                 110
Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 2
<211> LENGTH: 135
<212> TYPE: PRT
<213> ORGANISM: Homo sapiens

<400> SEQUENCE: 2

Met Val Leu Gly Thr Ile Asp Leu Cys Ser Cys Phe Ser Ala Gly Leu
1               5                   10                  15

Pro Lys Thr Glu Ala Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser
    130                 135

<210> SEQ ID NO 3
<211> LENGTH: 114
<212> TYPE: PRT
<213> ORGANISM: Homo sapiens

<400> SEQUENCE: 3

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 4
<211> LENGTH: 489
<212> TYPE: DNA
<213> ORGANISM: Homo sapiens

<400> SEQUENCE: 4

```
atgagaattt cgaaaccaca tttgagaagt atttccatcc agtgctactt gtgtttactt      60
ctaaacagtc attttctaac tgaagctggc attcatgtct tcattttggg ctgtttcagt     120
gcagggcttc ctaaaacaga agccaactgg gtgaatgtaa taagtgattt gaaaaaaatt     180
gaagatctta ttcaatctat gcatattgat gctactttat atacggaaag tgatgttcac     240
cccagttgca agtaacagc aatgaagtgc tttctcttgg agttacaagt tatttcactt      300
gagtccggag atgcaagtat tcatgataca gtagaaaatc tgatcatcct agcaaacaac     360
agtttgtctt ctaatgggaa tgtaacagaa tctggatgca agaatgtga ggaactggag      420 gaaaaaaata ttaagaattt ttgcagagt tttgtacata ttgtccaaat gttcatcaac      480
acttcttga                                                             489
```

<210> SEQ ID NO 5
<211> LENGTH: 408
<212> TYPE: DNA
<213> ORGANISM: Homo sapiens

<400> SEQUENCE: 5

```
atggtattgg gaaccataga tttgtgcagc tgtttcagtg cagggcttcc taaaacagaa      60
gccaactggg tgaatgtaat aagtgatttg aaaaaaattg aagatcttat tcaatctatg     120
catattgatg ctactttata tacggaaagt gatgttcacc ccagttgcaa agtaacagca     180
atgaagtgct ttctcttgga gttacaagtt atttcacttg agtccggaga tgcaagtatt     240
catgatacag tagaaaatct gatcatccta gcaaacaaca gtttgtcttc taatgggaat     300
gtaacagaat ctggatgcaa agaatgtgag gaactggagg aaaaaaatat taagaatttt     360 tgcagagtt tgtacatat tgtccaaatg ttcatcaaca cttcttga                    408
```

<210> SEQ ID NO 6
<211> LENGTH: 345
<212> TYPE: DNA
<213> ORGANISM: Homo sapiens

<400> SEQUENCE: 6

```
aactgggtga atgtaataag tgatttgaaa aaaattgaag atcttattca atctatgcat      60
attgatgcta ctttatatac ggaaagtgat gttcaccca gttgcaaagt aacagcaatg      120
aagtgctttc tcttggagtt acaagttatt tcacttgagt ccggagatgc aagtattcat     180
gatacagtag aaaatctgat catcctagca acaacagtt tgtcttctaa tgggaatgta      240
acagaatctg gatgcaaaga atgtgaggaa ctggaggaaa aaatattaa gaatttttg       300 cagagttttg tacatattgt ccaaatgttc atcaacactt cttga                     345
```

<210> SEQ ID NO 7
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 7

Arg Arg Gln Arg Arg Thr Ser Lys Leu Met Lys Arg

<210> SEQ ID NO 8
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 8

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 9
<211> LENGTH: 33
<212> TYPE: PRT
<213> ORGANISM: Artificial sequence
<220> FEATURE:
<223> OTHER INFORMATION: Synthetic polypeptide

<400> SEQUENCE: 9

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 10
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 10

Arg Gln Ile Lys Ile Trp Phe Gln Asn Arg Arg Met Lys Trp Lys Lys
1               5                   10                  15

<210> SEQ ID NO 11
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 11

Tyr Gly Arg Lys Lys Arg Arg Gln Arg Arg Arg
1               5                   10

<210> SEQ ID NO 12
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 12

Arg Lys Lys Arg Arg Gln Arg Arg Arg
1               5

<210> SEQ ID NO 13
<211> LENGTH: 11
<212> TYPE: PRT

```
<213> ORGANISM: Artificial sequence
<220> FEATURE:
<223> OTHER INFORMATION: Synthetic polypeptide

<400> SEQUENCE: 13

Tyr Gly Arg Lys Lys Arg Arg Gln Arg Arg
1               5                   10

<210> SEQ ID NO 14
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 14

Arg Lys Lys Arg Arg Gln Arg Arg
1               5

<210> SEQ ID NO 15
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 15

Tyr Ala Arg Ala Ala Ala Arg Gln Ala Arg Ala
1               5                   10

<210> SEQ ID NO 16
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 16

Thr His Arg Leu Pro Arg Arg Arg Arg Arg
1               5                   10

<210> SEQ ID NO 17
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 17

Gly Gly Arg Arg Ala Arg Arg Arg Arg Arg
1               5                   10

<210> SEQ ID NO 18
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 18

Arg Gly Arg Arg
1

<210> SEQ ID NO 19
<211> LENGTH: 6
<212> TYPE: PRT
<213> ORGANISM: Artificial sequence
```

```
<220> FEATURE:
<223> OTHER INFORMATION: Synthetic polypeptide

<400> SEQUENCE: 19

Arg Lys Arg Lys Lys Arg
1               5

<210> SEQ ID NO 20
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 20

Arg Lys Lys Arg
1

<210> SEQ ID NO 21
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 21

Arg Arg Arg Lys Lys Arg
1               5

<210> SEQ ID NO 22
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (5)..(5)
<223> OTHER INFORMATION: Ser may be repeated n times, where n is an
      integer of at least one

<400> SEQUENCE: 22

Gly Ser Gly Gly Ser
1               5

<210> SEQ ID NO 23
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Ser may be repeated n times, where n is an
      integer of at least one.

<400> SEQUENCE: 23

Gly Gly Gly Ser
1

<210> SEQ ID NO 24
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
```

```
<222> LOCATION: (1)..(1)
<223> OTHER INFORMATION: Gly may be repeated m times, where m is an
      integer of at least one.
<220> FEATURE:
<221> NAME/KEY: MISC_FEATURE
<222> LOCATION: (1)..(5)
<223> OTHER INFORMATION: Positions 1-5 may be repeated n times, where n
      is an integer of at least one.
<220> FEATURE:
<221> NAME/KEY: MISC_FEATURE
<222> LOCATION: (2)..(2)
<223> OTHER INFORMATION: Ser may be repeated o times, where o is an
      integer of at least one.
<220> FEATURE:
<221> NAME/KEY: MISC_FEATURE
<222> LOCATION: (3)..(3)
<223> OTHER INFORMATION: Gly may be repeated m times, where m is an
      integer of at least one.
<220> FEATURE:
<221> NAME/KEY: MISC_FEATURE
<222> LOCATION: (4)..(4)
<223> OTHER INFORMATION: Ser may be repeated o times, where o is an
      integer of at least one.
<220> FEATURE:
<221> NAME/KEY: MISC_FEATURE
<222> LOCATION: (5)..(5)
<223> OTHER INFORMATION: Gly may be repeated m times, where m is an
      integer of at least one.

<400> SEQUENCE: 24

Gly Ser Gly Ser Gly
1               5

<210> SEQ ID NO 25
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(5)
<223> OTHER INFORMATION: Positions 1-5 may be repeated n times, where n
      is an integer of at least one.
<220> FEATURE:
<221> NAME/KEY: MISC_FEATURE
<222> LOCATION: (5)..(5)
<223> OTHER INFORMATION: Ser may be repeated m times, where m is an
      integer of at least one.

<400> SEQUENCE: 25

Gly Ser Gly Gly Ser
1               5

<210> SEQ ID NO 26
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(5)
<223> OTHER INFORMATION: Positions 1-5 may be repeated n times, where n
      is an integer of at least one.
<220> FEATURE:
<221> NAME/KEY: MISC_FEATURE
<222> LOCATION: (4)..(4)
<223> OTHER INFORMATION: Ser may be repeated m times, where m is an
      integer of at least one.

<400> SEQUENCE: 26

Gly Ser Gly Ser Gly
1               5
```

```
<210> SEQ ID NO 27
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(4)
<223> OTHER INFORMATION: Positions 1-4 may be repeated n times, where n
      is an integer of at least one.
<220> FEATURE:
<221> NAME/KEY: MISC_FEATURE
<222> LOCATION: (4)..(4)
<223> OTHER INFORMATION: Ser may be repeated m times, where m is an
      integer of at least one.

<400> SEQUENCE: 27

Gly Gly Gly Ser
1

<210> SEQ ID NO 28
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 28

Gly Gly Ser Gly
1

<210> SEQ ID NO 29
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 29

Gly Gly Ser Gly Gly
1               5

<210> SEQ ID NO 30
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 30

Gly Ser Gly Ser Gly
1               5

<210> SEQ ID NO 31
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 31

Gly Ser Gly Gly Gly
1               5

<210> SEQ ID NO 32
<211> LENGTH: 5
```

<212> TYPE: PRT
<213> ORGANISM: Artificial sequence
<220> FEATURE:
<223> OTHER INFORMATION: Synthetic polypeptide

<400> SEQUENCE: 32

Gly Gly Gly Ser Gly
1               5

<210> SEQ ID NO 33
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 33

Gly Ser Ser Ser Gly
1               5

<210> SEQ ID NO 34
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 34
tataggccca gccggccgcc gccaccatga gaatttcgaa accacatttg ag        52

<210> SEQ ID NO 35
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 35 tagggccc tcaagaagtg ttgatgaaca tttgg        35

<210> SEQ ID NO 36
<211> LENGTH: 48
<212> TYPE: PRT
<213> ORGANISM: Artificial sequence
<220> FEATURE:
<223> OTHER INFORMATION: Synthetic polypeptide

<400> SEQUENCE: 36

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

<210> SEQ ID NO 37
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 37

Asn Val Ile Ser Asp Leu Lys Lys Ile
1               5

```
<210> SEQ ID NO 38
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 38

Asp Thr Val Glu Asn Leu
1               5

<210> SEQ ID NO 39
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 39

His Ile Val Gln Met Phe Ile Asn
1               5

<210> SEQ ID NO 40
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 40

Met Lys Trp Val Thr Phe Ile Ser Leu Leu Phe Leu Phe Ser Ser Ala
1               5                   10                  15

Tyr Ser

<210> SEQ ID NO 41
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 41

Arg Gly Val Phe Arg Arg
1               5
```

# INTERLEUKIN-15 COMPOSITIONS AND USES THEREOF

CROSS-REFERENCE TO RELATED APPLICATION

This application claims priority benefit of U.S. provisional application Ser. No. 62/063,784, filed Oct. 14, 2014, which application is incorporated herein by reference in its entirety.

FIELD OF THE INVENTION

The present invention relates to, among other things, interleukin-15 muteins and other interleukin-15-related molecules, modifications of the foregoing, and associated uses thereof.

INTRODUCTION

Interleukin-15 (IL-15) is a cytokine involved in the stimulation of cytolytic activity, cytokine secretion, proliferation and survival of NK cells, CD8+ memory T-cells and naïve CD8+ cells (see Fehniger, et al., J Immunol 162:4511-20 (1999)). As a pleiotropic cytokine, it plays important roles in innate and adaptive immunity (see Lodolce, et al., Cytokine Growth Factor Rev 13(6):429-39 (December 2002)) and Alves, et al., Blood 102:2541-46 (2003)).

IL-15 is constitutively expressed by a large number of cell types, including macrophages, monocytes, dendritic cells and fibroblasts (Grabstein, et al., Science 264(5161):965-68 (May 1994)). Expression of IL-15 can be stimulated by, for example, cytokines (e.g., GM-CSF), double-stranded mRNA, unmethylated CpG oligonucleotides, lipopolysaccharide through Toll-like receptors, and interferons (e.g., IFN-γ), or after infection of, for example, monocytes with herpes virus, Mycobacterium tuberculosis and Candida albicans (Bamford, et al., J Immunol160(9):4418-26 (May 1998)).

IL-15 binds to a specific receptor complex on T-cells and NK cells. IL-15 and IL-15Rα are co-expressed on activated dendritic cells and on monocytes, and IL-15 functions in a complex with IL-15Rα (Bergamaschi, et al., J Biol Chem 283:4189-99 (2008)). IL-15/IL-15α bind as a heterodimer to two chains on T-cells and NK cells—IL-2Rβ (also referred to as IL-15Rβ; CD122) and γc (also referred to as IL-2RG; CD132; γ-c; common γ-chain) molecules. The β and γc chains are shared between IL-2 and IL-15 and are essential for the signaling of these cytokines (Giri et al., EMBO J. 13:2822-30 (1994) and Giri et al., EMBO J. 14:3654-3663 (1995)).

Consistent with the sharing of the IL-2/IL-15βγc receptor complex, IL-15 has been shown to mediate many functions similar to those of IL-2 in vitro. They share many biological activities and exhibit similar contributions to the survival of T lymphocytes (see Waldmann, et al., Annu Rev Immunol 17:19-49 (1999)). It is believed that the biological differences between IL-2 and IL-15 are likely due to, for example, their different production sites, their strength of association with membrane receptor proteins, termed IL-2α and IL-15Rα, respectively, and the regulation of these extra receptor molecules. IL-2 and IL-15 play a role in regulating the number of CD8+ memory cells.

Despite the fact that IL-15 has been implicated in a number of diseases, disorders and conditions, including, for example, certain viral disorders and cancerous conditions, no IL-15-related agent is currently commercially available. Thus, a safe and effective IL-15 agent would address a heretofore unmet medical need.

SUMMARY

The present disclosure relates to IL-15 compositions and uses thereof. The terms "IL-15", "IL-15 polypeptide(s)," "IL-15-agent(s)", "IL-15 molecule(s)" and the like are intended to be construed broadly and include, for example, human and non-human IL-15-related polypeptides, including homologs, variants (including muteins), and fragments thereof, as well as IL-15 polypeptides having, for example, a leader sequence (e.g., a signal peptide). Particular embodiments relate to modifications of the foregoing. In particular embodiments, the modification(s) improves at least one property or other characteristic (e.g., half-life or efficacy) of the peptides compared to unmodified versions of the peptides thereof. In certain embodiments, the modification(s) result in a decrease in bioactivity, provided that another characteristic(s) (e.g., a pharmacokinetic parameter such as half-life) is enhanced, resulting in a modified IL-15 molecule that is at least, and generally more, beneficial from a therapeutic perspective.

Further embodiments of the present disclosure pertain to methods and other technologies for identifying specific amino acid residues or domains of IL-15 that may be modified according to the methods described herein. Methods of using (e.g., in the treatment or prevention of a disorder or a symptom thereof), identifying and/or generating the peptides described herein are also aspects of the present disclosure. Other aspects include, for example, pharmaceutical compositions comprising the peptides.

Mature human IL-15 is a 114 amino acid monomeric polypeptide. Two transcripts have been reported, one with a 48 amino acid signal peptide (Long Signal Peptide; LSP) (FIG. 1A; SEQ ID NO:1), and the other with a 21 amino acid signal peptide (Short Signal Peptide; SSP) (FIG. 1B; SEQ ID NO:2), both of which produce the same mature protein (FIG. 1C; SEQ ID NO:3). As set forth herein, mature human IL-15 is described as comprising four helices (A-D) linked by three distinct amino acid segments (A/B Loop; B/C Turn; and C/D Loop). These amino acid segments are also referred to as an inter-helix junction or inter-helices junctions.

Amino acid residues and regions of the IL-15 helices and inter-helices junctions that can or cannot be mutated and/or modified are discussed hereafter. By way of example, amino acid residues and regions that are buried within the three-dimensional core of IL-15 or that are involved with receptor binding are generally not candidates for modification.

The present disclosure contemplates peptides comprising a substitution that would facilitate the attachment of a PEG or other moiety (e.g., a serum albumin) to at least one amino acid residue. Examples of such peptides are described in detail hereafter.

Methods are described herein for evaluating the immunogenicity of the IL-15 peptides described herein. In still further embodiments, a modified peptide has an improvement in at least one property (e.g., a physical property, including solubility, bioavailability, serum half-life, and circulation time). Such properties are described further hereafter. In particular embodiments of the present disclosure, a mutant IL-15 or a modified IL-15 peptide is less immunogenic (i.e., stimulates less of an immune response) than the corresponding unmodified IL-15 peptide. In other embodiments, a modified IL-15 peptide is immunogenic-neutral (i.e., immunogenicity is not altered in a therapeutically relevant way) than the corresponding unmodified IL-15 peptide.

The present disclosure contemplates peptides comprising the amino acid sequence of FIG. 1C (SEQ ID NO:3), wherein the peptides comprise at least one amino acid substitution, deletion or addition, and wherein the substitution(s), deletion(s) or addition(s) does not, for example, adversely affect solubility or immunogenicity. The present disclosure also contemplates peptides having at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO:3, wherein the peptides a) have at least one property (e.g., a physical property, including solubility, bioavailability, serum half-life, and circulation time) that is improved compared to the peptide of SEQ ID NO:3, and/or b) are not more immunogenic than the peptide of SEQ ID NO:3, and/or c) have a bioactivity at least equal to the bioactivity of the peptide of SEQ ID NO:3.

It will be apparent to the skilled artisan that utilization of different methodologies (e.g., different methods of quantifying the exact concentration of IL-15 and/or different methods of producing IL-15) may result in an IL-15 agent that is more or less active—either in apparent activity due to differences in calculating protein concentration or in actual activity. By leveraging their skill and experience, skilled artisans will be able to factor in these differences in determining the relative bioactivities of an IL-15 molecule versus hIL-15. In some embodiments, such IL-15 molecules have at least 60, at least 70, at least 80, at least 90, at least 95, at least 100, at least 101, at least 102, at least 103, at least 104, at least 105, at least 106, at least 107, at least 108, at least 109, at least 110, at least 111, at least 112, or at least 113 amino acid residues.

In some embodiments, the amino acid residue addition(s), deletion(s), or substitution(s) of the aforementioned peptides does not disrupt the intramolecular disulfide bonds of the peptides. However, it should be noted that such an addition(s), deletion(s), or substitution(s) might possibly disrupt one or more of the intermolecular non-covalent bonds (e.g., hydrogen bonds), but that such disruption should not have a therapeutically relevant effect on protein function. According to the teachings of the present disclosure, in some particular embodiments an amino acid substitution may be a conservative substitution, and in other particular embodiments an amino acid substitution may be a non-conservative substitution.

In particular embodiments, the present disclosure contemplates peptides having a bioactivity at least equal to the bioactivity of SEQ ID NO:3. Bioactivity may be determined by any method known in the art, including a chemokine release assay, a TNFα production assay, a CTLL-2 cell proliferation assay, a M07e cell proliferation assay, or a T-cell IFNγ secretion assay. The T-cell screening can be performed using CD4+ cells, CD8+ cells, or NK cells. The skilled artisan is familiar with such assays, and exemplary protocols for several of them are described herein. Likewise, the immunogenicity of the peptides may be predicted or determined by any method known to the skilled artisan, including prediction by screening for at least one of T-cell epitopes or B-cell epitopes. In one aspect, immunogenicity is predicted by an in silico system and/or in an ex vivo assay system.

The instant disclosure also contemplates peptides comprising the amino acid sequence of SEQ ID NO:3, wherein the peptides comprise at least one amino acid substitution of a surface-exposed amino acid residue, and wherein the substitution does not adversely affect bioactivity, immunogenicity and/or another property or characteristic. In certain embodiments, these peptides also do not comprise substitution of any amino acid residues involved with receptor binding. However, it is to be understood that substitution, deletion, and/or addition of one or more amino acid residues within the IL-15 receptor binding region, or in close proximity thereto, that may be tolerated are contemplated by the present disclosure.

As described in detail elsewhere herein and depicted in FIG. 3, mature hIL-15 comprises a) a Helix A (amino acid residues 1-17); b) an A/B Inter-helix Junction (A/B Loop) (amino acid residues 18-31); c) a Helix B (amino acid residues 32-53); d) a B/C Inter-helix Junction (B/C Turn) (amino acid residues 54-57); e) a Helix C (amino acid residues 58-77); f) a C/D Inter-helix Junction (C/D Loop) (amino acid residues 78-96); and g) a Helix D (amino acid residues 97-114). In some embodiments, the present disclosure contemplates peptides comprising a) a Helix A; b) an A/B Inter-helix Junction; c) a Helix B; d) a B/C Inter-helix Junction; e) a Helix C; f) a C/D Inter-helix Junction; and g) a Helix D; wherein such peptides further comprise at least one of: i) substitution of at least one amino acid residue of Helix A other than amino acid residues 2 (W), 4-12 (NVIS-DLKKI; SEQ ID NO:37)), or 16 (I); or ii) substitution of at least one amino acid residue of the A/B Inter-helix Junction other than amino acid residues 30 (D) or 31 (V); or iii) substitution of at least one amino acid residue of Helix B other than amino acid residues 32 (H), 35 (C), 40 (M), 42-44 (CFL), 47 (L) or 50 (I); or iv) substitution of at least one amino acid residue of the B/C Inter-helix Junction; or v) substitution of at least one amino acid residue of Helix C other than amino acid residues 59 (I), 61-66 (DTVENL; SEQ ID NO:38), or 68-70 (ILA); or vi) substitution of at least one amino acid residue of the C/D Inter-helix Junction other than amino acid residues 85 (C) or 88 (C); or vii) substitution of at least one amino acid residue of Helix D other than amino acid residues 99 (F), 100 (L), 103 (F), or 105-112 (HIVQMFIN; SEQ ID NO:39).

Referring to the peptides described in the preceding paragraph, in particular embodiments the present disclosure contemplates peptides wherein the at least one amino acid substitution is in at least one of the following regions: 13-15, 17-29, 36-39, 51-58, 71-84, or 89-98. In other embodiments, the at least one amino acid substitution is in at least one of the following regions: 17-28, 36-38, 51-57, 71-84, or 89-98. In still further embodiments, the at least one amino acid substitution is at least at one of the following positions: 1, 3, 13-15, 17-29, 33, 34, 36-39, 41, 45, 46, 48, 49, 51-58, 60, 67, 71-84, 86, 87, 89-98, 101, 102, 104, 113, or 114. In certain embodiments, the at least one amino acid substitution is at least at one of the following positions: 1, 17-28, 36-38, 41, 45, 46, 48, 49, 51-57, 60, 67, 71-84, 86, 87, 89-98, 101, 113, or 114.

Using a systematic approach, the residues identified above were substituted in order to introduce amino acids capable of providing an anchor for a PEG and/or other modifications. In particular embodiments of the present disclosure, a cysteine, a tyrosine, and an N-glycosylation site (N-X-S and N-X-T motifs) were substituted for each of the residues previously identified as being candidates for such substitution. The results, described in detail hereafter and summarized in FIG. 6, provide the skilled artisan with specific guidance regarding the generation of advantageous IL-15 muteins.

Particular embodiments of the present disclosure contemplate modification(s) of the peptides described herein, wherein the modification(s) does not alter the amino acid sequence of the peptides (i.e., no amino acid substitutions, additions or deletions are introduced into the IL-15 primary amino acid sequence), and wherein the modification(s) improves or otherwise enhances at least one property or other characteristic (e.g., a pharmacokinetic parameter or efficacy) of the peptides compared to unmodified versions of the peptides.

The present disclosure contemplates the introduction of any modification that may be advantageous. Thus, in particular embodiments, the modification improves at least one physical property of the peptide (e.g., solubility, bioavailability, serum half-life, and circulation time). Other modifications include introducing means for blocking receptor cleavage and increasing affinity for the IL-15 receptor(s) (or modifying the off-rate so that the IL-15 molecule will be docked with the receptor(s) for a longer duration). In still further embodiments, modification of the IL-15 peptides does not cause a detrimental effect on immunogenicity of a level that is therapeutically relevant, and in still further embodiments the modified IL-15 is less immunogenic than unmodified IL-15.

In some embodiments, the modification is pegylation and the modified peptide is PEG-IL-15. The pegylated peptides may comprise at least one PEG molecule covalently attached to at least one amino acid residue of IL-15 (e.g., N-terminal or C-terminal pegylation).

The PEG molecule may be conjugated to IL-15 through a linker; linkers are described in detail hereafter. In some embodiments, two or more different sites on IL-15 may be modified (e.g., pegylated) by introducing more than one mutation and then modifying each of them. In further embodiments, the N-terminus may be modified (e.g., pegylated) in combination with the introduction of one or more mutations, and the modification (e.g., pegylation) thereof, elsewhere within the IL-15 protein. In still further embodiments, the C-terminus may be modified (e.g., pegylated) in combination with the introduction of one or more mutations, and the modification (e.g., pegylation) thereof, elsewhere within the IL-15 protein. Tyrosine 26 of IL-15 might be modified (e.g., pegylated) in combination with pegylation of the N-terminus. In additional embodiments, an IL-15 peptide may comprise a modification (e.g., pegylation) at the N-terminus and the C-terminus. Exemplary pegylation conditions are described herein. In further embodiments, the N-terminus may be modified (e.g., pegylated) in combination with the introduction of one or more mutations, and the modification (e.g., pegylation) thereof, elsewhere within the IL-15 protein. The PEG component may be any PEG tolerated by the peptides. Because of the relatively small size of IL-15, the molecular mass of the PEG is larger than that used for many other protein therapeutics. By way of example, the PEG component of the modified peptide has a molecular mass from 5 kDa to 20 kD in some embodiments, a molecular mass greater than 20 kDa in other embodiments, a molecular mass greater than 25 kDa in certain embodiments, a molecular mass greater than 30 kDa in still other embodiments, a molecular mass greater than 35 kDa in further embodiments, or a molecular mass of at least 40 kD in still other embodiments. In particular embodiments, the PEG has a molecular mass between 20 and 40 kDa. PEGs having other molecular mass values are described herein.

The present disclosure contemplates any modification to the peptides that imparts a desired property, including improvement (e.g., masking) of a property of the unmodified peptides. In some embodiments the modified peptides comprise an Fc fusion molecule; a serum albumin (e.g., HSA or BSA), which may be in the form of an HSA fusion molecule or an albumin conjugate; or an albumin binding domain. The modified peptides may be glycosylated or hesylated. Detailed descriptions of the foregoing are described elsewhere within the present disclosure.

In particular embodiments, the modification is site-specific. In further embodiments, the modification comprises a linker. Some modified IL-15 molecules may comprise more than one type of modification. The types of modifications and the methods of introducing such modifications to the IL-15 peptides described herein are not limiting, and the skilled artisan can envisage other such modifications and methods.

The peptides described herein may be produced recombinantly. The present disclosure contemplates nucleic acid molecules encoding the peptides, wherein the nucleic acid molecules may be operably linked to an expression control element that confers expression of the nucleic acid molecule encoding the peptide in vitro, in a cell or in vivo. Vectors (e.g., a viral vector) may comprise such nucleic acid molecules. Further embodiments entail transformed or host cells that express the peptides described herein.

The present disclosure also contemplates the use of gene therapy in conjunction with the teachings herein. For gene therapy uses and methods, a cell in a subject can be transformed with a nucleic acid that encodes an IL-15-related polypeptide as set forth herein in vivo. Alternatively, a cell can be transformed in vitro with a transgene or polynucleotide, and then transplanted into a tissue of a subject in order to effect treatment. In addition, a primary cell isolate or an established cell line can be transformed with a transgene or polynucleotide that encodes an IL-15-related polypeptide, and then optionally transplanted into a tissue of a subject.

A peptide of the present disclosure may comprise at least one unique epitope produced by the introduction of at least one mutation, as described herein. In some embodiments, the at least one unique epitope binds (specifically or non-specifically) to an antibody (e.g., an agonistic antibody). In further embodiments, the effect of an antibody (e.g., an agonistic antibody) mimics IL-15 activation through an IL-15 receptor.

The antibody may be monoclonal or polyclonal, and may be, for example, human or humanized. Embodiments include an antibody that comprises a light chain variable region and a heavy chain variable region present in separate polypeptides or in a single polypeptide, or an antibody that comprises a heavy chain constant region that is, e.g., an IgG1, IgG2, IgG3, or IgG4 isotype. The antibody may be, for example, a Fv, scFv, Fab, F(ab')2, or Fab' antibody, or it may be a single chain Fv (scFv) antibody (which may be multimerized).

In further embodiments, an antibody of the present disclosure binds the peptides with an affinity of from about 10E7 M-1 to about 10E12 M-1. An antibody may comprise a covalently linked moiety selected from a lipid moiety, a fatty acid moiety, a polysaccharide moiety, and a carbohydrate moiety. Embodiments are also contemplated wherein an antibody comprises an affinity domain, may be immobilized on a solid support, comprises a covalently linked non-peptide polymer (e.g., a poly(ethylene) glycol polymer) or is detectably labeled.

The present disclosure includes pharmaceutical compositions comprising the peptides or antibodies described herein, and a pharmaceutically acceptable diluent, carrier or excipient. In some embodiments, the excipient is an isotonic injection solution. The pharmaceutical compositions may be suitable for administration to a subject (e.g., a human), and may comprise one or more additional prophylactic or therapeutic agents. In certain embodiments, the pharmaceutical compositions are contained in a sterile container (e.g., a single- or multi-use vial or a syringe). A kit may contain the sterile container(s), and the kit may also contain one or more additional sterile containers comprising at least one additional prophylactic or therapeutic agent or any other agent that may be used in pharmacological therapy. Examples of such aspects are set forth herein.

Additional embodiments of the present disclosure comprise a method of treating or preventing a disease, disorder or condition in a subject (e.g., a human), comprising administering a therapeutically effective amount of a peptide described herein. Further embodiments comprise a method of treating or preventing a disease, disorder or condition in a subject, comprising administering a therapeutically effective amount of an antibody described herein. In various embodiments of the present disclosure, the disease, disorder or condition is a proliferative disorder, including a cancer or a cancer-related disorder (e.g., a solid tumor or a hematological disorder); an immune or inflammatory disorder (e.g., inflammatory bowel disease, psoriasis, rheumatoid arthritis, sarcoidosis, multiple sclerosis, and Alzheimer's disease); a viral disorder (e.g., human immunodeficiency virus, hepatitis B virus, hepatitis C virus and cytomegalovirus).

In the methods of treating or preventing a disease, disorder or condition, administration of the therapeutically effective amount of a peptide (or an antibody) described herein may be by any route appropriate for the peptide (or antibody), including parenteral injection (e.g., subcutaneously). One or more additional prophylactic or therapeutic agents may be administered with (e.g., prior to, simultaneously with, or subsequent to) the peptide (or antibody), and/or it may be administered separate from or combined with the peptide (or antibody).

Additional embodiments of the present disclosure comprise the amino acid sequence of SEQ ID NO:3, wherein the peptide comprises at least one amino acid substitution at one of the following positions: 1, 3, 13-15, 17-29, 33, 34, 36-39, 41, 45, 48, 49, 51-58, 60, 67, 71-84, 86, 87, 89-98, 101, 102, 104, 113, or 114. In some of the embodiments, the peptide comprises substitution of a tyrosine for at least one of the amino acid residues at the following positions: 1, 3, 13-15, 17-25, 27-29, 33, 34, 36-39, 41, 45, 48, 49, 51-58, 60, 67, 71-84, 86, 87, 89-98, 101, 102, 104, 113, or 114. In other embodiments, the peptide comprises substitution of a cysteine for at least one of the amino acid residues at the following positions: 1, 3, 13-15, 17-25, 27-29, 33, 34, 36-39, 45, 48, 49, 51-56, 58, 60, 67, 72-84, 86, 87, 89-98, 101, 102, 104, 113, or 114. In further embodiments, the peptide comprises substitution of an N-X-S glycosylation motif for at least one of the amino acid residues at the following positions: 1, 13-15, 17-22, 27-29, 34, 36, 48, 49, 51-58, 60, 72-82, 84, 87, 89-98, 102, or 104, wherein the asparagine of the N-X-S glycosylation motif represents the amino acid position. In still further embodiments, the peptide comprises substitution of an N-X-T glycosylation motif for at least one of the amino acid residues at the following positions: 1, 13-15, 17-22, 29, 34, 36, 48, 49, 51-58, 60, 71-78, 80-82, 84, 87, 89-98, or 102, wherein the asparagine of the N-X-T glycosylation motif represents the amino acid position.

The present disclosure contemplates the peptides described in the preceding paragraph to be used with, as components of, etc., all of the embodiments disclosed herein. By way of example, in particular embodiments, the present disclosure contemplates pharmaceutical compositions, sterile containers, and kits comprising a peptide described in the preceding paragraph. In other embodiments, a therapeutically effective amount of a peptide described in the preceding paragraph may be administered to a subject to treat or prevent a disease, disorder or condition, as described herein.

Other aspects of the present disclosure will be apparent to the skilled artisan upon review of the teachings set forth herein.

BRIEF DESCRIPTION OF THE DRAWINGS

FIG. 1A depicts the IL-15 Long Signal Peptide (LSP) Protein (162 amino acid residues; SEQ ID NO:1). The signal peptide (underlined) comprises residues 1-48.

FIG. 1B depicts the IL-15 Short Signal peptide (SSP) Protein (135 amino acid residues; SEQ ID NO:2). The signal peptide (underlined) comprises residues 1-21.

FIG. 1C depicts the mature human IL-15 protein (114 amino acid residues) (SEQ ID NO:3).

FIG. 2A depicts the Long Signal Peptide (LSP) cDNA Open Reading Frame (ORF) (489 base pairs (SEQ ID NO:4), encoding 162 amino acid residues). The signal peptide (underlined) comprises base pairs 1-144, encoding the first 48 amino acids.

FIG. 2B depicts the Short Signal peptide (SSP) cDNA Open Reading Frame (ORF) (408 base pairs (SEQ ID NO:5), encoding 135 amino acid residues). The signal peptide (underlined) comprises base pairs 1-63, encoding the first 21 amino acids.

FIG. 2C depicts the nucleic acid sequence encoding mature human IL-15 Protein (345 base pairs (SEQ ID NO:6), encoding 114 amino acid residues).

FIG. 3 depicts the mature human IL-15 amino acid sequence (SEQ ID NO:3) indicating the regions corresponding to Helices A-D, and the Inter-helices Junctions.

FIG. 5 depicts the mature human IL-15 amino acid sequence (SEQ ID NO:3) indicating which residues represent potential sites for pegylation. The "+" indicates that the residue is a potential site, the "−" indicates that the residue is not a potential site, and the "+/−" indicates that the residue may be a potential site.

FIGS. 6A-6B depict the mature human IL-15 amino acid sequence (SEQ ID NO:3) indicating which amino acid residues represent potential sites for pegylation by substitution with a tyrosine or a cysteine, or by the generation of an N-glycosylation motif (N-X-S or N-X-T). The light grey cells represent residues identified in FIG. 5 as being potential pegylation sites, and a "+" indicates that the mutant inserted at that location was active in an activity assay, while an empty light grey cell indicates that the mutant inserted at that location either did not exhibit activity or was not able to be expressed at detectable levels.

DETAILED DESCRIPTION

Figure 4A:
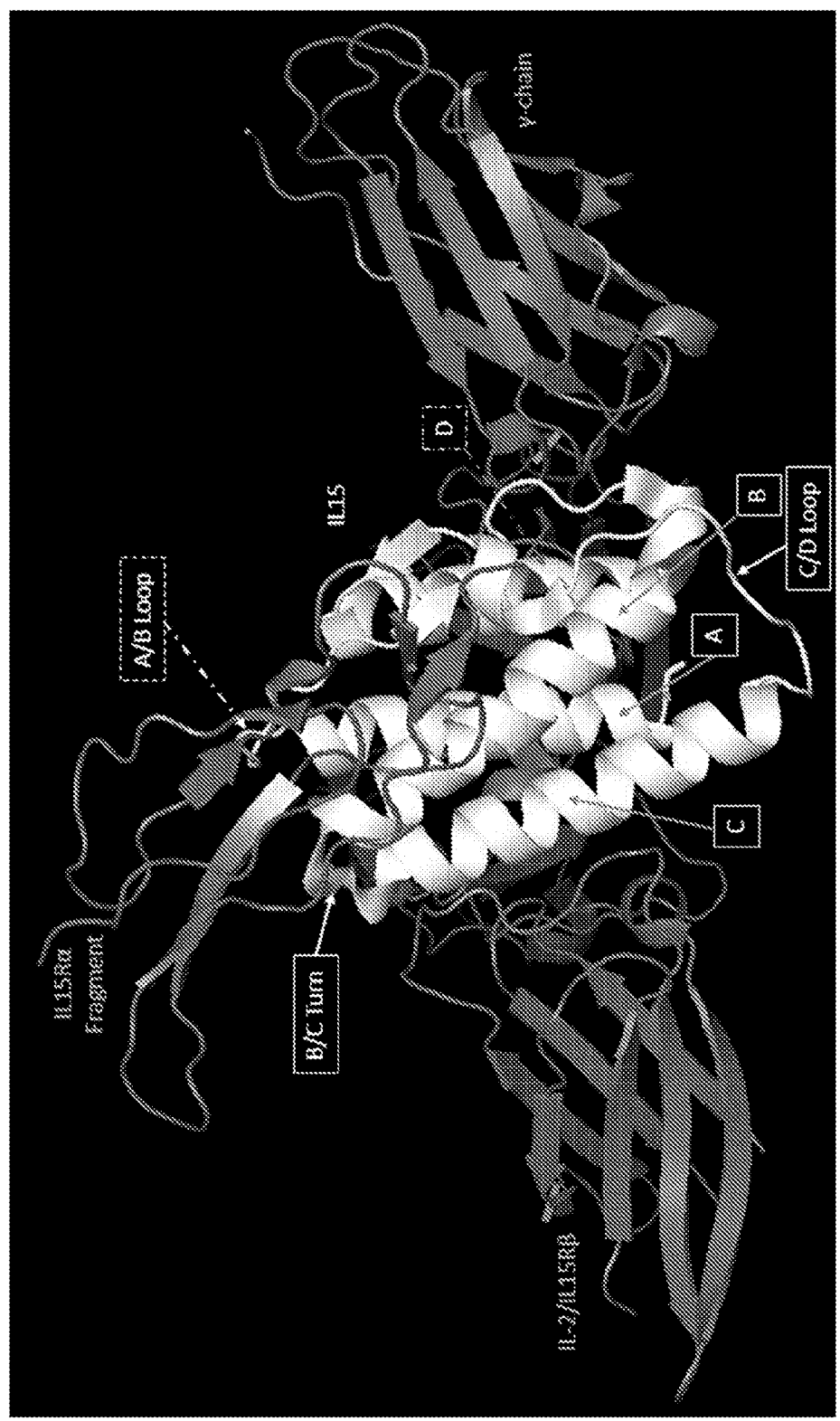
FIG. 4A is a protein crystal structure ribbon representation of the IL-15 Receptor Signaling Complex (PDB 4GS7); top view: IL2/15Rβ, IL15Rα, the common γ-chain, and IL-15 (Helices and intrahelical features are labeled).

Before the present disclosure is further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

Overview

The present disclosure contemplates mutant IL-15 molecules (e.g., muteins) and other IL-15-related molecules, as well as methods of their identification and their use. As described herein, the IL-15 molecules may be modified to, for example, enhance a property of native human IL-15, including half-life extension. Modifications include pegylation and fusions with albumin (e.g., HSA) and Fc. Particular IL-15 molecules have comparable immunogenicity to human IL-15, and/or bioactivity at least comparable to human IL-15, and/or an improvement in at least one property (e.g., a physical property, including solubility, bioavailability, serum half-life, and circulation time). The skilled artisan will recognize that such molecules may be viable therapeutics due to, e.g., a very long half-life. The IL-15 molecules described herein, and compositions (e.g., pharmaceutical compositions) thereof, may be used to treat and/or prevent various diseases, disorders and conditions, and/or the symptoms thereof, including, for example, inflammatory- and immune-related disorders, and cancer and cancer-related disorders.

It should be noted that any reference to "human" in connection with the polypeptides and nucleic acid molecules of the present disclosure is not meant to be limiting with respect to the manner in which the polypeptide or nucleic acid is obtained or the source, but rather is only with reference to the sequence as it may correspond to a sequence of a naturally occurring human polypeptide or nucleic acid molecule. In addition to the human polypeptides and the nucleic acid molecules which encode them, the present disclosure contemplates IL-15-related polypeptides and corresponding nucleic acid molecules from other species.

Definitions

Unless otherwise indicated, the following terms are intended to have the meaning set forth below. Other terms are defined elsewhere throughout the specification.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, IL-15 or PEG-IL-15), a nucleic acid (e.g., a nucleic acid encoding native human IL-15), a pharmaceutical composition comprising the foregoing, or a diagnostic agent; to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", "treatment" and the like refer to a course of action (such as administering IL-15 or a pharmaceutical composition comprising IL-15) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, or condition afflicting a subject. Thus, treatment includes inhibiting (e.g., arresting the development or further development of the disease, disorder or condition or clinical symptoms associated therewith) an active disease. The terms may also be used in other contexts, such as situations where IL-15 or PEG-IL-15 contacts an IL-15 receptor in, for example, the fluid phase or colloidal phase.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering IL-15 or a pharmaceutical composition comprising IL-15) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the amount of inflammatory cytokines produced following administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration of IL-15) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The term "ligand" refers to, for example, a peptide, a polypeptide, a membrane-associated or membrane-bound molecule, or a complex thereof, that can act as an agonist or antagonist of a receptor. "Ligand" encompasses natural and synthetic ligands, e.g., cytokines, cytokine variants, analogs, muteins, and binding compositions derived from antibodies, as well as, e.g., peptide mimetics of cytokines and peptide mimetics of antibodies. The term also encompasses an agent that is neither an agonist nor antagonist, but that can bind to a receptor without significantly influencing its biological properties, e.g., signaling or adhesion. Moreover, the term includes a membrane-bound ligand that has been changed, e.g., by chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex."

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of an IL-15 molecule (or the nucleic acid molecules encoding them), either directly or indirectly; or to enhance the ability of a molecule to produce an effect comparable to that of an IL-15 molecule. The term "modulator" is meant to refer broadly to molecules that can effect the activities described above. By way of example, a modulator of, e.g., a gene, a receptor, a ligand, or a cell, is a molecule that alters an activity of the gene, receptor, ligand, or cell, where activity can be activated, inhibited, or altered in its regulatory properties. A modulator may act alone, or it may use a cofactor, e.g., a protein, metal ion, or small molecule. The term "modulator" includes agents that operate through the same mechanism of action as IL-15 (i.e., agents that modulate the same signaling pathway as IL-15 in a manner analogous thereto) and are capable of eliciting a biological response comparable to (or greater than) that of IL-15.

Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of the molecules described above.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term may also refer to activity in modulating or maintaining cell-to-cell interactions (e.g., adhesion), or activity in maintaining a structure of a cell (e.g., a cell membrane). "Activity" can also mean specific activity, e.g., [catalytic activity]/[mg protein], or [immunological activity]/[mg protein], concentration in a biological compartment, or the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity. As previously indicated, the skilled artisan recognizes that use of different methodologies may result in IL-15 that is more or less active—either in apparent activity due to differences in calculating protein concentration or in actual activity—than a hIL-15 reference standard. The skilled artisan will be able to factor in these differences in determining the relative bioactivities of an IL-15 molecule versus hIL-15.

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

As used herein, the terms "variants" and "homologs" are used interchangeably to refer to amino acid or DNA sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring DNA sequences and proteins encoded thereby and their isoforms, as well as splice variants of a protein or gene. The terms also encompass nucleic acid sequences that vary in one or more bases from a naturally-occurring DNA sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes. Unless otherwise indicated, use of terms such as "mutant of IL-15" refer to IL-15 muteins.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

It will be appreciated that throughout this disclosure reference is made to amino acids according to the single letter or three letter codes. For the reader's convenience, the single and three letter amino acid codes are provided below:

| | | | | | |
|---|---|---|---|---|---|
| G | Glycine | Gly | P | Proline | Pro |
| A | Alanine | Ala | V | Valine | Val |
| L | Leucine | Leu | I | Isoleucine | Ile |
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

As used herein in reference to native human IL-15 or an IL-15 mutein, the terms "modified", "modification" and the like refer to one or more changes that enhance a desired property of human IL-15 or an IL-15 mutein. Such desired properties include, for example, prolonging the circulation half-life, increasing the stability, reducing the clearance, altering the immunogenicity or allergenicity, and enabling the raising of particular antibodies (e.g., by introduction of unique epitopes) for use in detection assays. As discussed in detail hereafter, modifications to human IL-15 or an IL-15 mutein that may be carried out include, but are not limited to, pegylation (covalent attachment of one or more molecules of polyethylene glycol (PEG), or derivatives thereof); glycosylation (e.g., N-glycosylation), polysialylation and hesylation; albumin fusion; albumin binding through, for example, a conjugated fatty acid chain (acylation); Fc-fusion; and fusion with a PEG mimetic. In some embodiments, linkers are used in such modifications and are described hereafter.

As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from", in the context of an amino acid sequence or polynucleotide sequence (e.g., an amino acid sequence "derived from" an IL-15 polypeptide), is meant to indicate that the polypeptide or nucleic acid has a sequence that is based on that of a reference polypeptide or nucleic acid (e.g., a naturally occurring IL-15 polypeptide or an IL-15-encoding nucleic acid), and is not meant to be limiting as to the source or method in which the protein or nucleic acid is made. By way of example, the term "derived from" includes homologs or variants of reference amino acid or DNA sequences.

In the context of a polypeptide, the term "isolated" refers to a polypeptide of interest that, if naturally occurring, is in an environment different from that in which it may naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was made by either synthetic or recombinant means.

"Enriched" means that a sample is non-naturally manipulated (e.g., by a scientist) so that a polypeptide of interest is present in a) a greater concentration (e.g., at least 3-fold greater, at least 4-fold greater, at least 8-fold greater, at least 64-fold greater, or more) than the concentration of the polypeptide in the starting sample, such as a biological sample (e.g., a sample in which the polypeptide naturally occurs or in which it is present after administration), or b) a concentration greater than the environment in which the polypeptide was made (e.g., as in a bacterial cell).

"Substantially pure" indicates that a component (e.g., a polypeptide) makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least 2-times greater, at least 10-times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

IL-15

IL-15, also referred to as MGC9721, is predicted to be 12.8 kDa monomeric glycoprotein encoded by the 34 kb region on chromosome 4q31. IL-15 belongs to the four α-helix bundle family, other members of which include IL-2, IL-4, IL-7, IL-9, granulocyte colony-stimulating factor (G-CSF), and granulocyte-macrophage colony-stimulating factor (GM-CSF). The genomic structure of human IL-15 contains 9 exons (1-8 and 4A) and eight introns. Humans and mice share a similar intron/exon structure. The overall intron/exon structure of the portion of the IL-15 gene encoding the mature protein is similar to that of the IL-2 gene and other 4 α-helix bundle cytokines.

Those of skill in the art will appreciate that IL-15 nucleic acid and amino acid sequences are publicly available in gene databases (e.g., GenBank). As depicted in FIG. 1C (SEQ ID NO:3), the mature human IL-15 protein comprises 114 amino acid residues (12.8 kDA). The recombinant human IL-15 produced in *E. coli* is a single, non-glycosylated polypeptide chain (115 amino acid residues, including an N-terminal methionine, having a molecular mass of 12.9 kD). Two transcripts have been reported, both reportedly producing the same mature protein. Referring to FIG. 1A (SEQ ID NO:1), the IL-15 Long Signal Peptide (LSP) Protein (accession no. BC018149.2) comprises 162 amino acid residues, including a 48 residue signal peptide (underlined). Referring to FIG. 1B (SEQ ID NO:2), the IL-15 Short Signal peptide (SSP) Protein (accession no. BC100962.1) comprises 135 amino acid residues, including a 21 residue signal peptide (underlined). The LSP has been described as a secreted protein, and the SSP has been described as remaining intracellular.

FIG. 2A depicts the Long Signal Peptide (LSP) cDNA ORF (489 base pairs (SEQ ID NO:4), encoding 162 amino acid residues) (accession no. BC018149.2); the signal peptide (underlined) comprises base pairs 1-144, encoding the first 48 amino acids. FIG. 2B depicts the Short Signal peptide (SSP) cDNA ORF (408 base pairs (SEQ ID NO:5), encoding 135 amino acid residues) (accession no. BC100962.1); the signal peptide (underlined) comprises base pairs 1-63, encoding the first 21 amino acids. FIG. 2C depicts the nucleic acid sequence encoding mature human IL-15 Protein (345 base pairs (SEQ ID NO:6), encoding 114 amino acid residues).

Non-human exemplified mammalian IL-15 nucleic acid or amino acid sequences can be from, for example, primate, canine, feline, porcine, equine, bovine, ovine, rodentia, murine, rat, hamster, and guinea pig. Accession numbers for exemplified non-human mammalian IL-15 nucleic acid sequences include U19843 (macaque); DQ021912 (macaque); AB000555 (macaque); NM_214390 (porcine); DQ152967 (ovine); NM_174090 (bovine); NM_008357 (murine); NM_013129 (*rattus*); DQ083522 (water buffalo); XM_844053 (canine); DQ157452 (lagomorpha); and NM_001009207 (feline). Accession numbers for exemplified non-human mammalian IL-15 amino acid sequences include AAB60398 (macaque); AAY45895 (macaque); NP_999555 (porcine); NP_776515 (bovine); AAY83832 (water buffalo); ABB02300 (ovine); XP_849146 (canine); NP_001009207 (feline); NP_037261 (*rattus*); and NP_032383 (murine). The identity of mature cynomolygous monkey IL-15 ("cIL-15") compared to human IL-15 ("hIL-15") is 96%, while the identity of mature mouse IL-15 ("mIL-15") and mature hIL-15 is 75%.

Human IL-15 contains two disulfide bonds at positions C42-C88 and C35-C85, the former being homologous to the C-C within IL-2. There are two N-linked glycosylation sites at N79 and N112 (depending on the analytical method used, N71 may be deemed to be a third glycosylation site). The mature IL-15 protein has been predicted to have strong helical moments at amino acid residues 1 to 15, 18 to 57, 65 to 78, and 97 to 114, supporting its 4 α-helix bundle structure (Fehniger, et al., Blood 97(1) (Jan. 1, 2001)).

As indicated previously, a nexus exists between IL-15 and IL-2. Based upon complex regulation and differential patterns of IL-15 and IL-15Rα expression, it is likely that the critical in vivo functions of this receptor/ligand pair differ from those of IL-2 and IL-2Rα. IL-15 exhibits several key non-redundant roles, including its importance during natural killer (NK) cell, NK-T cell, and intestinal intraepithelial lymphocyte development and function. As IL-15 reportedly plays a role in autoimmune processes (e.g., rheumatoid arthritis) and malignancies (e.g., T-cell leukemia), disruptions in normal IL-15 function has been implicated in untoward effects in subjects.

Though both signal through the receptor subunit IL-2Rβ and the common γ-chain (γ(c)), IL-15 and IL-2 do not share all of the same biological functions. In the structure of the IL-15-IL-15Rα-IL-2Rβ-γ(c) quaternary complex, IL-15 binds to IL-2Rβ and γ(c) in a heterodimer resembling that of the IL-2-IL-2Rα-IL-2Rβ-γ(c) complex. IL-15Rα has been shown to substantially increase the affinity of IL-15 for IL-2Rβ, which, in turn, is required for IL-15 trans-signaling. IL-15 and IL-2 induce similar signals, and the specificity of IL-2Rα versus IL-15Rα has been shown to determine cellular responsiveness. (See Ring et al., Nat. Immunol. 13(12):1187-95 (Dec. 13, 2012)).

IL-15 exists primarily as a membrane-bound form, although it also exists as a soluble molecule (Jakobisiak, et al., Cytokine Growth Factor Ref 22(2)99-109 (April 2011)), and it is associated with two distinct signaling mechanisms. The primary mechanism is trans-presentation which is mediated by membrane-bound complex IL-15/IL-15Rα. In this signaling mechanism, IL-15 binds to IL-15Rα receptor, with subsequent presentation to surrounding cells having the IL-15Rβγc complex on their cell surface. The second mechanism is cis-presentation, where IL-15 is presented by IL-15Rα to the 15Rβγc signaling complex on the same cell. Referring to the primary signaling mechanism, upon binding of IL-15 to the IL-15Rα receptor and subsequent presentation to surrounding cells bearing IL-15Rβγc complex, the IL-15β subunit activates Janus kinase 1 (Jak1) and the γc subunit activates Janus kinase 2 (Jak2), which leads to phosphorylation and activation of signal transducer and activator of transcription 3 (STAT3) and STAT5. Because IL-15 and IL-2 share receptor subunits, they have similar downstream effects, including the induction of B-cell lymphoma (Bcl-2); mitogen-activated protein kinase (MAP) pathway, and the phosphorylation of lymphocyte-activated protein tyrosine kinase (Lck) and spleen tyrosine kinase (Syk), which results in cell proliferation and maturation (Schluns, et al., Int J Biochem Cell Biol 37(8):1567-71 (August 2005)).

In contrast, the IL-15R signaling pathway in mast cells includes Jak2 and STAT5 instead Jak1/3 and STAT3/5. Phosphorylation STATs form transcription factors and activate transcription of appropriate genes. The β chain of IL-15R recruits and also activates protein tyrosine kinases of the Src family including Lck, Fyn and Lyn kinase. The β chain also activates phosphatidylinositol 3-kinase (PI3K) and AKT signaling pathways and induces expression of various transcription factors, including c-Fos, c-Jun, c-Myc and NF-κB (Jakobisiak, et al., Cytokine Growth Factor Ref 22(2)99-109 (April 2011)).

As previously indicated, the present disclosure also contemplates the use of gene therapy in vivo, in vitro, and ex vivo in conjunction with the teachings herein. Gene therapy is effected by delivering genetic material, usually packaged in a vector, to endogenous cells within a subject in order to introduce novel genes, to introduce additional copies of pre-existing genes, to impair the functioning of existing genes, or to repair existing but non-functioning genes. Once inside cells, the nucleic acid is expressed by the cell machinery, resulting in the production of the protein of interest. In the context of the present disclosure, gene therapy is used as a therapeutic to deliver nucleic acid that encodes an IL-15 agent for use in the treatment or prevention of a disease, disorder or condition described herein. As used herein, gene therapy also describes the removal of cells from a subject, transfecting the cells with a nucleic acid molecule encoding IL-15, and returning the cells to the subject.

As alluded to above, for gene therapy uses and methods, a cell in a subject can be transformed with a nucleic acid that encodes an IL-15-related polypeptide as set forth herein in vivo. Alternatively, a cell can be transformed in vitro with a transgene or polynucleotide, and then transplanted into a tissue of a subject in order to effect treatment. In addition, a primary cell isolate or an established cell line can be transformed with a transgene or polynucleotide that encodes an IL-15-related polypeptide, and then optionally transplanted into a tissue of a subject.

Pegylated IL-15

The utility of recombinant human IL-15 is frequently limited by its relatively short serum half-life, which may be due to, for example, renal clearance or proteolytic degradation. As a result, various approaches have been explored to improve the pharmacokinetic profile of IL-15 without adversely disrupting its structure and thus having an undesirable impact on activity. Pegylation of IL-15 results in improvement of certain pharmacokinetic parameters (e.g., serum half-life), as reported in, for example, CN102145178. However, CN102145178 focuses on N-terminal pegylation. A fusion molecule comprising IL-15 and Fc has also been reported to improve half-life (see, e.g., CN200410067182).

As will be apparent to the skilled artisan, more than one polyethylene glycol molecule may be attached to more than one amino acid residue. Thus, as used herein, the terms "pegylated IL-15" and "PEG-IL-15" refer to an IL-15 molecule having one or more polyethylene glycol molecules covalently attached to at least one amino acid residue of the IL-15 protein, generally via a linker, such that the attachment is stable. The terms "monopegylated IL-15" and "mono-PEG-IL-15" may be used to indicate that one polyethylene glycol molecule is covalently attached to a single amino acid residue of IL-15, generally via a linker. The terms "dipegylated IL-15" and "di-PEG-IL-15" may be used to describe an IL-15 protein wherein one polyethylene glycol molecule is covalently attached to one amino acid residue, and another polyethylene glycol molecule is covalently attached to a different amino acid residue. For example, one polyethylene glycol molecule may be covalently bound to the N-terminal amino acid residue of mature IL-15, and another polyethylene glycol molecule may be covalently bound to the C-terminal residue. It is also possible to generate a protein wherein a polyethylene molecule is covalently attached to more than two amino acid residues; one of ordinary skill in the art is familiar with means of producing such molecules.

In particular embodiments, the PEG-IL-15 used in the present disclosure is a mono-PEG-IL-15 in which one to nine PEG molecules are covalently attached via a linker to the alpha amino group of the amino acid residue at the N-terminus or the epsilon amino group on the side chain of lysine residues. Linkers are described further hereafter. In order to effect pegylation at sites within mature IL-15 that might not normally be amenable to pegylation, one or more different sites on IL-15 might be modified by introducing more than one mutation and then modifying (i.e., pegylating) each of them. Exemplary pegylation conditions are described elsewhere herein.

In particular embodiments, the average molecular weight of the PEG moiety is between about 5 kDa and about 50 kDa. For example, the PEG moiety may have a molecular mass greater than about 5 kDa, greater than about 10 kDa, greater than about 15 kDa, greater than about 20 kDa, greater than about 25 kDa, greater than about 30 kDa, greater than about 35 kDa, greater than about 40 kDa, greater than about 45 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa. In other embodiments, the molecular mass is from about 15 kDa to about 20 kDa, from about 15 kDa to about 25 kDa, from about 15 kDa to about 30 kDa, from about 15 kDa to about 35 kDa, from about 15 kDa to about 40 kDa, or from about 15 kDa to about 45 kDa.

Because of the size of IL-15, PEGs greater than 20 kDa (e.g., in the 20-40 kDa range) are contemplated in particular embodiments. In some embodiments, the molecular mass is from about 20 kDa to about 25 kDa, from about 20 kDa to about 30 kDa, from about 20 kDa to about 35 kDa, from about 20 kDa to about 40 kDa, from about 20 kDa to about 45 kDa, or from about 20 kDa to about 50 kDa. In some additional embodiments, the molecular mass is from about 25 kDa to about 30 kDa, from about 25 kDa to about 35 kDa, from about 25 kDa to about 40 kDa, from about 25 kDa to about 45 kDa, or from about 25 kDa to about 50 kDa. In still other embodiments, the molecular mass is from about 30 kDa to about 35 kDa, from about 30 kDa to about 40 kDa, from about 30 kDa to about 45 kDa, or from about 30 kDa to about 50 kDa. In still other embodiments, the molecular mass is from about 35 kDa to about 40 kDa, from about 35 kDa to about 45 kDa, from about 35 kDa to about 50 kDa, from about 40 kDa to about 45 kDa, from about 40 kDa to about 50 kDa, or from about 45 kDa to about 50 kDa. The present disclosure contemplates PEGs having molecular masses greater than 50 kDa in 5 kDa increments (e.g., 55 kDa, 60 kDa, 65 kDa, etc.).

Although the present disclosure does not require use of a specific method or site of PEG attachment to IL-15, it is frequently advantageous that pegylation improves, does not alter, or only nominally decreases the activity of the IL-15 molecule. In certain embodiments, the impact of any increase in half-life is greater than the impact of any decrease in biological activity. The biological activity of PEG-IL-15 is frequently measured by assessing the levels of inflammatory cytokines (e.g., IFN-γ) in the serum of subjects challenged with a bacterial antigen (lipopolysaccharide (LPS)) and treated with PEG-IL-15. Other means for measuring bioactivity are described elsewhere herein.

IL-15 Variants

IL-15 variants can be prepared with various objectives in mind, including increasing serum half-life, reducing an immune response against IL-15, facilitating purification or preparation, decreasing degradation, improving therapeutic efficacy, and lessening the severity or occurrence of side effects during therapeutic use. The amino acid sequence variants are usually predetermined variants not found in nature, although some may be post-translational variants, e.g., glycosylated variants. Any variant of IL-15 can be used provided it retains a suitable level of IL-15 activity. IL-15 activities are described elsewhere herein (e.g., regulation of T cell and natural killer (NK) cell activation and proliferation).

The phrase "conservative amino acid substitution" refers to substitutions that preserve the activity of the protein by replacing an amino acid(s) in the protein with an amino acid with a side chain of similar acidity, basicity, charge, polarity, or size of the side chain. Conservative amino acid substitutions generally entail substitution of amino acid residues within the following groups: 1) L, I, M, V, F; 2) R, K; 3) F, Y, H, W, R; 4) G, A, T, S; 5) Q, N; and 6) D, E. Guidance for substitutions, insertions, or deletions may be based on alignments of amino acid sequences of different variant proteins or proteins from different species. Thus, in addition to any naturally-occurring IL-15 polypeptide, the present disclosure contemplates having 1, 2, 3, 4, 5, 6, 7, 8, 9, or 10 usually no more than 20, 10, or 5 amino acid substitutions, where the substitution is usually a conservative amino acid substitution. If should be noted that one or more unnatural amino acids may be introduced into IL-15 as a means of fostering site-specific conjugation.

The present disclosure also contemplates active fragments (e.g., subsequences) of mature IL-15 containing contiguous amino acid residues derived from the mature IL-15. The length of contiguous amino acid residues of a peptide or a polypeptide subsequence varies depending on the specific naturally-occurring amino acid sequence from which the subsequence is derived. In general, peptides and polypeptides may be from about 20 amino acids to about 40 amino acids, from about 41 amino acids to about 50 amino acids, from about 51 amino acids to about 60 amino acids, from about 61 amino acids to about 70 amino acids, from about 71 amino acids to about 80 amino acids, from about 81 amino acids to about 90 amino acids, from about 91 amino acids to about 100 amino acids, from about 101 amino acids to about 105 amino acids, from about 106 amino acids to about 110 amino acids, or from about 111, 112, or 113 amino acids up to the full-length peptide or polypeptide.

Additionally, IL-15 polypeptides can have a defined sequence identity compared to a reference sequence over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a suitable IL-15 polypeptide can comprise an amino acid sequence having at least about 75%, at least about 80%, at least about 85%, at least about 90%, at least about 95%, at least about 98%, or at least about 99%, amino acid sequence identity to a contiguous stretch of from about 20 amino acids to about 40 amino acids, from about 41 amino acids to about 50 amino acids, from about 51 amino acids to about 60 amino acids, from about 61 amino acids to about 70 amino acids, from about 71 amino acids to about 80 amino acids, from about 81 amino acids to about 90 amino acids, from about 91 amino acids to about 100 amino acids, from about 101 amino acids to about 105 amino acids, from about 106 amino acids to about 110 amino acids, or from about 111, 112, or 113 amino acids up to the full-length peptide or polypeptide.

As discussed further below, the IL-15 polypeptides may be isolated from a natural source (e.g., an environment other than its naturally-occurring environment) and may also be recombinantly made (e.g., in a genetically modified host cell such as bacteria, yeast, *Pichia,* insect cells, and the like), where the genetically modified host cell is modified with a nucleic acid comprising a nucleotide sequence encoding the polypeptide. The IL-15 polypeptides may also be synthetically produced (e.g., by cell-free chemical synthesis).

Nucleic acid molecules encoding the IL-15 molecules are contemplated by the present disclosure, including their naturally-occurring and non-naturally occurring isoforms, allelic variants and splice variants. The present disclosure also encompasses nucleic acid sequences that vary in one or more bases from a naturally-occurring DNA sequence but still translate into an amino acid sequence that corresponds to an IL-15 polypeptide due to degeneracy of the genetic code.

IL-15 Mutants (e.g., Muteins) and Modified IL-15 Molecules

The present disclosure is drawn, in part, to the manipulation of protein function through mutagenesis of, and other modifications to, IL-15. In some embodiments, the present disclosure contemplates modified IL-15 molecules wherein one or more advantageous characteristics have been added to IL-15 (in cases where the characteristic(s) is not present in the unmodified IL-15), and/or enhanced (in cases where the characteristic(s) is present in the unmodified IL-15, albeit in a less-than-optimal amount). As discussed further hereafter, such molecules may be identified and synthesized through rational drug design approaches comprising, for example, generation of a series of point mutations in human IL-15. This series of point mutations may be evaluated to determine the nature and extent of the properties (e.g., efficacy) of the members in the series.

In some embodiments, the point mutations are used to facilitate the synthesis of, for example, modified IL-15 peptides, wherein the peptides comprise covalent or non-covalent modifications (e.g., pegylation, Fc-fusions, and HSA fusions). In turn, systematic assessment of the modified peptides can be performed to define the locations of the IL-15 primary amino acid sequence where modifications can be effected while a) retaining protein bioactivity; b) enhancing certain protein functions; c) deemphasizing certain IL-15 functions while maintaining others; or d) some combination of a)-c).

One goal of the rational drug design approaches contemplated herein is identification of those amino acid residues and regions of IL-15 that can be modified without having deleterious effects on bioactivity, while allowing other attributes to be added or enhanced. Another goal of these rational drug design approaches is to define amino acid residues and regions of IL-15 where modifications can be used to selectivity deemphasize certain IL-15 functions while maintaining or enhancing the others. Thus, in certain embodiments, the IL-15 molecules (e.g., muteins) or modified IL-15 molecules accentuate one or more roles of IL-15 while deemphasizing one or more different roles; accentuate one or more roles of IL-15 while not affecting the others (e.g., retaining normal levels of IL-15 activity); or deemphasize one or more roles of IL-15 while not affecting the others. In certain embodiments, a modification(s) may result in a decrease in bioactivity, provided that another characteristic(s) (e.g., a pharmacokinetic parameter such as half-life) is enhanced, resulting in a modified IL-15 molecule that is at least, and generally more, beneficial from a therapeutic perspective.

In particular embodiments, the modification(s) described herein improves at least one property or other characteristic (e.g., solubility) of the peptides compared to unmodified versions of the peptides thereof. Further embodiments of the present disclosure pertain to methods and other technologies for identifying specific amino acid residues or domains of IL-15 that may be modified according to the methods described herein. Methods of using (e.g., in the treatment or prevention of a disorder or a symptom thereof) and identifying and/or generating the peptides described herein are also aspects of the present disclosure. Such aspects are discussed elsewhere herein. Other aspects include, for example, pharmaceutical compositions comprising the peptides.

Although identification of certain IL-15 functional domains and generation of particular types of IL-15 conjugates have been described, the literature is devoid of any disclosure of the types of IL-15 molecules described herein, along with methods for identifying and/or generating them and methods of using same.

In particular embodiments, the present disclosure contemplates generation of a series of point mutations in human IL-15 and expression of those mutated IL-15 proteins (e.g., muteins) in, for example, a mammalian or bacterial system. The present disclosure contemplates the use of any expression system compatible with the mutant IL-15 molecules described herein. Mammalian protein expression systems are contemplated in particular embodiments, while in other embodiments candidate protein expression systems include those derived from bacteria (e.g., *E. coli, Corynebacterium, P. fluorescens,* and *B. subtilis*), yeast (e.g., *S. cerevisiae*), and baculovirus-infected insect cells. Cell-based or cell-free expression systems may be used. Most recombinant cytokines are produced in bacterial inclusion bodies, then purified and refolded.

Bacterial cells are frequently employed to express cytokines, a method which typically involves protein refolding. However, it can be advantageous to initially use a mammalian expression system in order to determine whether a mutated protein will be expressed. If the mammalian cell can express the mutated protein, then protein folding likely was not disrupted by the mutation. There is frequently a close correlation between the ability of a mammalian cell line to fold and secrete a mutant molecule and the viability of that molecule as a candidate for further evaluation. Conversely, if initial expression is carried out in bacteria and a mutated protein is not properly refolded, then it would not be clear whether the mutation was disruptive or the protein refolding protocol was sub-optimal.

Mutant IL-15 molecules that do not significantly disrupt protein folding and secretion in an expression system (e.g., a mammalian cell line-based expression system) may be candidates for further evaluation. For example, such mutant IL-15 molecules may be sufficiently purified to enable bioactivity analysis in one or more in vivo or in vitro/ex vivo assays, including the CTLL-2 cell proliferation assay described herein. By way of further example, such mutant IL-15 molecules may be evaluated in an in vitro assay that provides an IL-15/IL-15 binding partner affinity measurement. In addition, in vivo models have been described and may be used in assessment of the IL-15 molecules described herein.

In particular embodiments, the mutant IL-15 polypeptide molecules (e.g., muteins) are modified by, for example, pegylation. These modified IL-15 molecules may then be evaluated to determine their impact on protein function. Modified IL-15 molecules exhibiting favorable characteristics (e.g., nominal or no impact on protein function) may be candidates for further modification (e.g., larger or branched PEGs) and evaluation (e.g., solubility). Pegylation and other types of modifications are described in detail elsewhere herein.

In addition, the present disclosure contemplates evaluation of the mutant IL-15 peptides and modified IL-15 peptides using one or more assays for determining immunogenicity, such as those in vitro, ex vivo, or in silico immunogenicity assays described herein. Modified IL-15 molecules exhibiting particular favorable characteristics (e.g., enhanced efficacy without an increase in immunogenicity as determined in silico) may be candidates for further evaluation, including in vivo immunogenicity analysis and/or additional analyses in an in vivo setting. In particular embodiments, these modified IL-15 molecules are not more immunogenic than the corresponding unmodified IL-15 molecules.

Encompassed herein are other IL-15 molecules, including IL-15 fragments; molecules that comprise an IL-15 polypeptide complexed with a heterologous protein; and IL-15 fusion proteins that comprise IL-15 fused, at the nucleic acid level, to one or more therapeutic agents (e.g., an anti-inflammatory biologic). Such molecules may be modified using the approaches described herein or any other approach known to the skilled artisan.

The rational drug design approaches of the present disclosure may utilize crystallographic and similar data from a number of sources. By way of example, the crystal structure of IL-15 in complex with the sushi domain of IL-15Ralpha has been described. Olsen, et al., J. Biol. Chem. 282(51): 37191-204 (Dec. 21 2007). In addition, Pettit, et al., J. Biol. Chem. 272:2312-18 (1997)) describe structure-function studies of IL-15 using site-specific mutagenesis, polyethylene glycol conjugation, and homology modeling. Though insufficient and incomplete in and of themselves, the information and data described in such sources may represent a component used in the identification of IL-15 amino acid residues and domains that may be modified. As a result of leveraging such information and data, mutant IL-15 molecules (e.g., muteins) and modified mutant IL-15 molecules (and, in some embodiments, modified native hIL-15) were identified as having the advantageous and/or desirable characteristics described herein.

As described herein and depicted in FIG. 3, mature hIL-15 comprises a) a Helix A (amino acid residues 1-17); b) an A/B Inter-helix Junction (A/B Loop) (amino acid residues 18-31); c) a Helix B (amino acid residues 32-53); d) a B/C Inter-helix Junction (B/C Turn) (amino acid residues 54-57); e) a Helix C (amino acid residues 58-77); f) a C/D Inter-helix Junction (C/D Loop) (amino acid residues 78-96); and g) a Helix D (amino acid residues 97-114). In some embodiments, the present disclosure contemplates peptides comprising a) a Helix A; b) an A/B Inter-helix Junction; c) a Helix B; d) a B/C Inter-helix Junction; e) a Helix C; f) a C/D Inter-helix Junction; and g) a Helix D; wherein such peptides further comprise at least one of: i) substitution of at least one amino acid residue of Helix A other than amino acid residues 2 (W), 4-12 (NVISDLKKI; SEQ ID NO:37)), or 16 (I); or ii) substitution of at least one amino acid residue of the A/B Inter-helix Junction other than amino acid residues 30 (D) or 31 (V); or iii) substitution of at least one amino acid residue of Helix B other than amino acid residues 32 (H), 35 (C), 40 (M), 42-44 (CFL), 47 (L) or 50 (I); or iv) substitution of at least one amino acid residue of the B/C Inter-helix Junction; or v) substitution of at least one amino acid residue of Helix C other than amino acid residues 59 (I), 61-66 (DTVENL; SEQ ID NO:38), or 68-70 (ILA); or vi) substitution of at least one amino acid residue of the C/D Inter-helix Junction other than amino acid residues 85 (C) or 88 (C); or vii) substitution of at least one amino acid residue of Helix D other than amino acid residues 99 (F), 100 (L), 103 (F), or 105-112 (HIVQMFIN; SEQ ID NO:39). The boundaries of these regions are set forth in FIG. 3.

Although the boundaries of the helices and the inter-helix junctions set forth in FIG. 3 are generally accepted in the art as defining those specific regions, the skilled artisan will recognize that there may be certain deviations in the specific amino acid residues that define such regions. The skilled artisan is able to take such deviations into consideration when practicing the present disclosure.

Figure 4B:
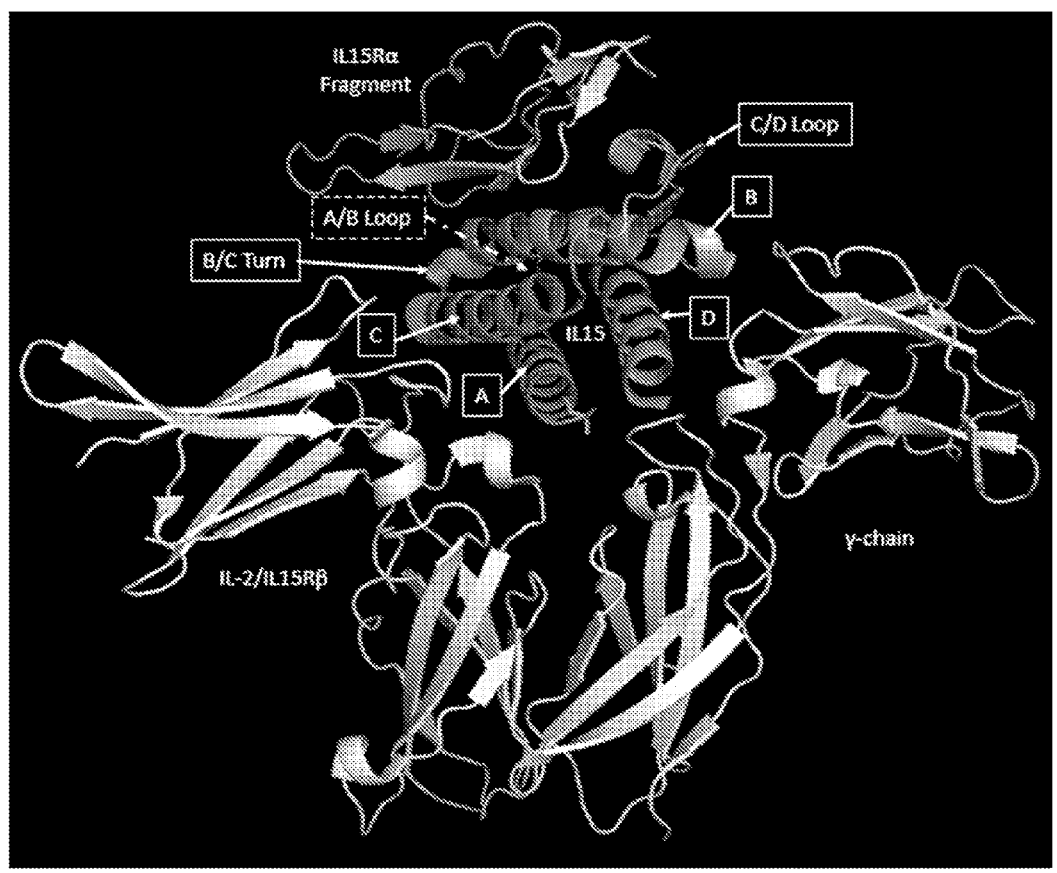
FIG. 4B is a protein crystal structure ribbon representation of the IL-15 Receptor Signaling Complex (PDB 4GS7); side view: IL2/15Rβ, IL15Rα, the common γ-chain, and IL-15 (Helices and intrahelical features are labeled).

While the mechanics of IL-15 receptor binding and signaling have not been thoroughly elucidated, it has been shown that IL-15 functions in a complex with IL-15Rα. This complex works in concert with IL-2/IL-15Rβ and γc in order to effect IL-15 signaling. FIG. 4A is a protein crystal structure ribbon representation (top view) of human IL-15, with certain helices and inter-helices junctions being labeled. Certain IL-15 binding partners (e.g., IL-15Rα) are also depicted. FIG. 4B is a protein crystal structure ribbon representation (side view) of human IL-15, with certain helices and inter-helices junctions being labeled. Certain IL-15 binding partners (e.g., IL-15Rα) are also depicted.

Amino acid residues likely to be poor candidates for modification (e.g., pegylation) include: residues in a hydrophobic core region, which are likely to be inaccessible to modification; residues contacting or in close proximity to a binding interface (e.g., residues involved in IL-15 Beta/Gamma receptor binding); and cysteine residues involved in disulfide bonds, which are generally non-reactive with cysteine-based pegylation chemistries (though cysteine pegylation of disulfide bonds has been accomplished using defined pegylation conditions). In contrast, amino acid residues likely to be good candidates for potential modification (e.g., pegylation) include surface-exposed residues not involved in protein-protein interactions, or residues that form the inter-helices junctions. Of note, IL-15 has been observed to be conformationally 'plastic' when not bound by IL-15Rα (Ring et al., Nat. Immunol. 13(12):1187-95 (Dec. 13, 2012)).

Chemistries currently exist for pegylation of, for example, a polypeptide's N-terminus, lysine residues, cysteine residues, histidine residues, arginine residues, aspartic acid residues, glutamic acid residues, serine residues, threonine residues, tyrosine residues, and C-terminus. As indicated above, the present disclosure contemplates the introduction of unnatural amino acid residues which may, in turn, be pegylated. However, only some of these amino acid residues can routinely be pegylated in a site-specific manner. Pegylation of other amino acids can only be effected in a site-specific manner under complex conditions, while pegylation of other amino acids (e.g., glutamic acid and serine residues) often results in too many positional isomers to be useful.

An assessment of possible residues (e.g., histidine and threonine) within mature IL-15 that are possibly amenable to pegylation are as follows: N-terminus found to be a useful site for pegylation; C-terminus found to be a possible useful site for pegylation; Lysine (K)—seven residues are present in mature IL-15 but none were found to be useful sites for pegylation; Cysteine (C)—four residues are present in mature IL-15 but none were found to be useful sites for pegylation; Histidine (H)—four residues are present in mature IL-15 but none were found to be useful sites for pegylation; Aspartic Acid (D)—six residues are present in mature IL-15 but none were found to be useful sites for pegylation; Glutamic Acid (E)—twelve residues are present in mature IL-15 but none were found to be useful sites for pegylation; Serine (S)—thirteen residues are present in mature IL-15 but none were found to be useful sites for pegylation; and Threonine (T)—six residues are present in mature IL-15 but none were found to be useful sites for pegylation. In one embodiment, the sole tyrosine (Y) residue in mature IL-15 represents a possible site for pegylation.

While each of the aforementioned residues may be amenable to pegylation under appropriate conditions, the number of residues that are actual candidates for pegylation from a commercial perspective is a subset of those set forth above.

By way of example, current lysine-based pegylation strategies do not allow pegylation of a specific lysine(s) (from among the seven lysine residues within the wildtype IL-15 molecule) without the generation of positional isomers. Such positional isomers are often intolerable in a therapeutic agent. Moreover, they frequently introduce additional complexities in manufacturing processes. Finally, certain pegylation strategies will result in pegylation of 'non-target' residue(s) if those residues have a similar bond or ring structure to the 'target' residue(s).

Figure 5:
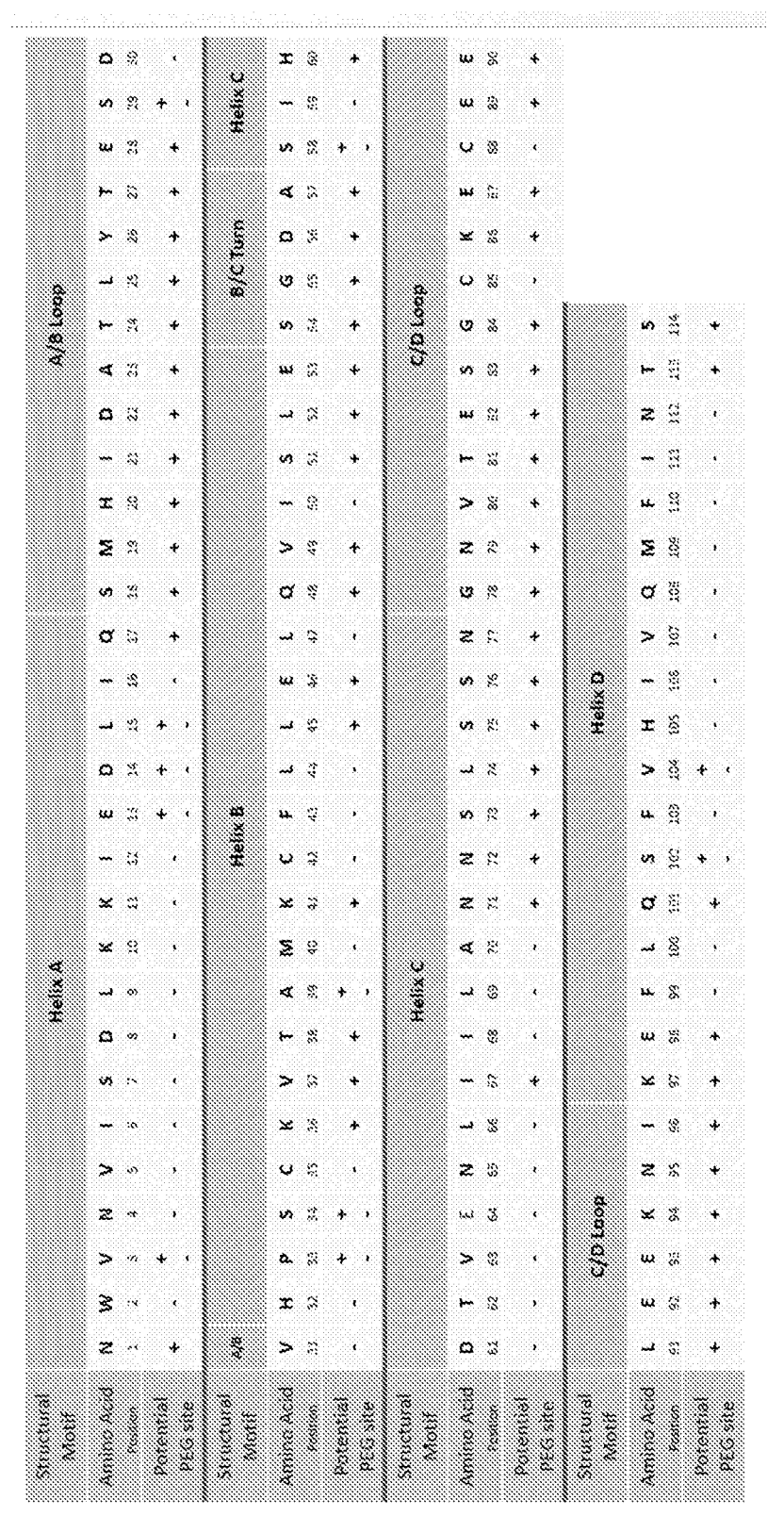

According to the teachings set forth herein, of the 114 amino acid residues of mature IL-15, modification of amino residues via a combination of mutagenesis and site-specific chemistries is not predicted to be useful for 44 residues (see FIG. 5). Of those 44 residues, four are likely to be involved in disulfide bonds. The remaining 40 residues are likely to be in contact with the receptor signaling complex, buried within a hydrophobic core region of the tertiary IL-15 structure, or both. An understanding of how the various components of the IL-15/IL-2 receptor signaling complex interact, and how signaling is effected, is not required in order to practice the present disclosure. However, of the three IL-15R subunits (α, β and γc), signaling is believed comprise binding of IL-15 to the β and γc subunits. As such, in some embodiments the present disclosure contemplates pegylation of one or more amino acid residues of IL-15 that bind IL-15Rα because such pegylation should only have a nominal impact, if any, on IL-15 signaling. Conversely, based on the teachings set forth herein, modification of amino acid residues via a combination of mutagenesis and site-specific chemistries is predicted to be feasible for 59 residues, which are likely to be surface-exposed and not integrally involved in the IL-15 receptor complex or in disulfide bonding. Eleven residues are believed to have the potential for being potential pegylation sites (e.g., a residue flanked by one residue involved in receptor binding and another surface-exposed residue not involved in receptor binding), as indicated by "+/−" in FIG. 5. It is to be understood that depending on the methodologies used and other parameters, a skilled artisan might conclude that one or more of the residues deemed not to be a potential pegylation site, one or more residues deemed to be a potential pegylation site, and/or one or more residues deemed to possibly be a potential pegylation site may fall into a different category (e.g., a residue that is possibly a potential pegylation site might be concluded to be a potential pegylation site).

As set forth above, 59 amino acid residues represent sites that potentially tolerate mutations by substitution of an amino acid that will serve as an anchor for a PEG. Of these 59 possible sites, some mutants are eliminated at specific locations for various reasons: residue 26 (Y) cannot be mutated to a tyrosine because human IL-15 already contains a tyrosine at that position; residue 71 (N) already contains an N-X-S N-glycosylation motif so only an N-X-T motif can be introduced; residue 79 (N) already contains an N-X-T N-glycosylation motif so only an N-X-S motif can be introduced; and residue 112 (N) already contains an N-X-S N-glycosylation motif so only an N-X-T motif can be introduced. Residues 113 (T) and 114 (S) are the second to last residue and last residue, respectively, and thus the 3 amino acid N-glycosylation motif cannot be added. Due to the motif for an N-glycosylation site spanning three amino acids (N-X-S or N-X-T, where X≠P), it was sometimes necessary to mutate a residue(s) flanking the N-glycosylation mutation; however, such mutations were designed so that the N-glycosylation would occur at the specific residues of interest.

The mutants were generated using the methods described herein and were evaluated in a CTLL-2 proliferation assay to determine biological activity.

FIG. 6 sets forth the CTLL-2 proliferation data for specific substitutions. A review of the data yields several general observations. First, loops between helices are typically good places to mutate. However, some residues within the A/B Loop are poor candidates for modification. Second, although cysteine mutants are often very disruptive, only mutation of residues 6 (I) and 70 (A) were inactive. A detailed discussion regarding the precise substitutions that may be made to introduce an amino acid that will serve as a site for pegylation is set forth below. However, several residues that were most amenable to substitution while retaining some biological activity are summarized as follows: a) all four substitutions (i.e., tyrosine (Y), cysteine (C), N-X-S, and N-X-T) of amino acid residue 1 (N) yielded an active protein, and standard N-terminal pegylation strategies may readily be employed; b) substitutions of amino acid residues 13 (E) to 15 (L) yielded favorable results; c) substitutions of amino acid residues 17 (Q) to 23 (A) yielded favorable results; d) substitutions of amino acid residues 48 (Q), 49 (V), 51 (S) to 58 (S), and 60 (H) yielded an active protein; e) amino acid residues 71 (N) to 84 (G) yielded favorable results, with the exception of two mutations across this thirteen residue span; f) substitutions of amino acid residues 89 (E) to 98 (E) yielded favorable results; and g) amino acid residues 113 (T) and 114 (S) at the C-terminus yielded favorable results, and standard C-terminal pegylation strategies may readily be employed.

Some embodiments of the present disclosure contemplate peptides comprising at least one amino acid substitution in at least one of the following regions: 17-28, 36-38, 51-57, 71-84, or 89-98. In other embodiments, the peptides comprise at least one amino acid substitution at least at one of the following positions: 1, 17-28, 36-38, 41, 45, 46, 48, 49, 51-57, 60, 67, 71-84, 86, 87, 89-98, 101, 113 or 114. In further embodiments, the peptides comprise at least one amino acid substitution at least at one of the following positions: 1, 3, 13-15, 17-29, 33, 34, 36-39, 41, 45, 46, 48, 49, 51-58, 60, 67, 71-84, 86, 87, 89-98, 101, 102, 104, 113 or 114.

Identifying Mutants Demonstrating Biological Activity

Using the methodologies described herein, an assessment was conducted to determine which of the 114 amino acid residues of the mature human IL-15 protein will tolerate a substitution with a residue conducive to forming an anchor site for a PEG moiety. Residues identified using this assessment were further analyzed to determine whether a substitution will result in a mutant (mutein) exhibiting bioactivity. The skilled artisan will recognize that not all mutants active in an in vitro assay will have activity in an in vivo setting, and vice versa.

As indicated above and in FIG. 5, 44 amino acid residues (represented by a "−") of the 114 residue mature human IL-15 polypeptide are not candidates for pegylation. Four of these 44 residues are cysteines that form disulfide bonds (residue 35→85 and residue 42→88) and are thus unavailable for mutation. The remaining 40 residues are likely to be in contact with the receptor signaling complex, buried within a hydrophobic core region of the tertiary IL-15 structure, or both. Thus, 70 residues (59 of which are associated with a "+" and 11 of which are associated with a "+/−" in FIG. 5) represent sites that might tolerate mutations by substitution of an amino acid that will serve as an anchor for a PEG. Mutations at these potential sites were then evaluated using a CTLL-2 cell proliferation assay as described herein.

Figure 6A:
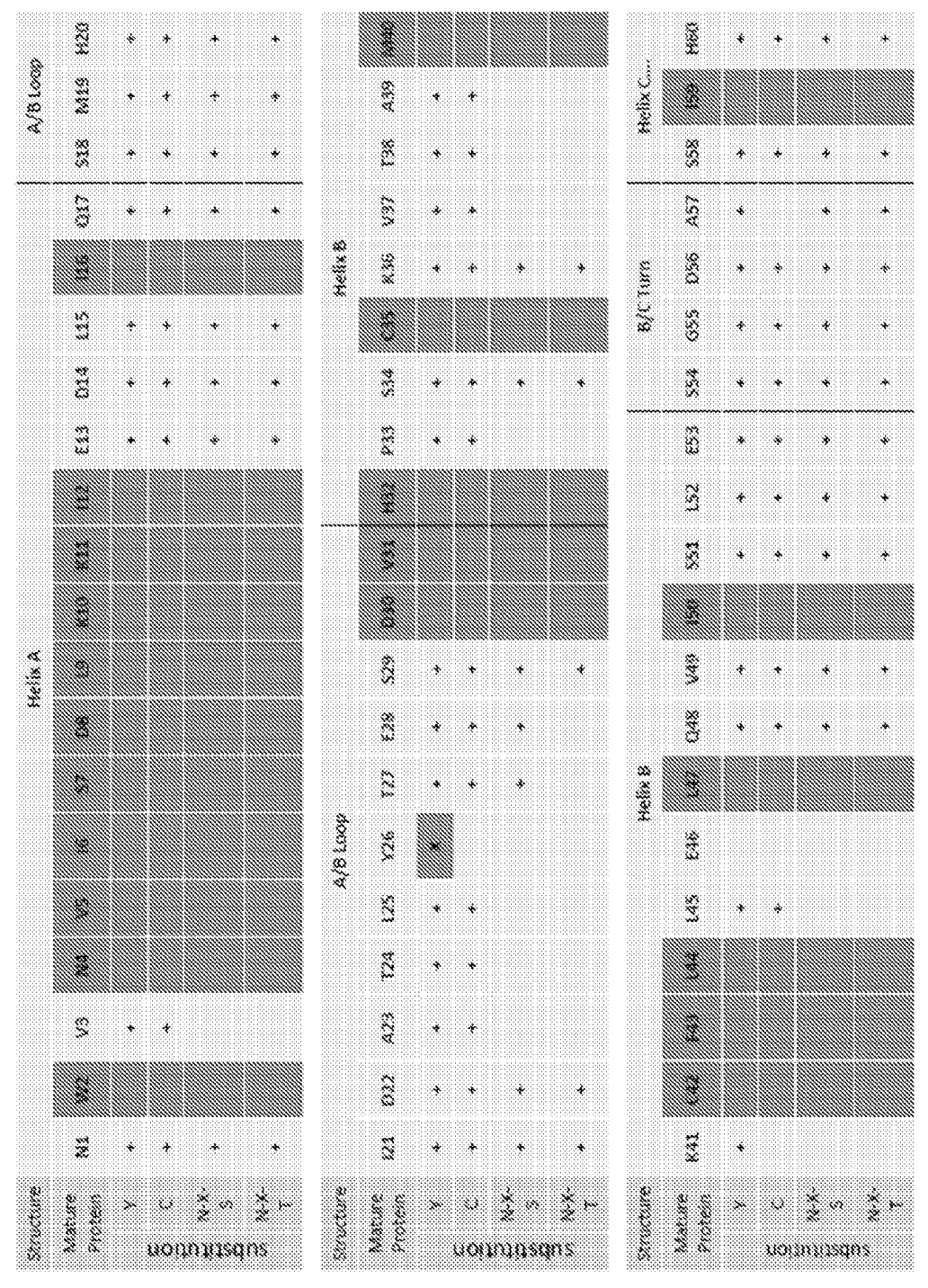
Figure 6B:
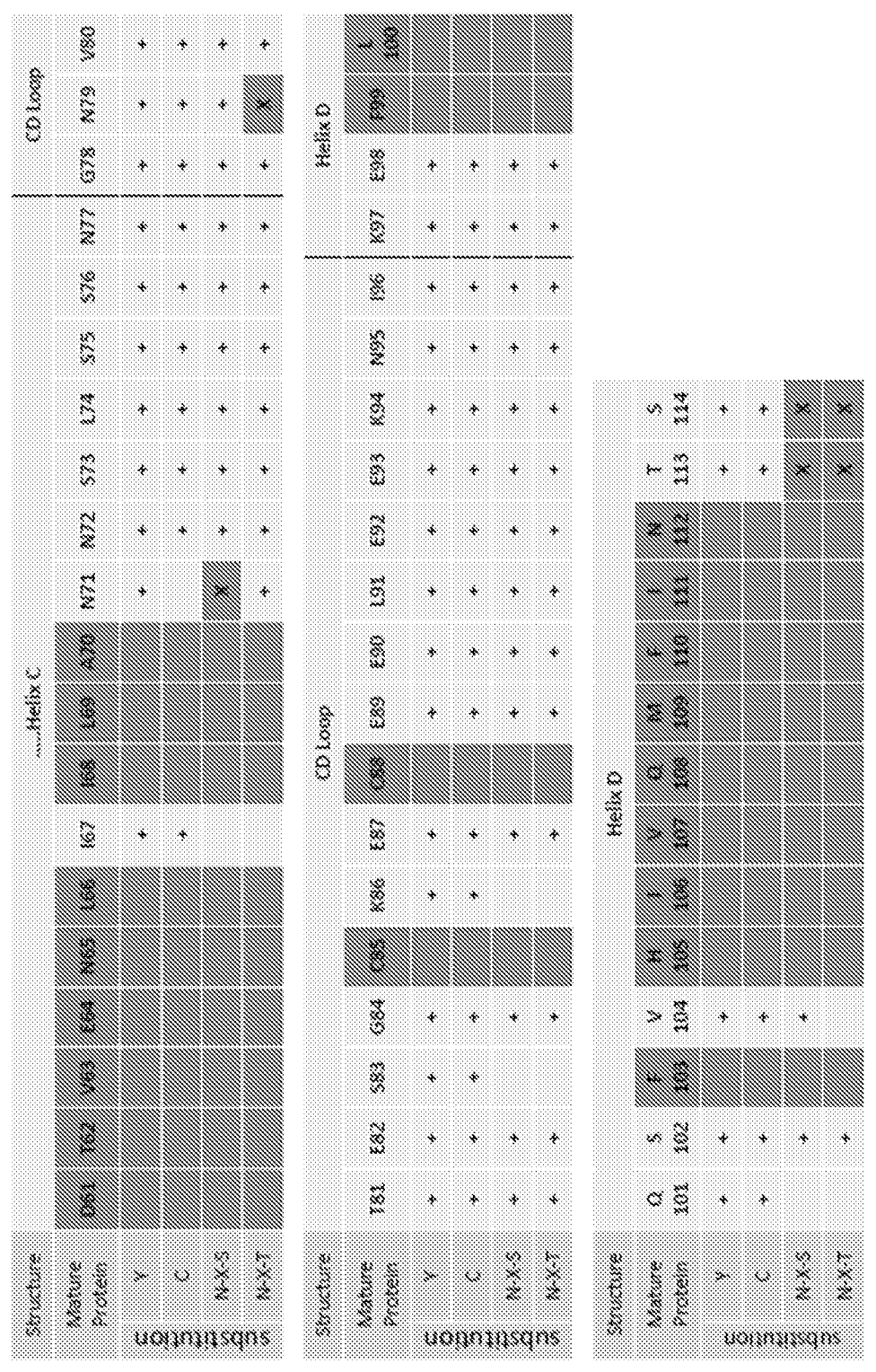

The results of the assessment are summarized in FIGS. 6A-6B. The first row of FIGS. 6A-6B defines the boundaries for each of the regions of IL-15: a) Helix A; b) A/B Loop (i.e., A/B Inter-helix Junction); c) Helix B; d) B/C Turn (i.e., B/C Inter-helix Junction); e) Helix C; f) CD Loop (i.e., C/D Inter-helix Junction); and g) Helix D. The second row sets forth each amino acid residue of the 114 residue mature IL-15 polypeptide. The next four rows of FIG. 6 relate to the types of mutations that were introduced at each residue: Cysteine, Tyrosine, and N-X-S and N-X-T N-glycosylation motifs.

Referring to the shading in FIGS. 6A-6B, with the exception of the dark grey boxes with an "x" that are described below, the residues in the dark grey boxes were neither mutated nor part of the analysis, as they were not deemed to be good candidates for the introduction of an amino acid that could serve as an anchor for a PEG; as indicated above, such residues are likely to be in contact with the receptor signaling complex, buried within a hydrophobic core region of the tertiary IL-15 structure, or both. However, it should be noted that some of these residues were mutated in the context of introducing an N-glycosylation site. The remaining 70 residues in the light grey boxes represent the residues that are more likely to be surface exposed on the homodimer and less likely to interfere with receptor binding. It is to be understood that a skilled artisan may conclude that one or more residues may be categorized differently (i.e., a residue that is in a dark grey box might be placed in a light gray box).

The mutants (e.g., cysteine or tyrosine) were generated using the methods described herein and their biological activity was evaluated in a CTLL-2 cell proliferation assay, described in the Experimental section and substantively similar to that described by Soman et al. (J Immunol Methods 348(1-2):83-94 (2009 August 31)). If a mutant was expressed and exhibited biological activity, a "+" was placed in the applicable box (e.g., referring to amino acid residue 41, a tyrosine mutant exhibited activity whereas a cysteine mutant did not). For purposes of the assessment, the measurement of any biological activity resulted in the assignment of a "+" sign. Mutants in light grey boxes without a "+" (i.e., blank grey boxes) indicate that the mutants did not express or were not active in the CTLL-2 assay.

In some of the light grey columns associated with particular amino acid residues in FIGS. 6A-6B, some boxes (light grey) may be blank or contain a "+", while other boxes are dark grey and contain an "x". In these instances, the dark grey "x" boxes could not be mutated for various reasons. Residue 26 (Y) could not be mutated to a tyrosine because human IL-15 already contains a tyrosine at that position. For residue 71 (N), the N-X-S N-glycosylation motif could not be introduced because the protein already contains an N-X-S N-glycosylation motif. For residue 79 (N), the N-X-T N-glycosylation motif could not be introduced because the protein already contains an N-X-T N-glycosylation motif. For residue 113 (T), because the N-glycosylation motif is three amino acids long (N-X-S or N-X-T), an N-glycosylation site could not be introduced at the second-to-last residue of the protein. For residue 114 (S), because the N-glycosylation motif is three amino acids long, an N-glycosylation site could not be introduced at the last residue of the protein.

In view of the teachings depicted in FIGS. 6A-6B and described elsewhere herein, the skilled artisan will recognize the following: 1) There are 70 potential residues where a mutation may be introduced for purposes of anchoring a PEG moiety (i.e., there are 70 light grey columns). 2) Of the 70 potential residues, further evaluation indicated that 69 residues possessed properties that made them viable candidates for anchoring a PEG moiety, as residue 46 (E) did not generate an active protein with any of the tested mutations. 3) A tyrosine can be substituted for each of the 69 residues and yield a bioactive protein except for residue 26, which is already a tyrosine. 4) A cysteine can be substituted for each of the 69 residues and yield a bioactive protein except residues 26 (Y), 41 (K), 57 (A) and 71 (N). 5) An N-X-S glycosylation motif can be generated at each of the 69 residues and yield a bioactive protein except residues 3 (V), 23 (A) to 26 (Y), 33 (P), 37 (V) to 39 (A), 41 (K), 45 (L), 67 (I), 83 (S), 86 (K), and 101 (Q). Residues 113 (T) and 114 (S) cannot accommodate a glycosylation site because, as indicated above, they represent the last two residues of native human IL-15. Residue 71 (N) already represents the asparagine of an N-X-S glycosylation motif 6) An N-X-T glycosylation motif can be generated at each of the 69 residues except residues 3 (V), 23 (A) to 28 (E), 33 (P), 37 (V) to 39 (A), 41 (K), 45 (L), 67 (I), 83 (S), 86 (K), 101 (Q), and 104 (V). Residues 113 (T) and 114 (S) cannot accommodate a glycosylation site because, as indicated above, they represent the last two residues of native human IL-15. Residue 79 (N) already represents the asparagine of an N-X-T glycosylation motif.

Immunogenicity Considerations of Modified Forms of IL-15

Immunogenicity, the ability of an antigen to elicit humoral (B-cell) and/or cell-mediated (T-cell) immune responses in a subject, can be categorized as 'desirable' or 'undesirable'. Desirable immunogenicity typically refers to the subject's immune response mounted against a pathogen (e.g., a virus or bacterium) that is provoked by vaccine injection. In this context, the immune response is advantageous. Conversely, undesirable immunogenicity typically refers to the subject's immune response mounted against an antigen like a therapeutic protein (e.g., IL-15); the immune response can, for example, result in anti-drug-antibodies (ADAs) that adversely impact the therapeutic protein's effectiveness or its pharmacokinetic parameters, and/or contribute to other adverse effects. In this context, the immune response is disadvantageous.

There are a number of subject-specific and product-specific factors that affect a subject's immune reaction to a protein therapeutic. Subject-specific factors include the immunologic status and competence of the subject; prior sensitization/history of allergy; route of administration; dose and frequency of administration; genetic status of the subject; and the subject's status of immune tolerance to endogenous protein. Product-specific factors affecting immunogenicity include product origin (foreign or endogenous); product's primary molecular structure/post-translational modifications, tertiary and quaternary structure, etc.; presence of product aggregates; conjugation/modification (e.g., glycosylation and pegylation); impurities with adjuvant activity; product's immunomodulatory properties; and formulation.

Autologous or human-like polypeptide therapeutics have proven to be surprisingly immunogenic in some applications, and surprisingly non-immunogenic in others. Particular IL-15 muteins and other modified versions of IL-15 (e.g., pegylated IL-15 and IL and IL-15 domains) are likely to provoke a range of humoral and cell-mediated immune responses. As discussed further herein, the removal or modification of T-cell epitopes and/or B-cell epitopes can reduce immunogenicity. Indeed, in certain contexts, conjugation of one or more amino acid residues with a 'masking agent' (e.g., a PEG) and/or changes to the amino acids residues themselves (by, e.g., substitutions) may dramatically reduce the immunogenicity of an otherwise highly immunogenic protein.

T-cell Epitopes. As discussed further below, in contrast to the complex three-dimensional B-cell epitopes that often depend on secondary and tertiary protein structure, CD4+ T-cell epitopes are linear peptide sequences typically ranging from about 11 to about 20 amino acid residues in length. Comparative analysis of a range of proteins for which clinical immunogenicity data exists shows a strong relationship between the presence and potency of T-cell epitopes with the immunogenicity of the corresponding protein.

In silico screening tools are frequently used as an initial step in a comprehensive T-cell epitope assessment. The induction of helper CD4+ T-cell responses to a peptide requires peptide binding to MHC class II. Analysis of such peptide binding data can be exploited in the development process of therapeutic proteins. By way of example, Antitope Ltd (Cambridge, UK) has a proprietary in silico molecular modeling technology (iTope™) that models the binding of peptides to 34 MHC class II alleles. The contribution of individual amino acid residues to peptide binding can be determined for each allele, and these data can then be used in the design of 'de-immunized' sequence variants in which T-cell epitopes are mutated to disrupt binding.

In addition, 'immunoinformatics' algorithms and other technologies for identifying T-cell epitopes can be used to triage protein therapeutics into higher-risk and lower-risk categories. To illustrate, protein sequences can be parsed into overlapping 9-mer peptide frames which are then evaluated for binding potential to each of eight common class II HLA alleles that "cover" the genetic backgrounds of most humans. By calculating the density of high-scoring frames within a protein, it is possible to estimate a protein's overall "immunogenicity score". In addition, sub-regions of densely-packed, high scoring frames or "clusters" of potential immunogenicity can be identified, and cluster scores can be calculated and compiled. A protein's "immunogenicity score", along with other determinants of immunogenicity, can then be used to determine the likelihood that a protein will illicit an immune response.

Additional means of reducing a therapeutic protein's immunogenicity may be employed. Technologies (e.g., Antitope's proprietary EpiScreen™ human ex vivo T cell assay system) can be used to determine helper CD4+ T-cell responses to proteins, peptides, formulations, etc. Data generated from the use of such technologies can be used to map helper CD4+ T-cell epitopes within the sequence of the starting protein, and the T-cell epitopes can then be removed from the protein by one or more of the following: designing mutations in order to reduce/eliminate binding to human MHC class II; targeting T-cell receptor contact residues to disrupt recognition of peptide/MHC class II complexes; conducting structural and homology analysis to guide the targeting and substitution of key amino acid residues in order to maintain desired protein activity; and prioritizing T-cell epitopes for removal based on potency.

B-cell Epitopes. B-cell epitopes can be placed in one of two categories. In the first category, epitopes are defined by the primary amino acid sequence of a particular region of a protein, and the components of the epitope are situated sequentially on the protein. These linear B-cell epitopes generally range from about 5 to about 20 amino acid residues in length. In the second category, epitopes are defined by the conformational structure of a protein, and the components of the epitope are situated on separate parts of the protein that are brought into proximity of each other in the folded secondary or tertiary structure of the native protein. Because most B-cell epitopes are based on the conformational structure of a protein, B-cell epitopes are more difficult to identify than T-cell epitopes (which are determined by their primary amino acid sequence).

Examples of previously used sequence-based B-cell epitope predictors include technologies described by Saha S, and Raghava GP ("ABCPred technology") (Proteins (2006) 65:40-48); Chen et al. (Amino Acids (2007) 33:423-28); El-Manzalawy Y, et al. ("BCPred" technology) (J Mol Recognit (2008) 21:243-55); Sweredoski M J, and Baldi P ("COBEpro" technology) (Protein Eng Des Sel (2009) 22:113-20); Wee L J, et al. ("BayesB" technology) (BMC Genomics (2010) 11:S21); and Ansari H R, and Raghava GP ("CBTOPE" technology) (Immunome Res (2010) 6:6).

B-cell Epitope prediction using Support vector machine Tool ("BEST") is a promising new B-cell epitope technology (Gao J, et al. (2012) PLoS ONE 7(6): e40104. doi: 10.1371/journal.pone.0040104). The BEST method predicts epitopes from antigen sequences, in contrast to many previous methods that predict only from short sequence fragments, using a new architecture based on averaging selected scores generated from sliding 20-mers by a Support Vector Machine (SVM). The SVM predictor utilizes a comprehensive and custom-designed set of inputs generated by combining information derived from the chain, sequence conservation, similarity to known (training) epitopes, and predicted secondary structure and relative solvent accessibility. In addition, several commercial entities utilize proprietary technologies to assess B-cell epitopes (e.g., Prolmmune's B-cell ELISpot technology; Prolmmune Ltd.; Oxford, UK).

For purposes of assessing immunogenicity, it is useful to focus on potential T-cell epitopes, which generally, though not always, drive antigen-specific B-cell responses.

Methods of Production of IL-15

A polypeptide of the present disclosure can be produced by any suitable method, including non-recombinant (e.g., chemical synthesis) and recombinant methods.

Chemical Synthesis

Where a polypeptide is chemically synthesized, the synthesis may proceed via liquid-phase or solid-phase. Solid-phase peptide synthesis (SPPS) allows the incorporation of unnatural amino acids and/or peptide/protein backbone modification. Various forms of SPPS, such as 9-fluorenylmethoxycarbonyl (Fmoc) and t-butyloxycarbonyl (Boc), are available for synthesizing polypeptides of the present disclosure. Details of the chemical syntheses are known in the art (e.g., Ganesan A. (2006) Mini Rev. Med. Chem. 6:3-10; and Camarero J. A. et al., (2005) Protein Pept Lett. 12:723-8).

Solid phase peptide synthesis may be performed as described hereafter. The alpha functions (Nα) and any reactive side chains are protected with acid-labile or base-labile groups. The protective groups are stable under the conditions for linking amide bonds but can readily be cleaved without impairing the peptide chain that has formed. Suitable protective groups for the α-amino function include, but are not limited to, the following: Boc, benzyloxycarbonyl (Z), O-chlorbenzyloxycarbonyl, bi-phenylisopropyloxycarbonyl, tert-amyloxycarbonyl (Amoc), α, α-dimethyl-3,5-dimethoxy-benzyloxycarbonyl, o-nitrosulfenyl, 2-cyano-t-butoxy-carbonyl, Fmoc, 1-(4,4-dimethyl-2,6-dioxocylohex-1-ylidene)ethyl (Dde) and the like.

Suitable side chain protective groups include, but are not limited to: acetyl, allyl (All), allyloxycarbonyl (Alloc), benzyl (Bzl), benzyloxycarbonyl (Z), t-butyloxycarbonyl (Boc), benzyloxymethyl (Bom), o-bromobenzyloxycarbonyl, t-butyl (tBu), t-butyldimethylsilyl, 2-chlorobenzyl, 2-chlorobenzyloxycarbonyl, 2,6-dichlorobenzyl, cyclohexyl, cyclopentyl, 144,4-dimethyl-2,6-dioxocyclohex-1-ylidene)ethyl (Dde), isopropyl, 4-methoxy-2,3-6-trimethylbenzylsulfonyl (Mtr), 2,3,5,7,8-pentamethylchroman-6-sulfonyl (Pmc), pivalyl, tetrahydropyran-2-yl, tosyl (Tos), 2,4,6-trimethoxybenzyl, trimethylsilyl and trityl (Trt). In the solid phase synthesis, the C-terminal amino acid is coupled to a suitable support material. Suitable support materials are those which are inert towards the reagents and reaction conditions for the step-wise condensation and cleavage reactions of the synthesis process and which do not dissolve in the reaction media being used. Examples of commercially-available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like.

When preparation of the peptidic acid is desired, polystyrene (1%)-divinylbenzene or TentaGel® derivatized with 4-benzyloxybenzyl-alcohol (Wang-anchor) or 2-chlorotrityl chloride can be used. In the case of the peptide amide, polystyrene (1%) divinylbenzene or TentaGel® derivatized with 5-(4'-aminomethyl)-3',5'-dimethoxyphenoxy)valeric acid (PAL-anchor) or p-(2,4-dimethoxyphenyl-aminomethyl)-phenoxy group (Rink amide anchor) can be used.

The linkage to the polymeric support can be achieved by reacting the C-terminal Fmoc-protected amino acid with the support material by the addition of an activation reagent in ethanol, acetonitrile, N,N-dimethylformamide (DMF), dichloromethane, tetrahydrofuran, N-methylpyrrolidone or similar solvents at room temperature or elevated temperatures (e.g., between 40° C. and 60° C.) and with reaction times of, e.g., 2 to 72 hours.

The coupling of the Nα-protected amino acid (e.g., the Fmoc amino acid) to the PAL, Wang or Rink anchor can, for example, be carried out with the aid of coupling reagents such as N,N'-dicyclohexylcarbodiimide (DCC), N,N'-diisopropylcarbodiimide (DIC) or other carbodiimides, 2-(1H-benzotriazol-1-yl)-1,1,3,3-tetramethyluronium tetrafluoroborate (TBTU) or other uronium salts, O-acyl-ureas, benzotriazol-1-yl-tris-pyrrolidino-phosphonium hexafluorophosphate (PyBOP) or other phosphonium salts, N-hydroxysuccinimides, other N-hydroxyimides or oximes in the presence or absence of 1-hydroxybenzotriazole or 1-hydroxy-7-azabenzotriazole, e.g., with the aid of TBTU with addition of HOBt, with or without the addition of a base such as, for example, diisopropylethylamine (DIEA), triethylamine or N-methylmorpholine, e.g., diisopropylethylamine with reaction times of 2 to 72 hours (e.g., 3 hours in a 1.5 to 3-fold excess of the amino acid and the coupling reagents, for example, in a 2-fold excess and at temperatures between about 10° C. and 50° C., for example, 25° C. in a solvent such as dimethylformamide, N-methylpyrrolidone or dichloromethane, e.g., dimethylformamide).

Instead of the coupling reagents, it is also possible to use the active esters (e.g., pentafluorophenyl, p-nitrophenyl or the like), the symmetric anhydride of the Nα-Fmoc-amino acid, its acid chloride or acid fluoride, under the conditions described above.

The Nα-protected amino acid (e.g., the Fmoc amino acid) can be coupled to the 2-chlorotrityl resin in dichloromethane with the addition of DIEA and having reaction times of 10 to 120 minutes, e.g., 20 minutes, but is not limited to the use of this solvent and this base.

The successive coupling of the protected amino acids can be carried out according to conventional methods in peptide synthesis, typically in an automated peptide synthesizer. After cleavage of the Nα-Fmoc protective group of the coupled amino acid on the solid phase by treatment with, e.g., piperidine (10% to 50%) in dimethylformamide for 5 to 20 minutes, e.g., 2×2 minutes with 50% piperidine in DMF and 1×15 minutes with 20% piperidine in DMF, the next protected amino acid in a 3 to 10-fold excess, e.g., in a 10-fold excess, is coupled to the previous amino acid in an inert, non-aqueous, polar solvent such as dichloromethane, DMF or mixtures of the two and at temperatures between about 10° C. and 50° C., e.g., at 25° C. The previously mentioned reagents for coupling the first Nα-Fmoc amino acid to the PAL, Wang or Rink anchor are suitable as coupling reagents. Active esters of the protected amino acid, or chlorides or fluorides or symmetric anhydrides thereof, can also be used as an alternative.

At the end of the solid phase synthesis, the peptide is cleaved from the support material while simultaneously cleaving the side chain protecting groups. Cleavage can be carried out with trifluoroacetic acid or other strongly acidic media with addition of 5%-20% V/V of scavengers such as dimethylsulfide, ethylmethylsulfide, thioanisole, thiocresol, m-cresol, anisole ethanedithiol, phenol or water, e.g., 15% v/v dimethylsulfide/ethanedithiolm-cresol 1:1:1, within 0.5 to 3 hours, e.g., 2 hours. Peptides with fully protected side chains are obtained by cleaving the 2-chlorotrityl anchor with glacial acetic acid/trifluoroethanol/dichloromethane 2:2:6. The protected peptide can be purified by chromatography on silica gel. If the peptide is linked to the solid phase via the Wang anchor and if it is intended to obtain a peptide with a C-terminal alkylamidation, the cleavage can be carried out by aminolysis with an alkylamine or fluoroalkylamine. The aminolysis is carried out at temperatures between about −10° C. and 50° C. (e.g., about 25° C.), and reaction times between about 12 and 24 hours (e.g., about 18 hours). In addition, the peptide can be cleaved from the support by re-esterification, e.g., with methanol.

The acidic solution that is obtained may be admixed with a 3 to 20-fold amount of cold ether or n-hexane, e.g., a 10-fold excess of diethyl ether, in order to precipitate the peptide and hence to separate the scavengers and cleaved protective groups that remain in the ether. A further purification can be carried out by re-precipitating the peptide several times from glacial acetic acid. The precipitate that is obtained can be taken up in water or tert-butanol or mixtures of the two solvents, e.g., a 1:1 mixture of tert-butanol/water, and freeze-dried.

The peptide obtained can be purified by various chromatographic methods, including ion exchange over a weakly basic resin in the acetate form; hydrophobic adsorption chromatography on non-derivatized polystyrene/divinylbenzene copolymers (e.g., Amberlite® XAD); adsorption chromatography on silica gel; ion exchange chromatography, e.g., on carboxymethyl cellulose; distribution chromatography, e.g., on Sephadex® G-25; countercurrent distribution chromatography; or high pressure liquid chromatography (HPLC) e.g., reversed-phase HPLC on octyl or octadecylsilylsilica (ODS) phases.

Recombinant Production

IL-15 (e.g., murine and human IL-15) can be synthesized in a number of ways using standard techniques known in the art, such as those described herein. IL-15 can be of viral origin, and the cloning and expression of a viral IL-15 from Epstein Barr virus (BCRF1 protein) is disclosed in Moore et al., (1990) Science 248:1230. In addition, recombinant IL-15 is commercially available from a number of sources (e.g., Life Technologies, Grand Island, N.Y. and BioLegend, San Diego, Calif.).

Site-specific mutagenesis (also referred to as site-directed mutagenesis and oligonucleotide-directed mutagenesis) can be used to generate specific mutations in DNA to produce rationally-designed proteins of the present disclosure (e.g., particular IL-15 muteins and other modified versions of IL-15, including domains thereof) having improved or desirable properties. Techniques for site-specific mutagenesis are well known in the art. Early site-specific mutagenesis methods (e.g., Kunkel's method; cassette mutagenesis; PCR site-directed mutagenesis; and whole plasmid mutagenesis, including SPRINP) have been replaced by more precise and efficient methods, such as various in vivo methods that include Delitto perfetto (see Storici F. and Resnick M A, (2006) Methods in Enzymology 409:329-45); transplacement "pop-in pop-out"; direct gene deletion and site-specific mutagenesis with PCR and one recyclable marker; direct gene deletion and site-specific mutagenesis with PCR and one recyclable marker using long homologous regions; and in vivo site-directed mutagenesis with synthetic oligonucleotides (and see, e.g., In Vitro Mutagenesis Protocols (Methods in Molecular Biology), 2nd Ed. ISBN 978-0896039100). In addition, tools for effecting site-specific mutagenesis are commercially available (e.g., Stratagene Corp., La Jolla, Calif.).

Where a polypeptide is produced using recombinant techniques, the polypeptide may be produced as an intracellular protein or as a secreted protein, using any suitable construct and any suitable host cell, which can be a prokaryotic or eukaryotic cell, such as a bacterial (e.g., *E. coli*) or a yeast host cell, respectively. Other examples of eukaryotic cells that may be used as host cells include insect cells, mammalian cells, and/or plant cells. Where mammalian host cells are used, they may include human cells (e.g., HeLa, 293, H9 and Jurkat cells); mouse cells (e.g., NIH3T3, L cells, and C127 cells); primate cells (e.g., Cos 1, Cos 7 and CV1); and hamster cells (e.g., Chinese hamster ovary (CHO) cells).

A variety of host-vector systems suitable for the expression of a polypeptide may be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and may provide for inducible or constitutive expression where the coding region is operably-linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host may be present to facilitate selection of cells containing the vector. Moreover, the expression construct may include additional elements. For example, the expression vector may have one or two replication systems, thus allowing it to be maintained in organisms, for example, in mammalian or insect cells for expression and in a prokaryotic host for cloning and amplification. In addition, the expression construct may contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification. In one embodiment, the protein may be isolated using metal chelate chromatography methods. Proteins may contain modifications to facilitate isolation.

The polypeptides may be prepared in substantially pure or isolated form (e.g., free from other polypeptides). The polypeptides can be present in a composition that is enriched for the polypeptide relative to other components that may be present (e.g., other polypeptides or other host cell components). For example, purified polypeptide may be provided such that the polypeptide is present in a composition that is substantially free of other expressed proteins, e.g., less than about 90%, less than about 60%, less than about 50%, less than about 40%, less than about 30%, less than about 20%, less than about 10%, less than about 5%, or less than about 1%.

An IL-15 polypeptide may be generated using recombinant techniques to manipulate different IL-15-related nucleic acids known in the art to provide constructs capable of encoding the IL-15 polypeptide. It will be appreciated that, when provided a particular amino acid sequence, the ordinary skilled artisan will recognize a variety of different nucleic acid molecules encoding such amino acid sequence in view of her background and experience in, for example, molecular biology.

Amide Bond Substitutions

In some cases, IL-15 includes one or more linkages other than peptide bonds, e.g., at least two adjacent amino acids are joined via a linkage other than an amide bond. For example, in order to reduce or eliminate undesired proteolysis or other means of degradation, and/or to increase serum stability, and/or to restrict or increase conformational flexibility, one or more amide bonds within the backbone of IL-15 can be substituted.

In another example, one or more amide linkages (—CO—NH—) in IL-15 can be replaced with a linkage which is an isostere of an amide linkage, such as —$CH_2NH$—, —$CH_2S$—, —$CH_2CH_2$—, —CH=CH-(cis and trans), —$COCH_2$—, —CH(OH)$CH_2$— or —$CH_2SO$—. One or more amide linkages in IL-15 can also be replaced by, for example, a reduced isostere pseudopeptide bond. See Couder et al. (1993) Int. J. Peptide Protein Res. 41:181-184. Such replacements and how to effect them are known to those of ordinary skill in the art.

Amino Acid Substitutions

One or more amino acid substitutions can be made in an IL-15 polypeptide. The following are non-limiting examples:

a) substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from $C_1$-$C_{10}$ carbons including branched, cyclic and straight chain alkyl, alkenyl or alkynyl substitutions;

b) substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-,or 4'-methyl-, 2-, 3- or 4-biphenylalanine, and 2- or 3-pyridylalanine;

c) substitution of amino acids containing basic side chains, including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination), carboxylic acids or any of the many well-known activated derivatives such as acid chlorides, active esters, active azolides and related derivatives, and lysine, ornithine, or 2,3-diaminopropionic acid;

d) substitution of acidic amino acids, including aspartic acid, glutamic acid, homoglutamic acid, tyrosine, alkyl, aryl, arylalkyl, and heteroaryl sulfonamides of 2,4-diaminopropionic acid, ornithine or lysine and tetrazole-substituted alkyl amino acids;

e) substitution of side chain amide residues, including asparagine, glutamine, and alkyl or aromatic substituted derivatives of asparagine or glutamine; and f) substitution of hydroxyl-containing amino acids, including serine, threonine, homoserine, 2,3-diaminopropionic acid, and alkyl or aromatic substituted derivatives of serine or threonine.

In some cases, IL-15 comprises one or more naturally occurring non-genetically encoded L-amino acids, synthetic L-amino acids, or D-enantiomers of an amino acid. In some embodiments, IL-15 comprises only D-amino acids. For example, an IL-15 polypeptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

Additional Modifications

A cysteine residue or a cysteine analog can be introduced into an IL-15 polypeptide to provide for linkage to another peptide via a disulfide linkage or to provide for cyclization of the IL-15 polypeptide. Methods of introducing a cysteine or cysteine analog are known in the art (see, e.g., U.S. Pat. No. 8,067,532). Other means of cyclization include introduction of an oxime linker or a lanthionine linker; see, e.g., U.S. Pat. No. 8,044,175. Any combination of amino acids (or non-amino acid moieties) that can form a cyclizing bond can be used and/or introduced. A cyclizing bond can be generated with any combination of amino acids (or with an amino acid and —$(CH2)_n$-CO— or —$(CH2)_n$-$C_6H_4$—CO—) with functional groups which allow for the introduction of a bridge. Some examples are disulfides, disulfide mimetics such as the —$(CH2)_n$- carba bridge, thioacetal, thioether bridges (cystathionine or lanthionine) and bridges containing esters and ethers. In these examples, n can be any integer, but is frequently less than ten.

Other modifications include, for example, an N-alkyl (or aryl) substitution (ψ[CONR]), or backbone crosslinking to construct lactams and other cyclic structures. Other derivatives include C-terminal hydroxymethyl derivatives, o-modified derivatives (e.g., C-terminal hydroxymethyl benzyl ether), N-terminally modified derivatives including substituted amides such as alkylamides and hydrazides.

In some cases, one or more L-amino acids in an IL-15 polypeptide is replaced with one or more D-amino acids.

In some cases, an IL-15 polypeptide is a retroinverso analog (see, e.g., Sela and Zisman (1997) FASEB J. 11:449). Retro-inverso peptide analogs are isomers of linear polypeptides in which the direction of the amino acid sequence is reversed (retro) and the chirality, D- or L-, of one or more amino acids therein is inverted (inverso), e.g., using D-amino acids rather than L-amino acids. [See, e.g., Jameson et al. (1994) Nature 368:744; and Brady et al. (1994) Nature 368:692].

An IL-15 polypeptide can include a "Protein Transduction Domain" (PTD), which refers to a polypeptide, polynucleotide, carbohydrate, or organic or inorganic molecule that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of an IL-15 polypeptide, while in other embodiments, a PTD is covalently linked to the carboxyl terminus of an IL-15 polypeptide. Exemplary protein transduction domains include, but are not limited to, a minimal undecapeptide protein transduction domain (corresponding to residues 47-57 of HIV-1 TAT comprising YGRKKRRQRRR; SEQ ID NO:11); a polyarginine sequence comprising a number of arginine residues sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); a Drosophila Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO:7); Transportan GWTLNSAGYLLGKINLKALAALAKKIL (SEQ ID NO:8); KALAWEAKLAKALAKALAKHLAKALAKALKCEA (SEQ ID NO:9); and RQIKIWFQNRRMKWKK (SEQ ID NO:10). Exemplary PTDs include, but are not limited to, YGRKKRRQRRR (SEQ ID NO:11), RKKRRQRRR (SEQ ID NO:12); an arginine homopolymer of from 3 arginine residues to 50 arginine residues; exemplary PTD domain amino acid sequences include, but are not limited to, any of the following: YGRKKRRQRRR (SEQ ID NO:13); RKKRRQRR (SEQ ID NO:14); YARAAARQARA (SEQ ID NO:15); THRLPRRRRRR (SEQ ID NO:16); and GGRRARRRRRR (SEQ ID NO:17).

The carboxyl group $COR_3$ of the amino acid at the C-terminal end of an IL-15 polypeptide can be present in a free form ($R_3$=OH) or in the form of a physiologically-tolerated alkaline or alkaline earth salt such as, e.g., a sodium, potassium or calcium salt. The carboxyl group can also be esterified with primary, secondary or tertiary alcohols such as, e.g., methanol, branched or unbranched $C_1$-$C_6$-alkyl alcohols, e.g., ethyl alcohol or tert-butanol. The carboxyl group can also be amidated with primary or secondary amines such as ammonia, branched or unbranched $C_1$-$C_6$-alkylamines or $C_1$-$C_6$ di-alkylamines, e.g., methylamine or dimethylamine.

The amino group of the amino acid $NR_1R_2$ at the N-terminus of an IL-15 polypeptide can be present in a free form ($R_1$=H and $R_2$=H) or in the form of a physiologically-tolerated salt such as, e.g., a chloride or acetate. The amino group can also be acetylated with acids such that $R_1$=H and $R_2$=acetyl, trifluoroacetyl, or adamantyl. The amino group can be present in a form protected by amino-protecting groups conventionally used in peptide chemistry, such as those provided above (e.g., Fmoc, Benzyloxy-carbonyl (Z), Boc, and Alloc). The amino group can be N-alkylated in which $R_1$ and/or $R_2$=$C_1$-$C_6$ alkyl or $C_2$-$C_8$ alkenyl or $C_7$-$C_9$ aralkyl. Alkyl residues can be straight-chained, branched or cyclic (e.g., ethyl, isopropyl and cyclohexyl, respectively).

Particular Modifications to Enhance and/or Mimic IL-15 Function

It is frequently beneficial, and sometimes imperative, to improve one of more physical properties of the treatment modalities disclosed herein (e.g., an IL-15 mutein) and/or the manner in which they are administered. Improvements of physical properties include, for example, modulating immunogenicity; methods of increasing water solubility, bioavailability, serum half-life, and/or therapeutic half-life; and/or modulating biological activity. Certain modifications may also be useful to, for example, raise antibodies for use in detection assays (e.g., epitope tags) and to provide for ease of protein purification. Such improvements must generally be imparted without adversely impacting (or nominally impacting) the bioactivity of the treatment modality and/or increasing its immunogenicity.

Pegylation of IL-15 is one particular modification contemplated by the present disclosure, while other modifications include, but are not limited to, glycosylation (N- and O-linked); polysialylation; albumin fusion molecules comprising serum albumin (e.g., human serum albumin (HSA), cyno serum albumin, or bovine serum albumin (BSA)); albumin binding through, for example a conjugated fatty acid chain (acylation); and Fc-fusion proteins. In addition, PEG mimetics represent other medications contemplated herein.

Pegylation: The clinical effectiveness of protein therapeutics is often limited by short plasma half-life and susceptibility to protease degradation. Studies of various therapeutic proteins have shown that such difficulties may be overcome by various modifications, including conjugating or linking the polypeptide sequence to any of a variety of nonproteinaceous polymers, e.g., polyethylene glycol (PEG), polypropylene glycol, or polyoxyalkylenes. This is frequently effected by a linking moiety covalently bound to both the protein and the nonproteinaceous polymer, e.g., a PEG. Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity.

PEGs suitable for conjugation to a polypeptide sequence are generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight (molecular mass) of the PEG used in the present disclosure is not restricted to any particular range. Certain embodiments have molecular weights between 5 kDa and 20 kDa, while other embodiments have molecular weights between 4 kDa and 10 kDa. Further embodiments describing PEGs having additional molecular weights are described elsewhere herein.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. Exemplary reaction conditions are described throughout the specification. Cation exchange chromatography may be used to separate conjugates, and a fraction is then identified which contains the conjugate having, for example, the desired number of PEGs attached, purified free from unmodified protein sequences and from conjugates having other numbers of PEGs attached.

Pegylation most frequently occurs at the alpha amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General pegylation strategies known in the art can be applied herein. PEG may be bound to a polypeptide of the present disclosure via a terminal reactive group (a "spacer") which mediates a bond between the free amino or carboxyl groups of one or more of the polypeptide sequences and polyethylene glycol. The PEG having the spacer which may be bound to the free amino group includes N-hydroxysuccinylimide polyethylene glycol, which may be prepared by activating succinic acid ester of polyethylene glycol with N-hydroxysuccinylimide. Another activated polyethylene glycol which may be bound to a free amino group is 2,4-bis(O-methoxypolyethyleneglycol)-6-chloro-s-triazine, which may be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences of the present disclosure to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art may be used to terminate the reaction. In some embodiments the reaction is terminated by acidifying the reaction mixture and freezing at, e.g., −20° C. Pegylation of various molecules is discussed in, for example, U.S. Pat. Nos. 5,252,714; 5,643,575; 5,919,455; 5,932,462; and 5,985,263.

As indicated above, pegylation most frequently occurs at the N-terminus, the side chain of lysine residues, and the imidazole group on the side chain of histidine residues. The usefulness of such pegylation has been enhanced by refinement by, for example, optimization of reaction conditions and improvement of purification processes. More recent residue-specific chemistries have enabled pegylation of arginine, aspartic acid, cysteine, glutamic acid, serine, threonine, and tyrosine, as well as the carboxy-terminus. Some of these amino acid residues can be specifically pegylated, while others are more promiscuous or only result in site-specific pegylation under certain conditions.

Current approaches allowing pegylation of additional amino acid residues include bridging pegylation (disulfide bridges), enzymatic pegylation (glutamines and C-terminus) and glycopegylation (sites of O- and N-glycosylation or the glycans of a glycoprotein), and heterobifunctional pegylation. Further approaches are drawn to pegylation of proteins containing unnatural amino acids, intein fusion proteins for C-terminal pegylation, transglutaminase-mediated pegylation, sortase A-mediated pegylation, and releasable and non-covalent pegylation. In addition, combination of specific pegylation approaches with genetic engineering techniques has enabled the polyethylene glycan polymer to essentially couple at any position on the protein surface due to, for example, substitution of specific amino acid residues in a polypeptide with a natural or unnatural amino acid bearing an orthogonal reactive group. See generally, e.g., Pasut, G. and Veronese, F. M., (2012) J. Controlled Release 161:461-72; Roberts, M. J. et al., (2012) Advanced Drug Delivery Rev. 64:116-27; Jevsevar, S. et al., (2010) Biotechnol. J. 5:113-28; and Yoshioka, Y. (2011) Chem. Central J. 5:25.

The therapeutic value of pegylation molecules is well validated. Previous and/or current pharmaceutical products include: OMONTYS (Affymax/Takeda); PEGLOTICASE (Savient); CIMZIA (Nektar/UCB Pharma); MACUGEN (Pfizer); NEULASTA (Amgen); SOMAVERT (Pfizer); PEGASYS (Roche); DOXIL (Ortho Biotech) and PEGINTRON (Schering-Plough).

The present disclosure also contemplates the use of PEG mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix' XTEN technology; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

Glycosylation: For purposes of the present disclosure, "glycosylation" is meant to broadly refer to the enzymatic process that attaches glycans to proteins, lipids or other organic molecules.

The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present.

Glycosylation can dramatically affect the physical properties (e.g., solubility) of polypeptides such as IL-15 and can also be important in protein stability, secretion, and subcellular localization. Glycosylated polypeptides may also exhibit enhanced stability or may improve one or more pharmacokinetic properties, such as half-life. In addition, solubility improvements can, for example, enable the generation of formulations more suitable for pharmaceutical administration than formulations comprising the non-glycosylated polypeptide.

Proper glycosylation can be essential for biological activity. In fact, some genes from eukaryotic organisms, when expressed in bacteria (e.g., E. coli) which lack cellular processes for glycosylating proteins, yield proteins that are recovered with little or no activity by virtue of their lack of glycosylation.

Addition of glycosylation sites can be accomplished by altering the amino acid sequence. The alteration to the polypeptide may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. A particular embodiment of the present disclosure comprises the generation and use of N-glycosylation variants.

The polypeptide sequences of the present disclosure may optionally be altered through changes at the nucleic acid level, particularly by mutating the nucleic acid encoding the polypeptide at preselected bases such that codons are generated that will translate into the desired amino acids. Another means of increasing the number of carbohydrate moieties on the polypeptide is by chemical or enzymatic coupling of glycosides to the polypeptide. Removal of carbohydrates may be accomplished chemically or enzymatically, or by substitution of codons encoding amino acid residues that are glycosylated. Chemical deglycosylation techniques are known, and enzymatic cleavage of carbohydrate moieties on polypeptides can be achieved by the use of a variety of endo- and exo-glycosidases.

Dihydrofolate reductase (DHFR)-deficient Chinese Hamster Ovary (CHO) cells are a commonly used host cell for the production of recombinant glycoproteins. These cells do not express the enzyme beta-galactoside alpha-2,6-sialyl-transferase and therefore do not add sialic acid in the alpha-2,6 linkage to N-linked oligosaccharides of glycoproteins produced in these cells.

Polysialylation: The present disclosure also contemplates the use of polysialylation, the conjugation of polypeptides to the naturally occurring, biodegradable α-(2→8)-linked polysialic acid ("PSA") in order to improve the polypeptides' stability and in vivo pharmacokinetics. PSA is a biodegradable, non-toxic natural polymer that is highly hydrophilic, giving it a high apparent molecular weight in the blood which increases its serum half-life. In addition, polysialylation of a range of peptide and protein therapeutics has led to markedly reduced proteolysis, retention of in vivo activity, and reduction in immunogenicity and antigenicity (see, e.g., G. Gregoriadis et al., Int. J. Pharmaceutics (2005) 300(1-2):125-30). As with modifications with other conjugates (e.g., PEG), various techniques for site-specific polysialylation are available (see, e.g., T. Lindhout et al., (2011) PNAS 108(18)7397-7402).

Albumin Fusion: Additional suitable components and molecules for conjugation include albumins such as human serum albumin (HSA), cyno serum albumin, and bovine serum albumin (BSA).

Mature HSA, a 585 amino acid polypeptide (~67 kDa) having a serum half-life of ~20 days, is primarily responsible for the maintenance of colloidal osmotic blood pressure, blood pH, and transport and distribution of numerous endogenous and exogenous ligands. The protein has three structurally homologous domains (domains I, II and III), is almost entirely in the alpha-helical conformation, and is highly stabilized by 17 disulphide bridges. The three primary drug binding regions of albumin are located on each of the three domains within sub-domains IB, IIA and IIIA.

Albumin synthesis takes place in the liver, which produces the short-lived, primary product preproalbumin. Thus, the full-length HSA has a signal peptide of 18 amino acids (MKWVTFISLLFLFSSAYS; SEQ ID NO:40) followed by a pro-domain of 6 amino acids (RGVFRR; SEQ ID NO:41); this 24 amino acid residue peptide may be referred to as the pre-pro domain. HSA can be expressed and secreted using its endogenous signal peptide as a pre-pro-domain. Alternatively, HSA can be expressed and secreted using a IgK signal peptide fused to a mature construct. Preproalbumin is rapidly co-translationally cleaved in the endoplasmic reticulum lumen at its amino terminus to produce the stable, 609-amino acid precursor polypeptide, proalbumin. Proalbumin then passes to the Golgi apparatus, where it is converted to the 585 amino acid mature albumin by a furin-dependent amino-terminal cleavage.

The primary amino acid sequences, structure, and function of albumins are highly conserved across species, as are the processes of albumin synthesis and secretion. Albumin serum proteins comparable to HSA are found in, for example, cynomolgus monkeys, cows, dogs, rabbits and rats. Of the non-human species, bovine serum albumin (BSA) is the most structurally similar to HSA (see, e.g., Kosa et al., Nov 2007 J Pharm Sci. 96(11):3117-24). The present disclosure contemplates the use of albumin from non-human species, including, but not limited to, those set forth above, in, for example, the drug development process.

According to the present disclosure, albumin may be conjugated to a drug molecule (e.g., a polypeptide described herein) at the carboxyl terminus, the amino terminus, both the carboxyl and amino termini, and internally (see, e.g., U.S. Pat. Nos. 5,876,969 and 7,056,701).

In the HSA—drug molecule conjugates contemplated by the present disclosure, various forms of albumin may be used, such as albumin secretion pre-sequences and variants thereof, fragments and variants thereof, and HSA variants. Such forms generally possess one or more desired albumin activities. In additional embodiments, the present disclosure involves fusion proteins comprising a polypeptide drug molecule fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. In some embodiments, the indirect fusion is effected by a linker, such as a peptide linker or a modified version thereof.

Intracellular cleavage may be carried out enzymatically by, for example, furin or caspase. Cells express a low level of these endogenous enzymes, which are capable of cleaving a portion of the fusion molecules intracellularly. Thus, some of the polypeptides are secreted from the cell without being conjugated to HSA, while others are secreted in the form of fusion molecules that comprise HSA. Embodiments of the present disclosure contemplate the use of various furin fusion constructs. For example, constructs may be designed that comprise the sequence RGRR (SEQ ID NO:18), RKRKKR (SEQ ID NO:19), RKKR (SEQ ID NO:20), or RRRKKR (SEQ ID NO:21).

The present disclosure also contemplates extra-cellular cleavage (ex-vivo cleavage) whereby the fusion molecules are secreted from the cell, subjected to purification, and then cleaved. It is understood that the excision may dissociate the entire HSA-linker complex from the mature IL-15, or less that the entire HSA-linker complex.

As alluded to above, fusion of albumin to one or more polypeptides of the present disclosure can, for example, be achieved by genetic manipulation, such that the nucleic acid coding for HSA, or a fragment thereof, is joined to the nucleic acid coding for the one or more polypeptide sequences. Thereafter, a suitable host can be transformed or transfected with the fused nucleotide sequences in the form of, for example, a suitable plasmid, so as to express a fusion polypeptide. The expression may be effected in vitro from, for example, prokaryotic or eukaryotic cells, or in vivo from, for example, a transgenic organism. In some embodiments of the present disclosure, the expression of the fusion protein is performed in mammalian cell lines, for example, CHO cell lines. Transformation is used broadly herein to refer to the genetic alteration of a cell resulting from the direct uptake through the cell membrane, incorporation and expression of exogenous genetic material (exogenous nucleic acid). Transformation occurs naturally in some bacteria, but it can also be effected by artificial means in other cells.

Furthermore, albumin itself may be modified to extend its circulating half-life. Fusion of the modified albumin to IL-15 can be attained by the genetic manipulation techniques described above or by chemical conjugation; the resulting fusion molecule has a half-life that exceeds that of fusions with non-modified albumin (see WO2011/051489).

Alternative Albumin Binding Strategies: Several albumin-binding strategies have been developed as alternatives to direct fusion, including albumin binding through a conjugated fatty acid chain (acylation). Because serum albumin is a transport protein for fatty acids, these natural ligands with albumin-binding activity have been used for half-life extension of small protein therapeutics. For example, insulin determir (LEVEMIR), an approved product for diabetes, comprises a myristyl chain conjugated to a genetically-modified insulin, resulting in a long-acting insulin analog.

The present disclosure contemplates fusion proteins which comprise an albumin binding domain (ABD) polypeptide sequence and the sequence of one or more of the polypeptides described herein. Any ABD polypeptide sequence described in the literature can be a component of the fusion proteins. The components of the fusion proteins can be optionally covalently bonded through a linker, such as those linkers described herein. In some embodiments of the present disclosure, the fusion proteins comprise the ABD polypeptide sequence as an N-terminal moiety and the polypeptides described herein as a C-terminal moiety.

The present disclosure also contemplates fusion proteins comprising a fragment of an albumin binding polypeptide, which fragment substantially retains albumin binding; or a multimer of albumin binding polypeptides or fragments thereof comprising at least two albumin binding polypeptides or fragments thereof as monomer units. For a general discussion of ABD and related technologies, see WO 2012/050923, WO 2012/050930, WO 2012/004384 and WO 2009/016043.

Conjugation with Other Molecules: Additional suitable components and molecules for conjugation include, for example, thyroglobulin; tetanus toxoid; Diphtheria toxoid; polyamino acids such as poly(D-lysine:D-glutamic acid); VP6 polypeptides of rotaviruses; influenza virus hemaglutinin, influenza virus nucleoprotein; Keyhole Limpet Hemocyanin (KLH); and hepatitis B virus core protein and surface antigen; or any combination of the foregoing.

Thus, the present disclosure contemplates conjugation of one or more additional components or molecules at the N- and/or C-terminus of a polypeptide sequence, such as another polypeptide (e.g., a polypeptide having an amino acid sequence heterologous to the subject polypeptide), or a carrier molecule. Thus, an exemplary polypeptide sequence can be provided as a conjugate with another component or molecule.

A conjugate modification may result in a polypeptide sequence that retains activity with an additional or complementary function or activity derived from the second molecule. For example, a polypeptide sequence may be conjugated to a molecule, e.g., to facilitate solubility, storage, in vivo or shelf half-life or stability, reduction in immunogenicity, delayed or controlled release in vivo, etc. Other functions or activities include a conjugate that reduces toxicity relative to an unconjugated polypeptide sequence, a conjugate that targets a type of cell or organ more efficiently than an unconjugated polypeptide sequence, or a drug to further counter the causes or effects associated with a disease, disorder or condition as set forth herein (e.g., cancer).

An IL-15 polypeptide may also be conjugated to large, slowly metabolized macromolecules such as proteins; polysaccharides, such as sepharose, agarose, cellulose, or cellulose beads; polymeric amino acids, such as polyglutamic acid or polylysine; amino acid copolymers; inactivated virus particles; inactivated bacterial toxins, such as toxoid from diphtheria, tetanus, cholera, or leukotoxin molecules; inactivated bacteria; and dendritic cells. Such conjugated forms, if desired, can be used to produce antibodies against a polypeptide of the present disclosure.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates, magnetic beads, test strips, and membranes.

Purification methods such as cation exchange chromatography may be used to separate conjugates by charge difference, which effectively separates conjugates into their various molecular weights. For example, the cation exchange column can be loaded and then washed with~20 mM sodium acetate, pH~4, and then eluted with a linear (0 M to 0.5 M) NaCl gradient buffered at a pH of from about 3 to 5.5, e.g., at pH~4.5. The content of the fractions obtained by cation exchange chromatography may be identified by molecular weight using conventional methods, for example, mass spectroscopy, SDS-PAGE, or other known methods for separating molecular entities by molecular weight.

Fc-fusion Molecules: In certain embodiments, the amino- or carboxyl- terminus of a polypeptide sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product may require less frequent administration.

Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

Other Modifications: The present disclosure contemplates the use of other modifications, currently known or developed in the future, of IL-15 to improve one or more properties. One such method involves modification of the polypeptide sequences by hesylation, which utilizes hydroxyethyl starch derivatives linked to other molecules in order to modify the polypeptide sequences' characteristics. Various aspects of hesylation are described in, for example, U.S. Patent Appln. Nos. 2007/0134197 and 2006/0258607.

The present disclosure also contemplates fusion molecules comprising Small Ubiquitin-like Modifier (SUMO) as a fusion tag (LifeSensors, Inc.; Malvern, Pa.). Fusion of a polypeptide described herein to SUMO may convey several beneficial effects, including enhancement of expression, improvement in solubility, and/or assistance in the development of purification methods. SUMO proteases recognize the tertiary structure of SUMO and cleave the fusion protein at the C-terminus of SUMO, thus releasing a polypeptide described herein with the desired N-terminal amino acid.

The present disclosure also contemplates the use of PASylation™ (XL-Protein GmbH (Freising, Germany)). This technology expands the apparent molecular size of a protein of interest, without having a negative impact on the therapeutic bioactivity of the protein, beyond the pore size of the renal glomeruli, thereby decreasing renal clearance of the protein.

Linkers: Linkers and their use have been described above. Any of the foregoing components and molecules used to modify the polypeptide sequences of the present disclosure may optionally be conjugated via a linker. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids.

Exemplary flexible linkers include glycine polymers $(G)_n$, glycine-serine polymers (for example, $(GS)_n$, $GSGGS_n$ (SEQ ID NO:22), $GGGS_n$ (SEQ ID NO:23), $(G_mS_o)_n$, $(G_mS_oG_m)_n$, $(G_mS_oG_mS_oG_m)_n$ (SEQ ID NO:24), $(GSGGS_m)_n$ (SEQ ID NO:25), $(GSGS_mG)_n$ (SEQ ID NO:26) and $(GGGS_m)_n$ (SEQ ID NO:27), and combinations thereof, where m, n, and o are each independently selected from an integer of at least one), glycine-alanine polymers, alanine-serine polymers, and other flexible linkers. Glycine and glycine-serine polymers are relatively unstructured, and therefore may serve as a neutral tether between components. Exemplary flexible linkers include, but are not limited to GGSG (SEQ ID NO:28), GGSGG (SEQ ID NO:29), GSGSG (SEQ ID NO:30), GSGGG (SEQ ID NO:31), GGGSG (SEQ ID NO:32), and GSSSG (SEQ ID NO:33).

In certain embodiments of the present disclosure, PEG is conjugated to IL-15 through an activated linker that is covalently attached to one or more PEG molecules. A linker is "activated" if it is chemically reactive and ready for covalent attachment to a reactive group on a peptide. The present disclosure contemplates the use of any activated linker provided that it can accommodate one or more PEG molecules and form a covalent bond with an amino acid residue under suitable reaction conditions. In particular aspects, the activated linker attaches to an alpha amino group in a highly selective manner over other attachment sites (e.g., the epsilon amino group of lysine or the imino group of histidine).

In some embodiments, activated PEG can be represented by the formula: $(PEG)_b$-L', where PEG covalently attaches to a carbon atom of the linker to form an ether bond, b is 1 to 9 (i.e., 1 to 9 PEG molecules can be attached to the linker), and L' contains a reactive group (an activated moiety) which can react with, for example, an amino or imino group on an amino acid residue to provide a covalent attachment of the PEG to IL-15. In other embodiments, an activated linker (L') contains an aldehyde of the formula RCHO, where R is a linear or branched $C_{1-11}$ alkyl; after covalent attachment of an activated linker to IL-15, the linker contains 2 to 12 carbon atoms. The present disclosure contemplates embodiments wherein propionaldehyde is an exemplary activated linker. PEG-propionaldehyde ($CH_2CH_2CHO$) is described in U.S. Pat. No. 5,252,714 and is commercially available (e.g., Shearwater Polymers (Huntsville, Ala.). Other activated PEG-linkers can be obtained commercially from, e.g., Shearwater Polymers and Enzon, Inc. (Piscataway, N.J.).

In some embodiments, it is desirable to covalently attach more than one PEG molecule to IL-15, and a suitable activated branched (i.e., "multi-armed") linker can be used. Any suitable branched PEG linker that covalently attaches two or more PEG molecules to an amino group on an amino acid residue of IL-15 (e.g., to an alpha amino group at the N-terminus) can be used. In particular embodiments, a branched linker contemplated by the present disclosure contains two or three PEG molecules. By way of example, a branched PEG linker can be a linear or branched aliphatic group that is hydrolytically stable and contains an activated moiety (e.g., an aldehyde group), which reacts with an amino group of an amino acid residue, as described above; the aliphatic group of a branched linker can contain 2 to 12 carbons. In some embodiments, an aliphatic group can be a t-butyl which may contain, for example, three PEG molecules on each of three carbon atoms (i.e., a total of 9 PEG molecules) and a reactive aldehyde moiety on the fourth carbon of the t-butyl.

Further exemplary branched PEG linkers are described in U.S. Pat. Nos. 5,643,575, 5,919,455, 7,052,868, and 5,932,462. The skilled artisan can prepare modifications to branched PEG linkers by, e.g., addition of a reactive aldehyde moiety. Methods for preparing linkers for use are also well known in the art, and are described in, e.g., the US patents listed above.

Therapeutic and Prophylactic Uses

The present disclosure contemplates the use of the IL-15 polypeptides described herein (e.g., PEG-IL-15) in the treatment or prevention of a broad range of diseases, disorders and/or conditions, and/or the symptoms thereof. While particular uses are described in detail hereafter, it is to be understood that the present disclosure is not so limited. Furthermore, although general categories of particular diseases, disorders and conditions are set forth hereafter, some of the diseases, disorders and conditions may be a member of more than one category, and others may not be a member of any of the disclosed categories.

As discussed in more detail below, IL-15 has been shown to play a role in diseases, disorders and conditions associated with immune and inflammatory function (e.g., autoimmune-related disorders (e.g., rheumatoid arthritis), sarcoidosis, inflammatory bowel disease, and transplant rejection); cancer (e.g., leukemias, lymphoproliferative disorders, and solid tumors); and infectious diseases (e.g., HIV). [See, e.g., Fehniger, et al., Blood 97(1) (Jan. 1, 2001)].

Immune and Inflammatory Conditions. In some embodiments, the present disclosure contemplates suppression of the immune system and treatment of immune-related diseases, disorders and conditions. As used herein, terms such as "immune disease", "immune condition", "immune disorder", "inflammatory disease", "inflammatory condition", "inflammatory disorder" and the like are meant to broadly encompass any immune- or inflammatory-related condition (e.g., pathological inflammation and autoimmune diseases). Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

The IL-15 peptides described herein may be used to suppress immune function via the administration of an amount effective to inhibit one or more of the cellular events that normally occurs as a consequence of the interaction between wild-type IL-15 and the IL-15 receptor complex. Alternatively, a nucleic acid molecule encoding the IL-15 peptides described herein or recombinant cells expressing the IL-15 peptides described herein may be administered. In particular embodiments, the IL-15 peptides bind the IL-15 receptor complex with an affinity similar to wild-type IL-15, but fail to activate cell signal transduction. It is advantageous that the IL-15 peptides effectively compete with wild-type IL-15 and inhibit the events normally associated in response to IL-15 signaling.

A non-limiting list of immune- and inflammatory-related diseases, disorders and conditions which may, for example, be caused by inflammatory cytokines, include, arthritis (e.g., rheumatoid arthritis), sarcoidosis, kidney failure, lupus, asthma, psoriasis, colitis, pancreatitis, allergies, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (e.g., Crohn's disease and ulcerative colitis), allergic contact dermatitis and other eczemas, systemic sclerosis, transplantation and multiple sclerosis. Some of the aforementioned diseases, disorders and conditions for which an IL-15 molecule may be particularly efficacious (due to, for example, limitations of current therapies) are described in more detail hereafter.

The IL-15 polypeptides of the present disclosure may be particularly effective in the treatment and prevention of inflammatory bowel diseases (IBD). IBD comprises Crohn's disease (CD) and ulcerative colitis (UC), both of which are idiopathic chronic diseases that can affect any part of the gastrointestinal tract, and are associated with many untoward effects, and patients with prolonged UC are at an increased risk of developing colon cancer. Current IBD treatments are aimed at controlling inflammatory symptoms, and while certain agents (e.g., corticosteroids, aminosalicylates and standard immunosuppressive agents (e.g., cyclosporine, azathioprine, and methotrexate)) have met with limited success, long-term therapy may cause liver damage (e.g., fibrosis or cirrhosis) and bone marrow suppression, and patients often become refractory to such treatments.

Psoriasis, a constellation of common immune-mediated chronic skin diseases, affects more than 4.5 million people in the U.S., of which 1.5 million are considered to have a moderate-to severe form of the disease. Furthermore, over 10% of patients with psoriasis develop psoriatic arthritis, which damages the bone and connective tissue around the joints. An improved understanding of the underlying physiology of psoriasis has resulted in the introduction of agents that, for example, target the activity of T lymphocytes and cytokines responsible for the inflammatory nature of the disease. Such agents include the TNF-α inhibitors (also used in the treatment of rheumatoid arthritis (RA)), including ENBREL (etanercept), REMICADE (infliximab) and HUMIRA (adalimumab)), and T-cell inhibitors such as AMEVIVE (alefacept) and RAPTIVA (efalizumab). Though several of these agents are effective to some extent in certain patient populations, none have been shown to effectively treat all patients.

Rheumatoid Arthritis (RA), which is generally characterized by chronic inflammation in the membrane lining (the synovium) of the joints, affects approximately 1% of the U.S. population (~2.1 million people). Further understanding of the role of cytokines, including TNF-α and IL-1, in the inflammatory process has enabled the development and introduction of a new class of disease-modifying antirheumatic drugs (DMARDs). Agents (some of which overlap with treatment modalities for other indications) include ENBREL (etanercept), REMICADE (infliximab), HUMIRA (adalimumab) and KINERET (anakinra) Though some of these agents relieve symptoms, inhibit progression of structural damage, and improve physical function in particular patient populations, there is still a need for alternative agents with improved efficacy, complementary mechanisms of action, and fewer/less severe adverse effects.

Transplant rejection of organs and tissues has been found to involve an IL-15-related component in certain situations. Rejection is an adaptive immune response that is mediated by both cellular immunity and humoral immunity, along with components of innate immune response. Different types of transplanted organs and tissues often have different balances of rejection mechanisms. Kidney, heart, bone marrow, skin, and blood are the organs and tissues most frequently involved in transplant rejection. Treatment of transplant rejections is often dictated by the medical category of rejection (e.g., hyperacute, acute, or chronic). Immunosuppressive therapy constitutes the primary means of treating transplant rejection. Therapy is generally initiated with corticosteroids (e.g., prednisone). Combination therapy typically entails the addition of a calcineurin inhibitor (e.g., cyclosporin and tacrolimus) and an anti-proliferative agent (e.g., azathioprine). Antibodies specific to particular immune components may be added to immunosuppressive therapy; antibody therapeutics include monoclonal anti-IL-2Rα receptor antibodies (e.g., daclizumad) and monoclonal anti-CD20 antibodies (e.g., rituximab). Though helpful in many situations, alternative treatment modalities such as IL-15 related agents are needed.

Subjects suffering from multiple sclerosis (MS), a seriously debilitating autoimmune disease comprising multiple areas of inflammation and scarring of the myelin in the brain and spinal cord, may be particularly helped by the IL-15 polypeptides described herein, as current treatments only alleviate symptoms or delay the progression of disability.

Elevated serum levels of IL-15 have been observed during hepatitis C-induced liver diseases, and in liver cirrhosis and chronic hepatitis. IL-15 levels are particularly elevated in subjects suffering from hepatocellular carcinoma.

Similarly, the IL-15 polypeptides may be particularly advantageous for subjects afflicted with neurodegenerative disorders, such as Alzheimer's disease (AD), a brain disorder that seriously impairs patients' thought, memory, and language processes; Parkinson's disease (PD), a progressive disorder of the CNS characterized by, for example, abnormal movement, rigidity and tremor; and diabetes mellitus. These disorders are progressive and debilitating, and no curative agents are available.

Cancer and Related Conditions. In accordance with the present disclosure, an IL-15 molecule (e.g., peptide) described herein can be used to treat a subject having undesirable proliferation of cells that express an IL-15 receptor. Alternatively, a nucleic acid molecule encoding the IL-15 peptides described herein or recombinant cells expressing the IL-15 peptides described herein may be administered. Though an understanding of the underlying mechanism of action by which IL-15 exerts an anti-proliferative effect is not required to practice the present disclosure, cellular proliferation may be inhibited by complement-directed cytolysis or antibody-dependent cellular toxicity.

The IL-15 peptides described herein can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present disclosure also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas (e.g., cutaneous T-cell lymphoma (CTCL), carcinomas, melanomas, leukemias, myelomas, sarcomas, teratocarcinomas, chemically-induced cancers, metastasis, and angiogenesis.

In particular embodiments, the tumor or cancer is colon cancer, ovarian cancer, breast cancer, melanoma, lung cancer, glioblastoma, or leukemia (e.g., HTLV-1 -mediated adult T-cell leukemia). The use of the term(s) cancer-related diseases, disorders and conditions is meant to refer broadly to conditions that are associated, directly or indirectly, with cancer, and includes, e.g., angiogenesis and precancerous conditions such as dysplasia.

In some embodiments, the present disclosure provides methods for treating a proliferative condition, cancer, tumor, or precancerous condition with an IL-15 molecule and at least one additional therapeutic or diagnostic agent, examples of which are set forth elsewhere herein.

Viral and Bacterial Conditions. There has been increased interest in the role of IL-15 in viral and bacterial diseases, disorders and conditions. IL-15 has been postulated to produce both stimulatory and inhibitory effects depending on its receptor binding activity and other factors.

Regarding human immunodeficiency virus (HIV), IL-15, through its ability to mimic the actions of IL-2, has two conflicting effects. One effect is the potentially beneficial enhancement of immune function, while the other effect is the potentially detrimental activation of HIV replication. These opposing effects are also present in other viral-related disorders. A close temporal correlation was observed between IL-15 levels and fluctuations in viral load. The present disclosure contemplates the use of the IL-15 polypeptides in the treatment and/or prevention of any viral disease, disorder or condition for which treatment with IL-15 may be beneficial. Examples of viral diseases, disorders and conditions that are contemplated include Epstein-Barr virus, hepatitis B, hepatitis C, HIV, herpes simplex virus and cytomegalovirus (CMV).

IL-15 has recently been associated with certain bacterial and other invasive infections. By way of example, reports indicate that administration of recombinant IL-15 before infection caused by, e.g., *Salmonella* and *Plasmodium falciparum* improves host defense against, and clearance of, the organism.

Pharmaceutical Compositions

The IL-15 polypeptides of the present disclosure may be in the form of compositions suitable for administration to a subject. In general, such compositions are "pharmaceutical compositions" comprising IL-15 and one or more pharmaceutically acceptable or physiologically acceptable diluents, carriers or excipients. In certain embodiments, the IL-15 polypeptides are present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present disclosure.

The pharmaceutical compositions typically comprise a therapeutically effective amount of an IL-15 polypeptide contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus may be used to deliver IL-15, including implants (e.g., implantable pumps) and catheter systems, slow injection pumps and devices, all of which are well known to the skilled artisan. Depot injections, which are generally administered subcutaneously or intramuscularly, may also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The pharmaceutical compositions containing the active ingredient may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known in the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrylate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed.

The present disclosure contemplates the administration of the IL-15 polypeptides in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The IL-15 polypeptides contemplated by the present disclosure may be in the form of any other suitable pharmaceutical composition (e.g., sprays for nasal or inhalation use) currently known or developed in the future.

The concentration of a polypeptide or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present disclosure contemplates the administration of IL-15 molecules, and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation. Depot injections, which are generally administered subcutaneously or intramuscularly, may also be utilized to release the IL-15 molecules disclosed herein over a defined period of time.

Particular embodiments of the present disclosure contemplate parenteral administration, and in further particular embodiments the parenteral administration is subcutaneous.

Combination Therapy

The present disclosure contemplates the use of IL-15 molecules in combination with one or more active therapeutic agents (e.g., cytokines) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the IL-15 polypeptides and the one or more active therapeutic agents or other prophylactic or therapeutic modalities are administered or applied sequentially, e.g., where one agent is administered prior to one or more other agents. In other embodiments, the IL-15 polypeptides and the one or more active therapeutic agents or other prophylactic or therapeutic modalities are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

The IL-15 polypeptides of the present disclosure may be used in combination with at least one other (active) agent in any manner appropriate under the circumstances. In one embodiment, treatment with the at least one active agent and at least one IL-15 polypeptide of the present disclosure is maintained over a period of time. In another embodiment, treatment with the at least one active agent is reduced or discontinued (e.g., when the subject is stable), while treatment with the IL-15 polypeptide of the present disclosure is maintained at a constant dosing regimen. In a further embodiment, treatment with the at least one active agent is reduced or discontinued (e.g., when the subject is stable), while treatment with the IL-15 polypeptide of the present disclosure is reduced (e.g., lower dose, less frequent dosing or shorter treatment regimen). In yet another embodiment, treatment with the at least one active agent is reduced or discontinued (e.g., when the subject is stable), and treatment with the IL-15 polypeptide of the present disclosure is increased (e.g., higher dose, more frequent dosing or longer treatment regimen). In yet another embodiment, treatment with the at least one active agent is maintained and treatment with the IL-15 polypeptide of the present disclosure is reduced or discontinued (e.g., lower dose, less frequent dosing or shorter treatment regimen). In yet another embodiment, treatment with the at least one active agent and treatment with the IL-15 polypeptide of the present disclosure are reduced or discontinued (e.g., lower dose, less frequent dosing or shorter treatment regimen).

Immune and Inflammatory Conditions. The present disclosure provides methods for treating and/or preventing immune- and/or inflammatory-related diseases, disorders and conditions, as well as disorders associated therewith, with an IL-15 molecule and at least one additional therapeutic or diagnostic agent.

Examples of therapeutic agents useful in combination therapy include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors.

Other active agents for combination include steroids such as prednisolone, prednisone, methylprednisolone, betamethasone, dexamethasone, or hydrocortisone. Such a combination may be especially advantageous since one or more adverse effects of the steroid can be reduced or even eliminated by tapering the steroid dose required.

Additional examples of active agents that may be used in combinations for treating, for example, rheumatoid arthritis, include cytokine suppressive anti-inflammatory drug(s) (CSAIDs); antibodies to, or antagonists of, other human cytokines or growth factors, for example, TNF, LT, IL-1β, IL-2, IL-6, IL-7, IL-8, IL-10, IL-16, IL-18, EMAP-II, GM-CSF, FGF, or PDGF.

Particular combinations of active agents may interfere at different points in the autoimmune and subsequent inflammatory cascade, and include TNF antagonists such as chimeric, humanized or human TNF antibodies, REMICADE, anti-TNF antibody fragments (e.g., CDP870), and soluble p55 or p75 TNF receptors, derivatives thereof, p75TNFRIgG (ENBREL.) or p55TNFR1gG (LENERCEPT), soluble IL-13 receptor (sIL-13), and also TNFα-converting enzyme (TACE) inhibitors; similarly, IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the IL-15 polypeptides described herein include interferon-β1a (AVONEX); interferon-β1b (BETASERON); copaxone; hyperbaric oxygen; intravenous immunoglobulin; clabribine; and antibodies to, or antagonists of, other human cytokines or growth factors (e.g., antibodies to CD40 ligand and CD80).

The present disclosure encompasses pharmaceutically acceptable salts, acids or derivatives of any of the above.

Cancer and Related Conditions. The present disclosure provides methods for treating and/or preventing a proliferative condition; a cancer, tumor, or precancerous disease, disorder or condition with an IL-15 molecule and at least one additional therapeutic or diagnostic agent.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above. Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and anti-androgens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

Additional treatment modalities that may be used in combination with the IL-15 polypeptides include a cytokine or cytokine antagonist, such as IL-12, INFα, or anti-epidermal growth factor receptor, radiotherapy, a monoclonal antibody against another tumor antigen, a complex of a monoclonal antibody and toxin, a T-cell adjuvant, bone marrow transplant, or antigen presenting cells (e.g., dendritic cell therapy). Vaccines (e.g., as a soluble protein or as a nucleic acid encoding the protein) are also provided herein.

The present disclosure encompasses pharmaceutically acceptable salts, acids or derivatives of any of the above.

Viral and Bacterial Conditions. The present disclosure provides methods for treating and/or preventing viral diseases, disorders and conditions, as well as disorders associated therewith, with an IL-15 molecule and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); and agents that prevent release of viral particles (e.g., zanamivir and oseltamivir). Treatment and/or prevention of certain viral infections (e.g., HIV) frequently entail a group ("cocktail") of antiviral agents. Other antiviral agents contemplated for use in combination with IL-15 polypeptides include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, efavirenz, emtricitabine, enfuvirtide, entecavir, famciclovir, fosamprenavir, foscarnet, fosfonet, ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nevirapine, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

IL-15 treatment of the Salmenella genus of rod-shaped Gram-negative bacteria is thought to be most effective in combination with vaccines currently under development. In regards to combination therapy for the treatment of Plasmodium falciparum parasite, the antimalarial medications (e.g., cholorquines) ant the artemisininis may be effective in combination therapy with IL-15 peptides.

The present disclosure encompasses pharmaceutically acceptable salts, acids or derivatives of any of the above.

Dosing

The IL-15 polypeptides of the present disclosure may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the IL-15 molecules of the present disclosure may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject. The amount of an IL-15 molecule necessary to treat a disease, disorder or condition described herein is based on the IL-15 activity of the conjugated protein, which can be determined by IL-15 activity assays known in the art.

The therapeutically effective amount of an IL-15 molecule can range from about 0.01 to about 100 μg protein/kg of body weight/day, from about 0.1 to 20 μg protein/kg of body weight/day, from about 0.5 to 10 μg protein/kg of body weight/day, or from about 1 to 4 μg protein/kg of body weight/day. In some embodiments, the therapeutically effective amount of an IL-15 molecule can range from about 1 to 16 μg protein/kg of body weight/day. The present disclosure contemplates the administration of an IL-15 molecule by continuous infusion to delivery, e.g., about 50 to 800 μg protein/kg of body weight/day. The infusion rate may be varied based on evaluation of, for example, adverse effects and blood cell counts.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, or 1000.0 milligrams of the active ingredient.

In certain embodiments, the dosage of the disclosed IL-15 polypeptide is contained in a "unit dosage form". The phrase "unit dosage form" refers to physically discrete units, each unit containing a predetermined amount of a IL-15 polypeptide of the present disclosure, either alone or in combination with one or more additional agents, sufficient to produce the desired effect. It will be appreciated that the parameters of a unit dosage form will depend on the particular agent and the effect to be achieved.

Kits

The present disclosure also contemplates kits comprising IL-15, and pharmaceutical compositions thereof. The kits are generally in the form of a physical structure housing various components, as described below, and may be utilized, for example, in practicing the methods described herein.

A kit can include one or more of the IL-15 polypeptides disclosed herein (provided in, e.g., a sterile container), which may be in the form of a pharmaceutical composition suitable for administration to a subject. The IL-15 polypeptides can be provided in a form that is ready for use or in a form requiring, for example, reconstitution or dilution prior to administration. When the IL-15 polypeptides are in a form that needs to be reconstituted by a user, the kit may also include buffers, pharmaceutically acceptable excipients, and the like, packaged with or separately from the IL-15 polypeptides. When combination therapy is contemplated, the kit may contain the several agents separately or they may already be combined in the kit. Each component of the kit may be enclosed within an individual container, and all of the various containers may be within a single package. A kit of the present disclosure may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD-or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below were performed and are all of the experiments that may be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric.

Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); ng=nanogram; µg=microgram; mg=milligram; g=gram; kg=kilogram; dl or dL=deciliter; µl or µL=microliter; ml or mL=milliliter; l or L=liter; nM=nanomolar; µM=micromolar; mM=millimolar; M=molar; kDa=kilodalton; i.m.=intramuscular(ly); i.p.=intraperitoneal(ly); s.c.=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; PCR=polymerase chain reaction; NHS=N-Hydroxysuccinimide; DMEM=Dulbeco's Modification of Eagle's Medium; GC=genome copy; ELISA=enzyme-linked immuno sorbent assay; EDTA=ethylenediaminetetraacetic acid; PMA=phorbol myristate acetate; rhIL-15-=recombinant human IL-15; LPS=lipopolysaccharide.

Materials and Methods

The following general materials and methods may be used in the Examples below:

Standard methods in molecular biology are described (see, e.g., Sambrook and Russell (2001) Molecular Cloning, 3$^{rd}$ ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Production, purification, and fragmentation of polyclonal and monoclonal antibodies are described (e.g., Harlow and Lane (1999) Using Antibodies, Cold Spring Harbor Laboratory Press, Cold Spring Harbor, N.Y.); standard techniques for characterizing ligand/receptor interactions are available (see, e.g., Coligan et al. (2001) Current Protocols in Immunology, Vol. 4, John Wiley, Inc., NY); methods for flow cytometry, including fluorescence-activated cell sorting (FACS), are available (see, e.g., Shapiro (2003) Practical Flow Cytometry, John Wiley and Sons, Hoboken, N.J.); and fluorescent reagents suitable for modifying nucleic acids, including nucleic acid primers and probes, polypeptides, and antibodies, for use, for example, as diagnostic reagents, are available (Molecular Probes (2003) Catalogue, Molecular Probes, Inc., Eugene, Oreg.; Sigma-Aldrich (2003) Catalogue, St. Louis, Mo.).

Standard methods of histology of the immune system are described (see, e.g., Louis et al. (2002) Basic Histology: Text and Atlas, McGraw-Hill, New York, N.Y.).

Depletion of immune cells (CD4$^+$ and CD8$^+$ T-cells) may be effected by antibody-mediated elimination. For example, 250 µg of CD4- or CD8-specific antibodies may be injected weekly, and cell depletions verified using FACS and IHC analysis.

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, Calif.); and DeCypher™ (TimeLogic Corp., Crystal Bay, Nev.).

Immunocompetent Balb/C or B-cell—deficient Balb/C mice may be obtained from The Jackson Lab., Bar Harbor, Me. and may be used in accordance with standard procedures (see, e.g., Martin et al (2001) Infect. Immun., 69(11): 7067-73 and Compton et al. (2004) Comp. Med. 54(6):681-89). Other mice strains suitable for the experimental work contemplated by the present disclosure are known to the skilled artisan and are generally available from The Jackson Lab. The skilled artisan is familiar with models and cell lines (e.g., models of inflammation) that may also be used in the practice of the present disclosure.

Serum IL-15 concentration levels and exposure levels may be determined by standard methods used in the art. For example, a serum exposure level assay can be performed by collecting whole blood (~50 µL/mouse) from mouse tail snips into plain capillary tubes, separating serum and blood cells by centrifugation, and determining IL-15 exposure levels by standard ELISA kits (e.g., R&D Systems) and techniques. Alternatively, or in addition, the ELISA protocol described below (or a similar protocol) can be adapted to measure serum levels of human IL-15 as a means of determining in vivo half-life of a mutein or modified mutein.

Generation and Assessment of Muteins

Assembly of the Human IL-15 Expression Vector, pSecTag2hygro-huIL15. A human IL-15 mammalian expression vector may be assembled by amplifying the complete human IL-15 open reading frame via PCR using Platinum Pfx DNA Polymerase (Life Technologies #11708-039, following manufacturer's protocol) using pCMV6-AC-human-IL15 (Origene #SC324164, Genbank accession #NM_000585.4) as a DNA template and primers 5'-tataG-GCCCAGCCGGCCgccgccaccATGAGAATTTCGAAAC-CACATTTGAG-3' (SEQ ID NO:34) and 5'-tatagggcccT-CAAGAAGTGTTGATGAACATTTGG-3' (SEQ ID NO:35), and the resultant PCR reaction may be purified using a QIAquick PCR Purification Kit (Qiagen #28106). The purified human IL-15 PCR fragment and the mammalian expression vector pSecTag2hygro (B) (Life Technologies #V910-20) may be digested with SfiI and ApaI (New England Biolabs, Ipswich, Mass.) for one hour at 37° C. with Calf Intestinal Phosphatase (New England Biolabs, Ipswich, Mass.) added to the pSecTag2hygro (B) digestion. The digested DNA fragments may be run on a 1% agarose gel (Lonza #54803) for one hour at 100V, and then excised and purified using a QIAquick Gel Extraction Kit (Qiagen #28706). The human IL-15 PCR fragment may be ligated into the pSecTag2hygro (B) vector using the Rapid DNA Ligation Kit (Roche #11635379001), transformed into One Shot TOP10 Chemically Competent *E. coli* (Life Technologies #C404006), plated to agar plates containing 100 μg/mL ampicillin and grown overnight at 37° C. The following day, bacterial colonies may be picked individually and placed into 3 mL cultures containing LB+100 μg/mL ampicillin and grown for 8-20 hours at 37° C. in a shaking incubator at 200 RPM. Two (2) mL of each culture may then be aliquoted to 2 mL tubes, the cells pelleted at 6000 RPM in a table-top centrifuge for 10 minutes, the media aspirated, and the DNA purified away from the bacteria using a QIAprep Spin Miniprep Kit (Qiagen #27106). Correct expression vectors may be identified via DNA sequencing (MC Lab, South San Francisco, Calif.).

Generation of Mutein Expression Vectors. Human IL-15 mutein expression vectors were assembled by mutating the previously described human IL-15 mammalian expression vector pSecTag2hygro-huIL-15 using a Quikchange II Site-Directed Mutagenesis Kit (Agilent Technologies #200524) following the manufacturer's protocol with the following clarifications: primers did not always meet the recommended Tm; the PCR reaction was cycled for 16-18 rounds with an extension time of 6-7 minutes; 4 μL of the DpnI—treated reaction was transformed into One Shot TOP10 Chemically Competent Cells (Life Technologies #C404006) as previously described. Three (3) mL miniprep cultures were grown, purified, and sequence-verified as previously described. For some muteins, a 400 mL culture was grown and purified. Briefly, one bacterial colony was picked into 400 mL LB+100 μg/mL ampicillin, and grown for 12-20 hours at 37° C. in a shaking incubator at 200 RPM in a 2L baffled Erlenmeyer flask. The culture was then pelleted in a centrifuge (6000 RPM in a Beckman Avanti J-25T in a JA-10 rotor for 20 minutes), the media aspirated, and the DNA extracted using an EndoFree Plasmid Mega Kit (Qiagen, #12381), following the manufacturer's protocol (with very minor changes, of a type familiar to the skilled artisan, made to the DNA precipitation methodology to increase the final DNA concentration).

Muteins which required multiple amino acid changes were assembled by inserting one mutation at a time. The introduction of the N-glycosylation motifs, N-X-S and N-X-T, sometimes required the introduction of three mutations since X≠P (Proline). The numbering convention used for the muteins assigns the start codon as the first position, hence the first 48 residues (MRISKPHLRSISIQCYLCLLLNSH-FLTEAGIHVFILGCFSAGLPKTEA (SEQ ID NO:36)) comprise the signal peptide and the first residue of the mature protein would be Asparagine 49.

Protein Transfection Protocol. All human IL-15 expression vectors (wild type and mutein) may be transiently expressed in HEK293FT cells (Life Technologies #R700-07). The cells may be maintained in 50 mL of DMEM (Life Technologies #11995-073)+10% characterized fetal bovine serum (Hyclon/Thermo Scientific #SH30071.03)+1× Penicillin/Streptomycin (Life Technologies #15140-122) at 37° C. at 5% $CO_2$ in T175 flasks (Greiner One/CellStar #660175). Upon reaching confluence, the cells may be detached with 10 mL of PBS+5 mM EDTA, the cells collected with an additional 10 mL of growth media, pelleted at 1000 RPM in a centrifuge (Beckman Allegra 6R), the media aspirated, the cells resuspended in fresh media, and then split between three T175 flasks each containing 45 mL of growth media.

All expression vectors may be transfected into either 6-well plates or T175 flasks. For 6-well plate transfections, the Hek293FT cells may be harvested from a confluent T175 flask, the cells collected as previously described and then resuspended in 20 mL of fresh growth media. Seven hundred (700) μL of the cell suspension may be added to each well of a 6-well plate (Falcon #353046) containing 2 mL of fresh media and grown overnight as described. The following day, the cells may be transfected using Lipofectamine 2000 (Life Technologies #1388795) using the following protocol: 250 μl of OptiMEMI Reduced Serum Media (Life Technologies #31985-088) may be aliquoted to two Eppendorf tubes, then 10 μL of Lipofectamine 2000 Transfection Reagent (Life Technologies #1388795) may be added to one aliquot and 4 μg of DNA to the other. The two solutions may be incubated separately for 5 minutes at room temperature and then the transfection complexes may be formed by combining the two solutions and incubating them at room temperature for an additional 30 minutes. The complete 500 μL mixture may then be added drop-wise to one well of the 6-well plate, and returned to the incubator for 4 hours. The transfection media may then be aspirated and replaced with DMEM+Penicillin/Streptomycin and grown for approximately 36 hours. The conditioned media may then be harvested and stored at 4° C. T175-flasks may then be transfected as described above with the following exceptions: T175 flasks with 42-45 mL of growth media may be grown to 95% confluence prior to transfection, and the transfection complexes may be formed by adding 175 μL of Lipofectamine 2000 to 4.4 mL OptiMEM I and 75-100 μL of DNA to a second 4.4 mL of OptiMEM I. Upon aspiration of the transfection complexes, 50 mL of media may be added to each flask.

Mock transfections may contain either empty pSecTag2hygro (B) expression vector or no DNA, and may be prepared as previously described.

Human IL-15 Detection ELISA. A 96-well plate (Nunc Maxisorp #442404) may be coated overnight at 4° C. with 100 μL/well PBS+1 μg/mL anti-human IL-15 antibody (e.g., ATCC HB-12062, clone M111, Manassas, Va.), washed 6×200 μL in DPBS-Tween 20 (Teknova #P0297), blocked in 200 μL/well PBS+5% BSA (Calbiochem #2960) for 2 hr at room temperature on a rocking platform, and washed as previously described. The samples may be serially diluted in PBS and 100 μL/well may be added to the assay plate. Samples may be run in duplicate or triplicate. As a positive control, purified human IL-15 may be spiked in, while buffer or conditioned media from a mock transfection may be used as a negative control, and both serially diluted. The samples may be incubated overnight at 4° C. on a rocking platform and then washed as previously described. 100 μL/well of PBS+anti-human-IL-15 antibody (e.g., ab7213; Abcam) may be added to each well, incubated for one hour at room temperature on a rocking platform, washed as previously described, and then 100 μ/well of donkey anti-rabbit IgG (H+L)–HRP (Jackson Immuno Research # 711-035-152, diluted 1:10,000) may be added and incubated for an additional 1 hr at room temperature on a rocking platform. The plate may be washed as described and developed with 100 µL/well of 1-Step Ultra TMB-ELISA (Pierce/Thermo #34029) for 1-5 mins, and then the reaction stopped with 100 µL/well Stop Solution (Life Technologies #SS04). The plate may be read on a Molecular Devices M2 plate reader at 450 nm.

Another ELISA format could include premade kits (e.g., following the manufacturer's recommended protocol in the Human IL-15 Quantikine ELISA Kit (R&D Systems #D1500, Minneapolis, Minn.)).

Purification of Wild Type and Mutein Human IL-15. An anti-human-IL-15 antibody (e.g. ATCC HB-12062, clone M111, Manassas, Va.) may be coupled to CNBr-activated Sepharose 4 Fast Flow (GE Healthcare #71-5000-15 AF, following the manufacturer's protocol) and equilibrated in PBS. 500 µL-1 mL of M111-sepharose may be added per 100 mL of conditioned media contained in a glass Econo-Column (Bio-Rad, Hercules, Calif.) and incubated for 1-2 hours at room temperature on a rocking platform. The media may be run through the column via gravity flow, washed 1×with 1×PBS (pH 7.4), eluted with 0.1M glycine (pH 2.9) and neutralized with a 10% volume of 1M Tris buffer (pH 8.0). The protein may be concentrated and buffer exchanged into PBS (pH 7.4) using an Amicon Ultra Centrifugal Filter Device (Millipore, Billerica, Mass.; 5,000 kD molecular weight cutoff). Protein concentration may be determined by spectrophotometer at 280 nm.

SEC Analysis Proteins. Using a 1100 series HPLC (Agilent Technologies, Santa Clara, Calif.), 20-50 µg of protein may be injected onto a TSK3000sw column (Tosoh Biosciences, Tokyo, JP), equilibrated with PBS (pH 7.4), and run at a flow rate of 1 mL/min.

Pegylation of IL-15

The PEG (NOF Corporation, Japan) may be diluted to a concentration of 10 -100 mg/mL, in 50 mM phosphate with 100 mM NaCl at pH 4- 8, and the human IL-15 may be diluted to a concentration of 2-10 mg/mL in PBS, pH 7.4. The final reaction mixture may include the PEG and human IL-15 at a 10:1 to 2:1-ratio range (PPA PEG:human IL-15), and sodium cyanoborohydride at a final concentration of 5-50mM. The reaction may be incubated from 4° C. -25° C. for 2-48 hrs. To select the desired protein species and/or buffer exchange, the pegylated protein may be fractionated via SEC (as previously described), or to eliminate most of the non-protein species in the pegylation reaction mixture and/or buffer exchange, the PEG-IL-15 reaction mixture may undergo an ultrafiltration step (e.g. a Millipore Labscale TFF system may be used with a regenerated cellulose (PLCGC) membrane, with a 5 kDa molecular weight cut off).

Assays to Determine the Bioactivity of Modified Forms of IL-15

The present disclosure contemplates the use of any assays and methodologies known in the art for determining the bioactivity of the IL-15 molecules described herein. The assays described hereafter are representative, and not exclusionary.

CTLL-2 Cell Proliferation Assay. Soman et al. (J Immunol Methods 348(1-2):83-94 (2009 Aug. 31)) describe an optimized tetrazolium dye-based colorimetric cell proliferation assay of CTLL-2 cells using soluble CellTiter96 Aqueous One Reagent (Promega; Madison, Wis.) to quantitatively estimate IL-15 biological activity. CTLL-2 is an IL-2 dependent murine cell line.

A CTLL-2 cell proliferation assay substantively similar to that described by Soman et al. was used herein to determine IL-15 biological activity. Briefly, CTLL-2 cells (ATCC TIB-214, Manassas, Va.) were cultured in RPMI 1640 (Life Technologies, 11875-093, Grand Island, N.Y.) supplemented with 10% FBS and 10% T-STIM (Corning #354115, Tewsbury, Mass.). The cells were maintained at 37° C. supplemented with 5% $CO_2$ at a density between 10,000 cells/mL and 100,000 cells/mL, and harvested when they were growing in a logarithmic phase (typically 2-3 weeks after thawing; cell viability≥95%) and washed four times with 20 mL of growth media without T-STIM (by centrifugation at 1000 rpm, 5 min). 25,000 cells/well in 100 µL of growth media without T-STIM were then aliquoted into clear 96-well tissue culture plates and returned to the incubator while the proteins were diluted. The IL-15 samples were diluted to an initial concentration of 8 ng/mL in the assay medium followed by serial two-fold dilutions, and then 100 µL added to the wells of a 96-well tissue culture plate and returned to the 37° C., 5% $CO_2$ incubator for 48 hr. After the 48 hr incubation period, CellTiter96® Aqueous One Solution was added (20 µL/well) and the suspension incubated for another 1-4 hr at 37° C. and 5% $CO_2$. The plate was read at 490 nm, and the background readings in the wells with medium were subtracted from the sample well read-outs.

M07e Cell Proliferation Assay. Kanakura et al. (Blood 76(4):706-15 (1990 Aug. 15)); Caliceti et al. (PLoS One 7(7): e41246. doi:10.1371/journal.pone.0041246 (2012)); and Zauner et al. (BioTechniques 20:905-13 (May 1996)) describe cell proliferation assays using M07e, a human leukemia megakaryocytic cell line whose proliferation is IL-3 or GM-CSF dependent. M07e cells may be purchased from DSMZ (DSMZ No. ACC 104; Braunschweig, Germany).

The M07e cell line may be cultured in RPMI 1640 medium (Gibco, Grand Island, N.Y.) supplemented with 10% FBS, rhGM-CSF (10 ng/mL) or rhIL-3 (10 ng/mL); alternatively, cells may be cultured in IMDM supplemented with 5% FCS and 10 ng/mL IL3. MTT [3-(4,5-dimethylthiazol-2-yl)-2,5-diphenyl tetrazolium bromide (Sigma) incorporation may be used to quantitate factor-induced proliferation of M07e cells. Briefly, triplicate aliquots of M07e cells may be cultured in flat-bottom microtiter plates (100 µL/well) for 72 hours at 37° C. MTT may be added for the final 4 hrs of culture (10 L of a 5mg/mL solution of MTT in PBS). At 72 hrs, 100 µL of acid isopropanol (0.04 N HCl in isopropanol) may be added to all wells, mixed, and the optical density measured on a micro ELISA plate reader at 540 nm.

CD8+/CD4+T-cell Assays. Activated primary human CD8+ and CD4+ T-cells secrete IFNγ, Granzyme B, Perforin and TNFα when treated with PEG-IL-15. The following protocol provides an exemplary assay for screening for the production of these cytokines. Human primary peripheral blood mononuclear cells (PBMCs) may be isolated according to any standard protocol (see, e.g., Fuss et al. (2009) Current Protocols in Immunology, Unit 7.1, John Wiley, Inc., NY). 2.5 mL of PBMCs (at a cell density of 10 million cells/mL) may be cultured per well with complete RPMI, containing RPMI (Life Technologies; Carlsbad, Calif.), 10 mM HEPES (Life Technologies; Carlsbad, Calif.), 10% Fetal Calf Serum (Hyclone Thermo Fisher Scientific; Waltham, Mass.) and Penicillin/Streptomycin cocktail (Life Technologies; Carlsbad, Calif.), or in AIM-V serum-free media (Life Technologies #12055-083), in any standard tissue culture treated 6-well plate (BD; Franklin Lakes, N.J.) in a humidified 37° C. incubator with 5% $CO_2$. CD8+ and CD4+ T-cells may be isolated using Miltenyi Biotec's MACS cell separation technology according to the manufacture's protocol (Miltenyi Biotech; Auburn, Calif.). The T-cells may be activated by coating a 24-well tissue culture plate (Costar #3526, Corning, N.Y.) with anti-CD3 and antiCD-28 antibodies (Affymetrix eBioscience; San Diego, Calif.) and by adding 3E6 cells/well in 1ml of AIM-V media. The cells may be grown for 3 days as described, then collected and resuspended in fresh AIM-V at a density of 2E6 cells/mL, and 250 μL/well aliquoted into a 96-well tissue culture plate (Falcon #353072, Corning, N.Y.). Human PEG-IL-15 may be serially diluted and added to the wells at a final concentration of 1 μg/mL to 0.01 ng/ml; the cells may be incubated in a humidified 37° C. incubator with 5% $CO_2$ for 3 days. The media may then be collected and assayed for IFNγ, Granzyme B, Perforin and/or TNFα using a commercial ELISA kit and following the manufacture's protocol (e.g., Affymetrix Bioscience; San Diego, Calif. or R&D Systems, Minneapolis, Minn.)).

NK Cell Assays. Human NK cells may be isolated from the PBMC cells (protocol previously described; cultured in complete RPMI) and similarly isolated using Miltenyi Biotec's MACS cell separation technology according to the manufacture's protocol (Miltenyi Biotech; Auburn, Calif.). The cells may be grown and cultured (as described for the T-cells, using complete RPMI), plated in a 96-well tissue culture plate (Falcon #353072, Corning, N.Y.) at 5E5 cells/well in 250 μl of complete RPMI. After 1-3 days for growth, the media may be assayed as described for the T-cells.

Tumor Models and Tumor Analysis

Any art-accepted tumor model, assay, and the like can be used to evaluate the effect of the IL-15 molecules described herein on various tumors. The tumor models and tumor analyses described hereafter are representative of those that can be utilized.

Syngeneic mouse tumor cells are injected subcutaneously or intradermally at $10^4$, $10^5$ or $10^6$ cells per tumor inoculation. Ep2 mammary carcinoma, CT26 colon carcinoma, PDV6 squamous carcinoma of the skin and 4T1 breast carcinoma models can be used (see, e.g., Langowski et al. (2006) Nature 442:461-465). Immunocompetent Balb/C or B-cell deficient Balb/C mice can be used. PEG-mIL-15 can be administered to the immunocompetent mice, while PEG-hIL-15 treatment can be in the B-cell deficient mice. Tumors are allowed to reach a size of 100-250 mm³ before treatment is started. IL-15, PEG-mIL-15, PEG-hIL-15, or buffer control is administered subcutaneously at a site distant from the tumor implantation. Tumor growth is typically monitored twice weekly using electronic calipers.

Tumor tissues and lymphatic organs are harvested at various endpoints to measure mRNA expression for a number of inflammatory markers and to perform immunohistochemistry for several inflammatory cell markers. The tissues are snap-frozen in liquid nitrogen and stored at −80° C. Primary tumor growth is typically monitored twice weekly using electronic calipers. Tumor volume may be calculated using the formula (width²×length/2) where length is the longer dimension. Tumors are allowed to reach a size of 90-250 mm³ before treatment is started.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application was specifically and individually indicated to be incorporated by reference.

What is claimed:

1. A peptide comprising an amino acid sequence of SEQ ID NO:3, wherein the peptide comprises:
   a) a Helix A,
   b) an A/B Inter-helix Junction,
   c) a Helix B,
   d) a B/C Inter-helix Junction,
   e) a Helix C,
   f) a C/D Inter-helix Junction and
   g) a Helix D;
   and wherein the peptide further comprises at least one amino acid substitution of the following positions: 1, 17-23, 60, 89-98, 113, or 114.

2. The peptide of claim 1, wherein substitution of the at least one amino acid is a conservative substitution.

3. The peptide of claim 1 or 2, wherein the peptide has a bioactivity at least equal to the bioactivity of SEQ ID NO:3, wherein the bioactivity is determined in an in vitro assay or an in vivo assay.

4. The peptide of claim 3, wherein the bioactivity is determined in an in vitro assay selected from the group consisting of a TNFα production assay, a CTLL-2 cell proliferation assay, a M07e cell proliferation assay, or a T-cell IFNγ secretion assay.

5. The peptide of claim 1, wherein the at least one amino acid substitution does not adversely affect immunogenicity.

6. The peptide of claim 5, wherein the immunogenicity of the peptide is predicted by screening for at least one of T-cell epitopes or B-cell epitopes.

7. The peptide of claim 6, wherein the screening is at least one of an in silico screening system or an ex vivo assay system.

8. The peptide of claim 1, wherein the peptide comprises at least one modification to form a modified peptide;
   wherein the modification does not alter the amino acid sequence of the peptide, and
   wherein the modification improves at least one property of the peptide.

9. The peptide of claim 8, wherein the modified peptide is pegylated with a PEG component.

10. The peptide of claim 9, wherein the modified peptide comprises at least one PEG molecule covalently attached to the N-terminus of the peptide.

11. The peptide of claim 9, wherein the PEG component of the modified peptide has a molecular mass from 5 kDa to 50 kDa.

12. The peptide of claim 9, wherein the PEG component of the modified peptide has a molecular mass from 20 kDa to 40 kDa.

13. The peptide of claim 9, wherein the PEG component of the modified peptide has a molecular mass greater than 20 kDa.

14. The peptide of claim 9, wherein the PEG component of the modified peptide has a molecular mass of at least 30 kD.

15. The peptide of claim 9, wherein the PEG component of the modified peptide has a molecular mass of at least 40 kD.

16. The peptide of claim 8, wherein the modified peptide is glycosylated.

17. The peptide of claim 8, wherein the modified peptide comprises an Fc fusion molecule.

18. The peptide of claim 8, wherein the modified peptide comprises a serum albumin.

19. The peptide of claim 8, wherein the modification is site-specific.

20. The peptide of claim 8, wherein the modification comprises a linker.

21. The peptide of claim 8, wherein the modification improves at least one physical property of the peptide.

22. The peptide of claim 21, wherein the physical property is selected from the group consisting of solubility, bioavailability, serum half-life, and circulation time.

23. The peptide of claim 8, wherein the modified peptide has activity at least comparable to the activity of mature human IL-15.

24. The peptide of claim 1, wherein the peptide is produced recombinantly.

25. A pharmaceutical composition, comprising a peptide of claim 1, and a pharmaceutically acceptable diluent, carrier or excipient.

* * * * *